United States Patent
Aisaka et al.

(10) Patent No.: US 10,863,897 B2
(45) Date of Patent: *Dec. 15, 2020

(54) IMAGE PROCESSING APPARATUS AND METHOD

(71) Applicant: SONY CORPORATION, Tokyo (JP)

(72) Inventors: Kazuki Aisaka, Kanagawa (JP); Seiji Kobayashi, Tokyo (JP); Takuya Kishimoto, Tokyo (JP); Tomoyuki Ootsuki, Kanagawa (JP)

(73) Assignee: SONY CORPORATION, Tokyo (JP)

(*) Notice: Subject to any disclaimer, the term of this patent is extended or adjusted under 35 U.S.C. 154(b) by 25 days.

This patent is subject to a terminal disclaimer.

(21) Appl. No.: 15/091,135

(22) Filed: Apr. 5, 2016

(65) Prior Publication Data

US 2016/0213244 A1 Jul. 28, 2016

Related U.S. Application Data

(63) Continuation of application No. 13/818,027, filed as application No. PCT/JP2011/069339 on Aug. 26, 2011, now Pat. No. 9,361,667.

(30) Foreign Application Priority Data

Aug. 27, 2010 (JP) .............................. 2010-190353
Nov. 19, 2010 (JP) .............................. 2010-258556

(51) Int. Cl.
*A61B 3/14* (2006.01)
*A61B 3/00* (2006.01)
(Continued)

(52) U.S. Cl.
CPC .............. *A61B 3/0025* (2013.01); *A61B 3/12* (2013.01); *A61B 3/152* (2013.01); *G06T 3/4053* (2013.01);
(Continued)

(58) Field of Classification Search
CPC ......... A61B 3/12; A61B 3/152; A61B 3/0025; A61B 3/102; A61B 3/1241; A61B 5/0066;
(Continued)

(56) References Cited

U.S. PATENT DOCUMENTS 5,125,730 A    6/1992  Taylor
2004/0088026 A1* 5/2004  Chow ....................... A61F 9/08
                                                   607/54

(Continued)

FOREIGN PATENT DOCUMENTS

EP    2131569 A    12/2009
JP    09-253052 A   9/1997
(Continued)

OTHER PUBLICATIONS

European Search Report received for European Patent Application No. 11820057.5, dated Feb. 5, 2016, p. 10.

(Continued)

*Primary Examiner* — Mustak Choudhury
(74) *Attorney, Agent, or Firm* — Chip Law Group

(57) ABSTRACT

The present technology relates to an image processing apparatus and an image processing method capable of suppressing an increase in a load on a subject and obtaining a captured image of the subject with higher image quality. An imaging unit reduces a light amount and performs imaging of the fundus of the eye so as to generate a plurality of fundus images. A biological information alignment processing unit aligns fundus images by using biological information of a subject. A super-resolution processing unit superimposes an aligned input image on a previous super-resolution result image so as to generate a new super-resolution result image. The super-resolution processing unit stores or outputs the super-resolution result image in a (Continued)

storage unit or from an output unit, and supplies the super-resolution result image to a super-resolution result image buffer so as to be stored.

14 Claims, 43 Drawing Sheets

(51) Int. Cl.
| | |
|---|---|
| *G06T 5/00* | (2006.01) |
| *G06T 5/50* | (2006.01) |
| *G06T 3/40* | (2006.01) |
| *A61B 3/15* | (2006.01) |
| *H04N 1/387* | (2006.01) |
| *A61B 3/12* | (2006.01) |

(52) U.S. Cl.
CPC .............. *G06T 5/001* (2013.01); *G06T 5/002* (2013.01); *G06T 5/50* (2013.01); *H04N 1/387* (2013.01); *G06T 2207/20208* (2013.01); *H04N 2201/0414* (2013.01)

(58) Field of Classification Search
CPC ......... A61B 5/748; A61B 3/10; A61B 3/1225; A61B 3/0008; A61B 3/024; A61B 3/085; A61B 3/112; A61B 3/113; A61B 3/145; A61B 3/241; A61B 3/1208; G06T 3/4053; G06T 5/001; G06T 5/002; G06T 5/50; G06T 7/33; G06T 15/08; G06T 19/00; H04N 1/387; G06F 19/321; G01N 21/4795; A61F 9/08; G02B 21/0028; G02B 21/0064; G02B 26/10
USPC ......... 351/205, 206, 211, 221; 345/418–420; 600/504
See application file for complete search history.

(56) References Cited

U.S. PATENT DOCUMENTS

| | | | |
|---|---|---|---|
| 2006/0146284 A1* | 7/2006 | Collins | ................ A61B 3/1208 351/215 |
| 2008/0100612 A1 | 5/2008 | Dastmalchi et al. | |

FOREIGN PATENT DOCUMENTS

| | | |
|---|---|---|
| JP | 2003-299620 A | 10/2003 |
| JP | 2009-502220 A | 1/2009 |

OTHER PUBLICATIONS

Office Action Received for Japanese Patent Application No. 2012-530745, dated May 10, 2016, 6 pages of Office Action.

* cited by examiner

[FIG. 1]
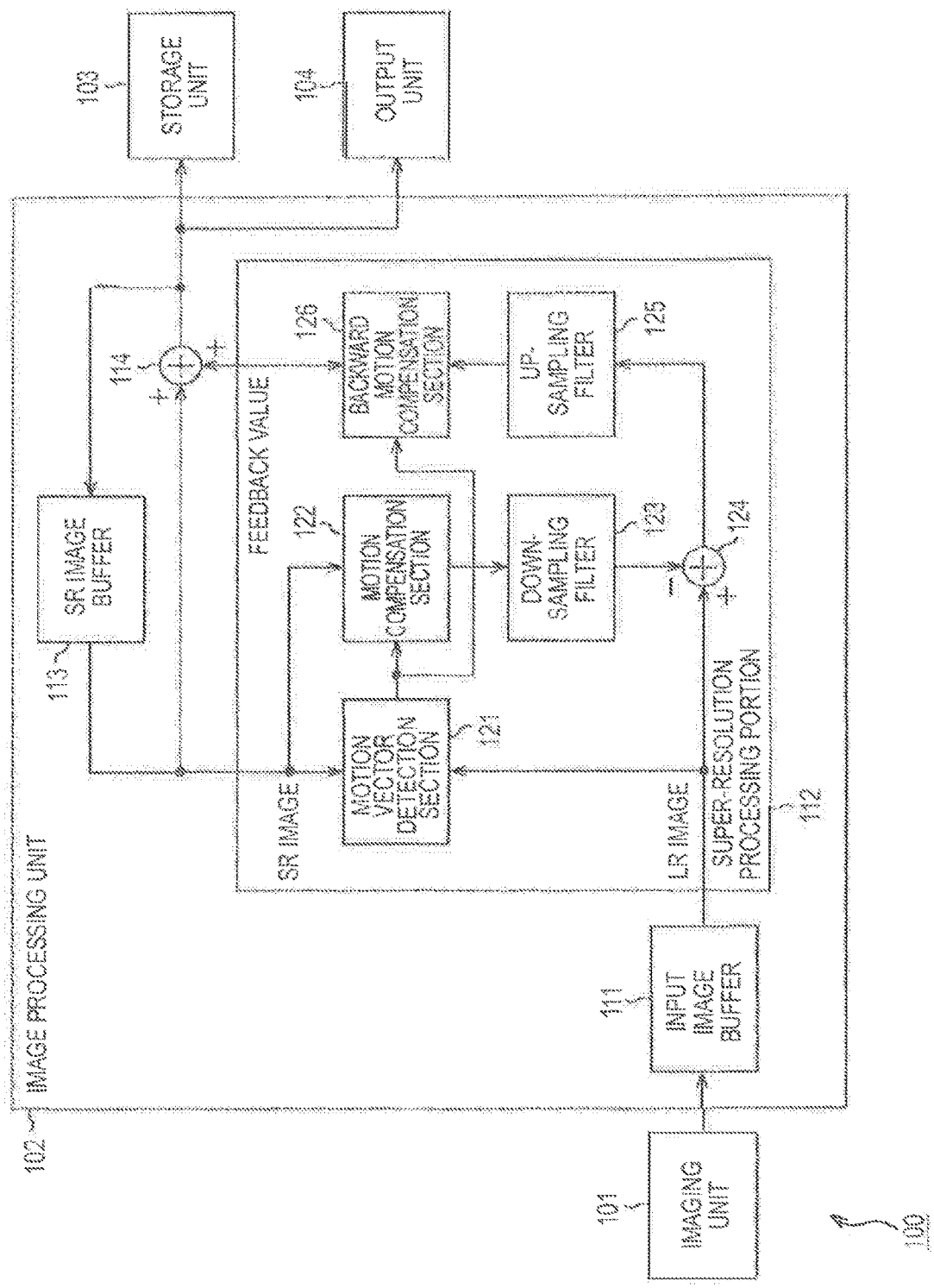

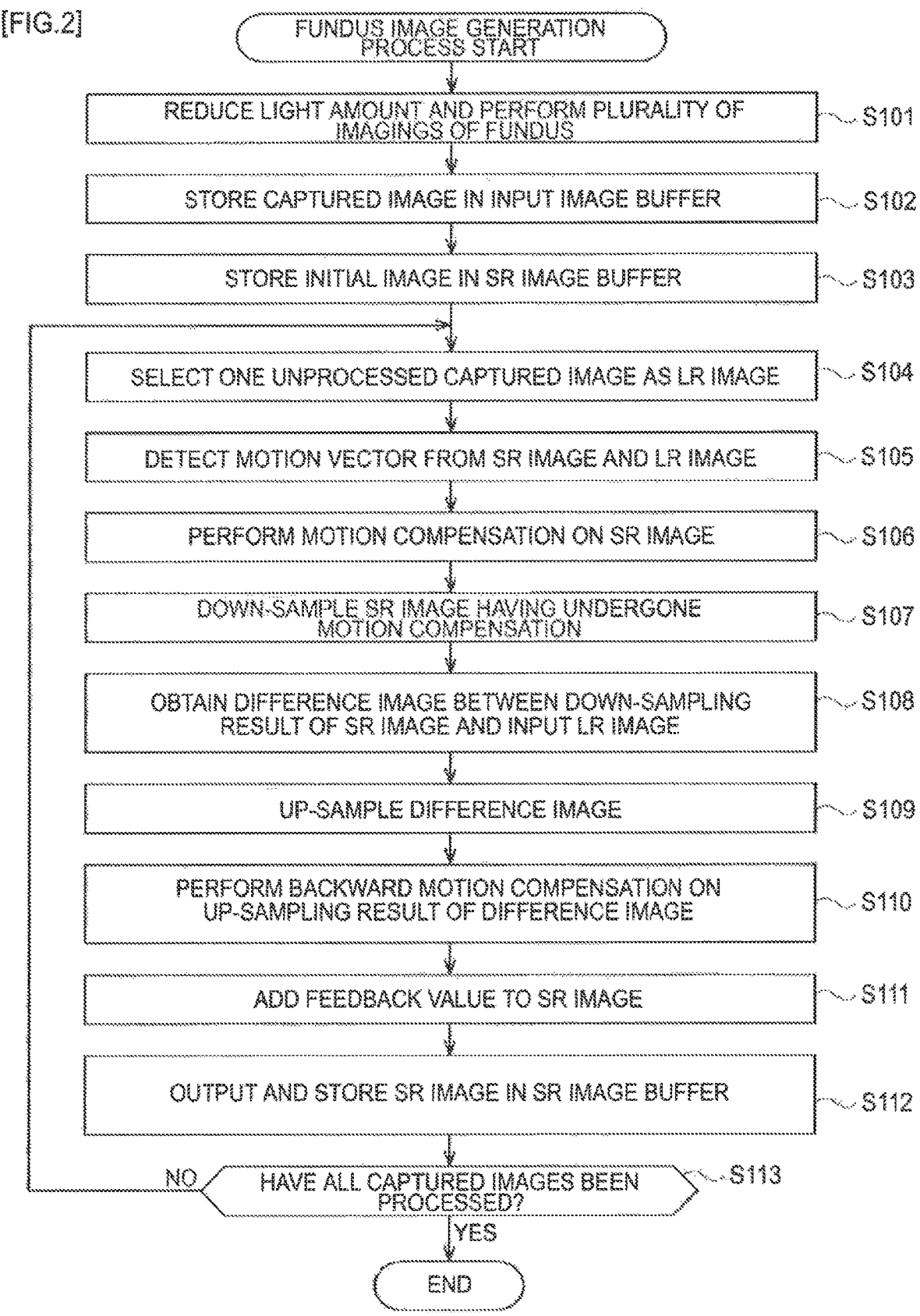

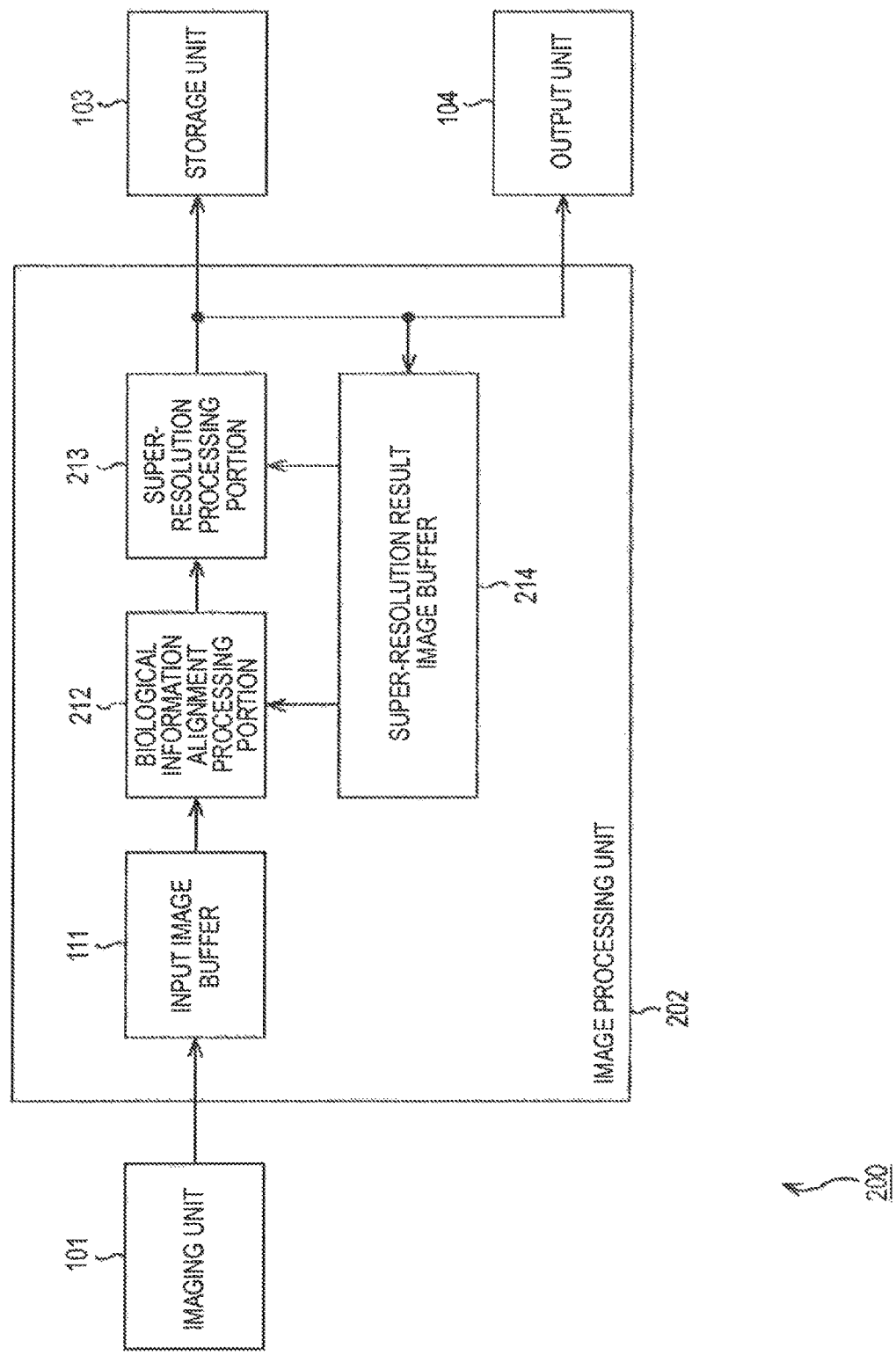
[FIG. 3]

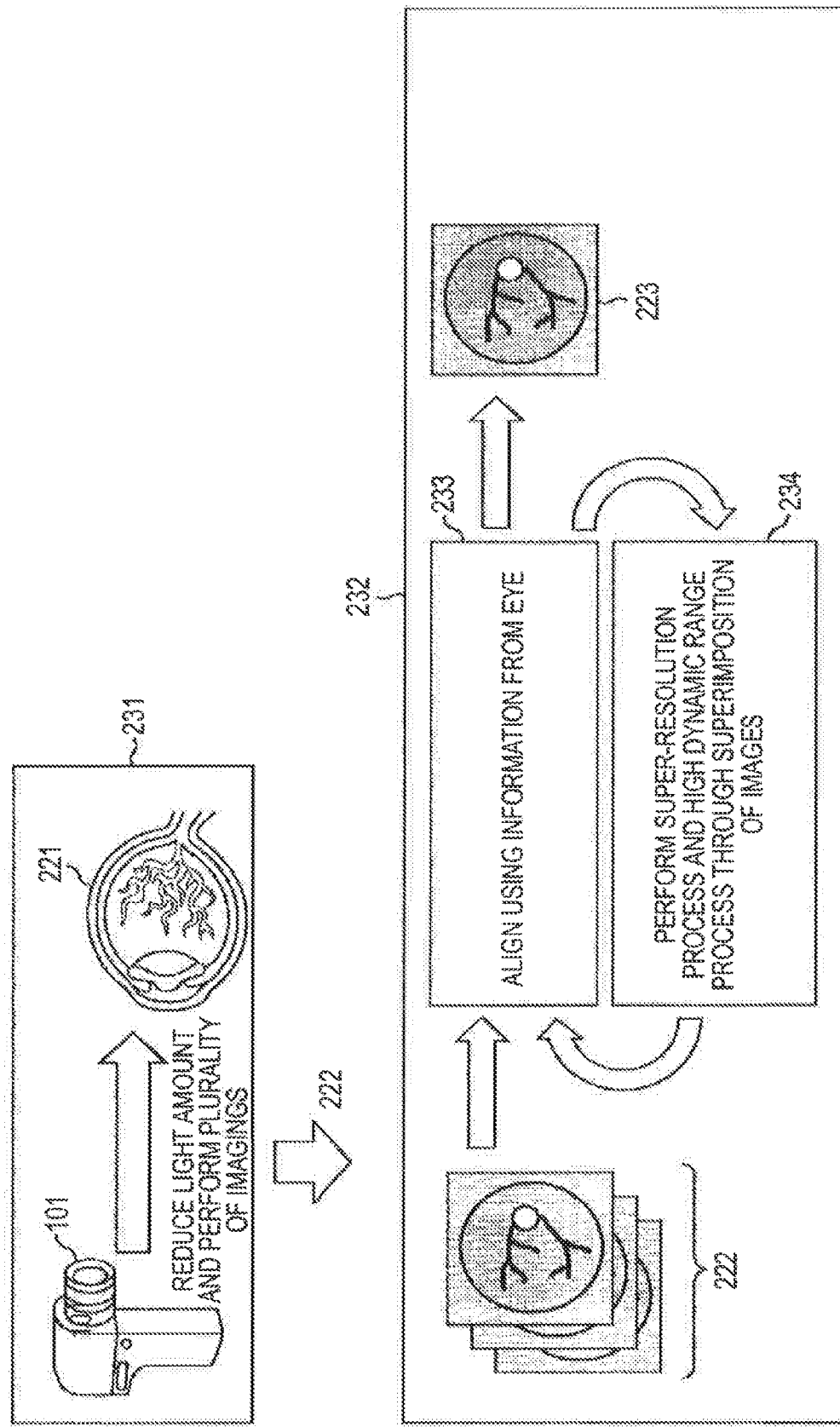

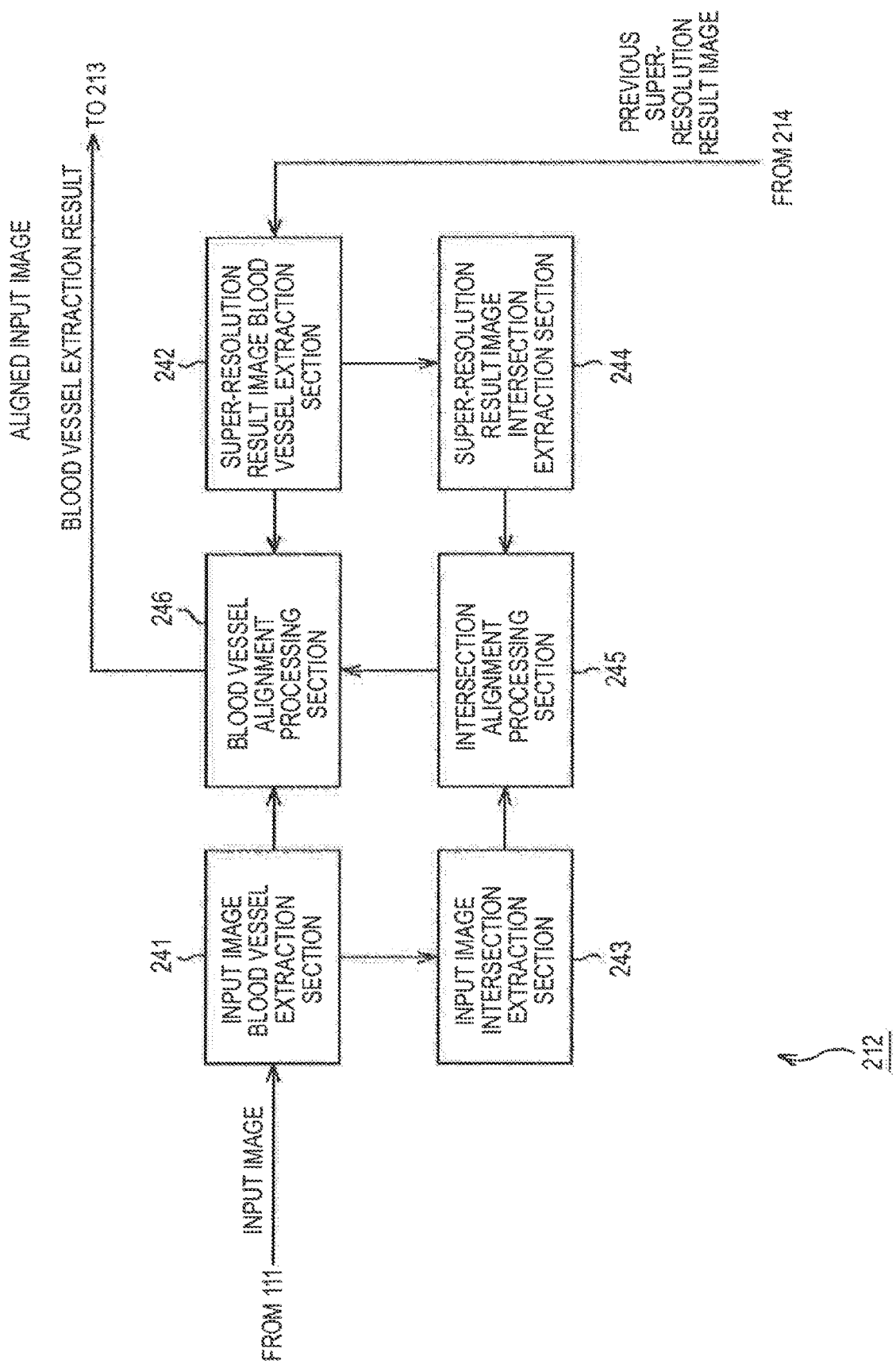
[FIG. 5]

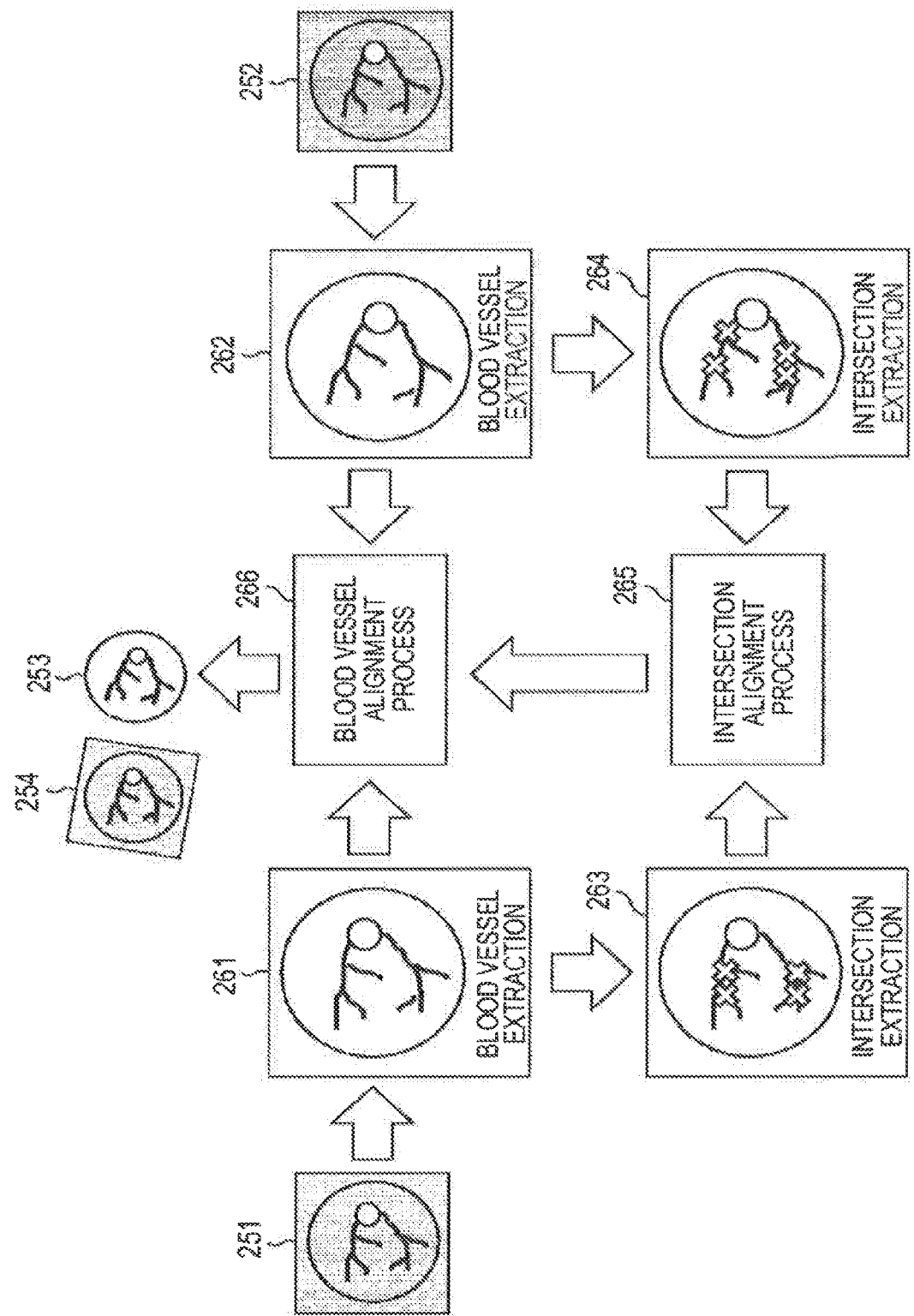
[FIG. 6]

[FIG.7]
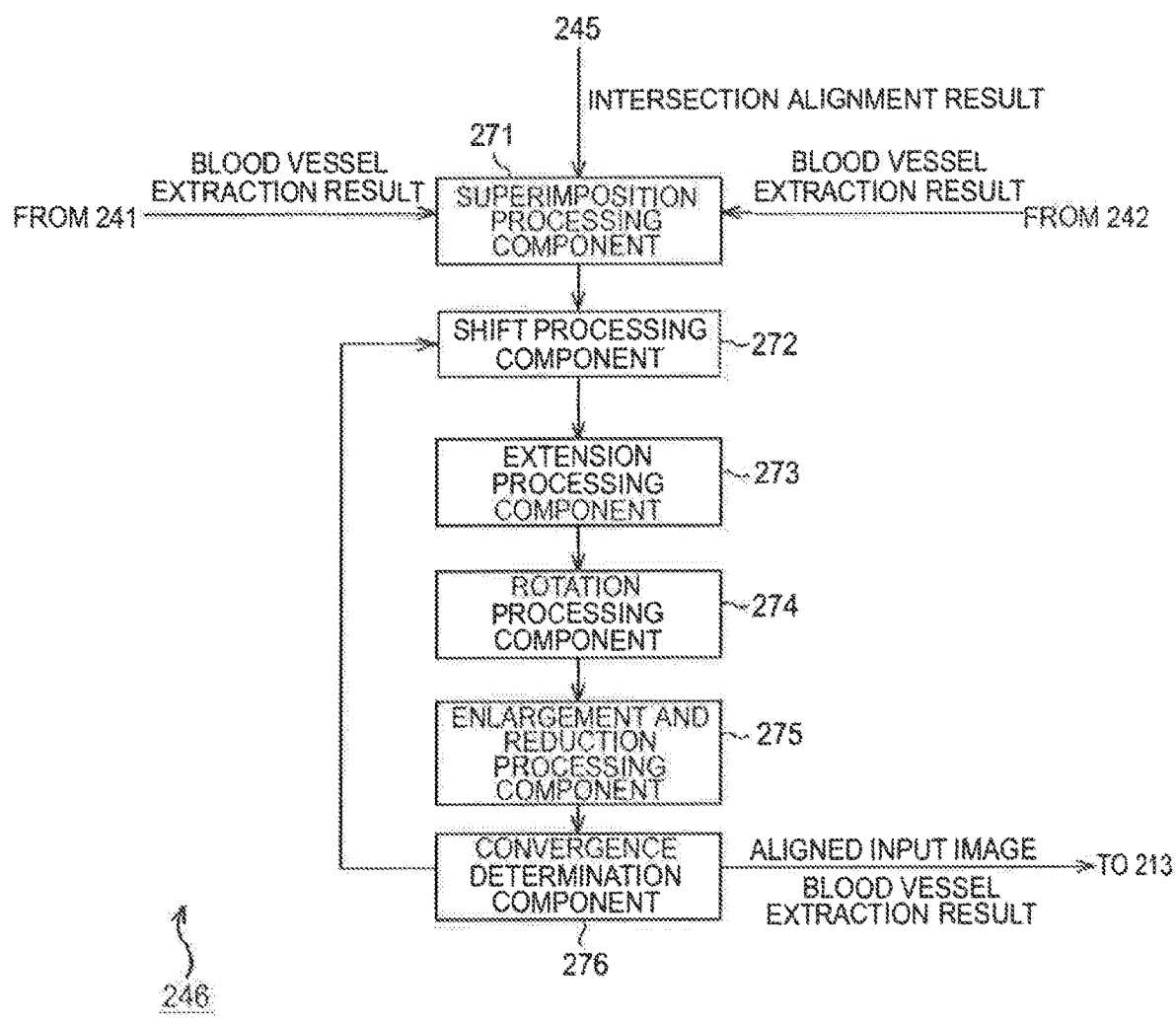

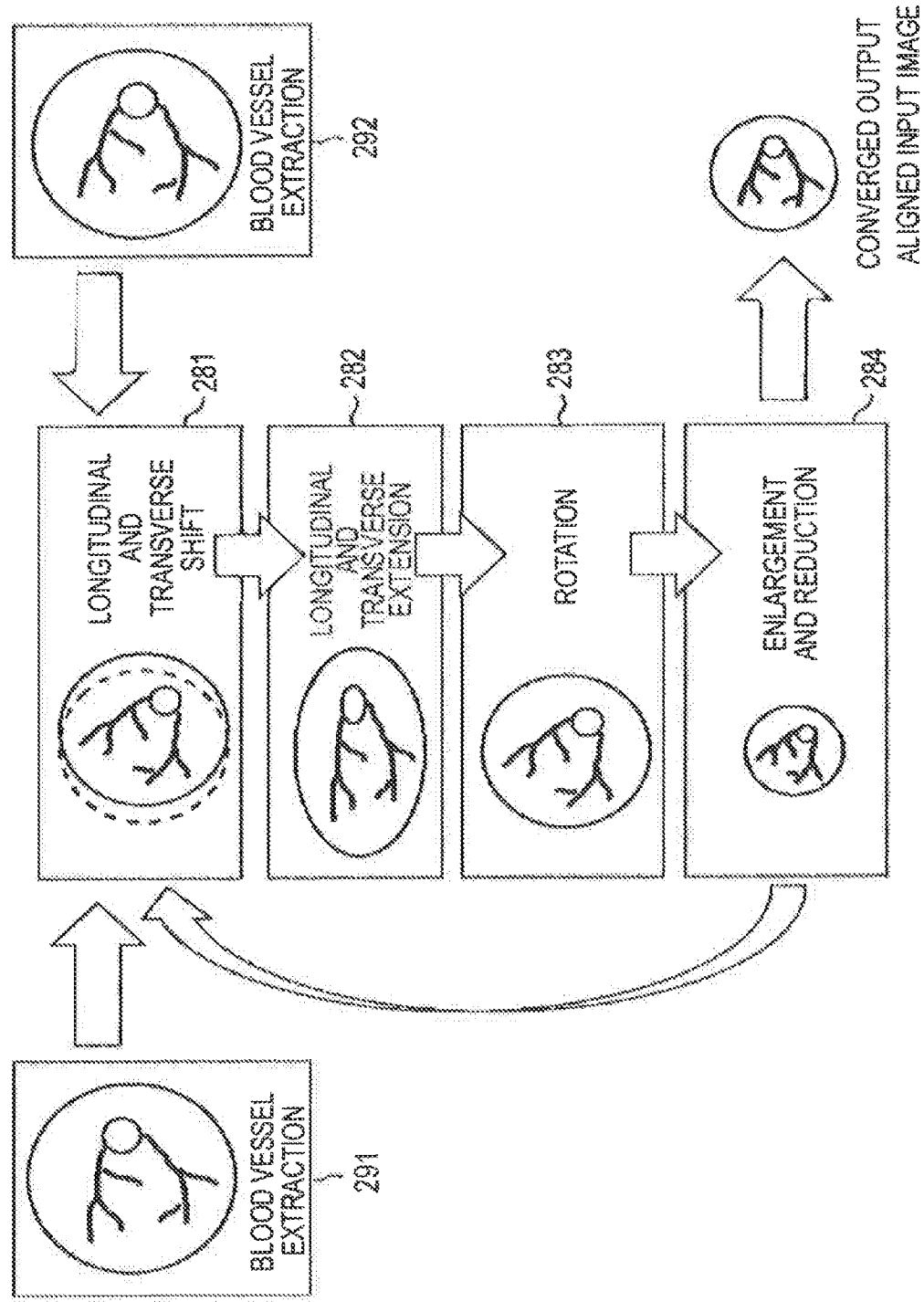

[FIG. 9]
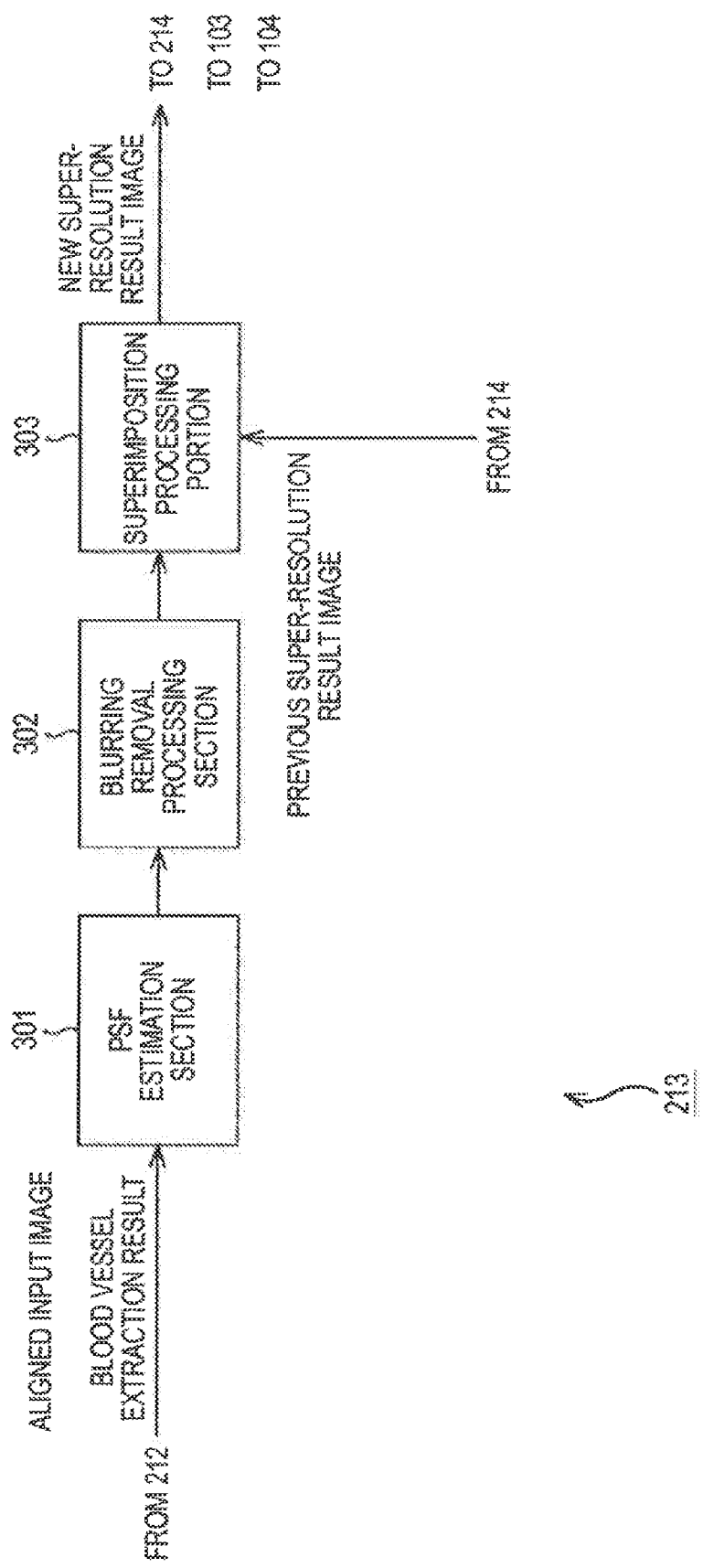

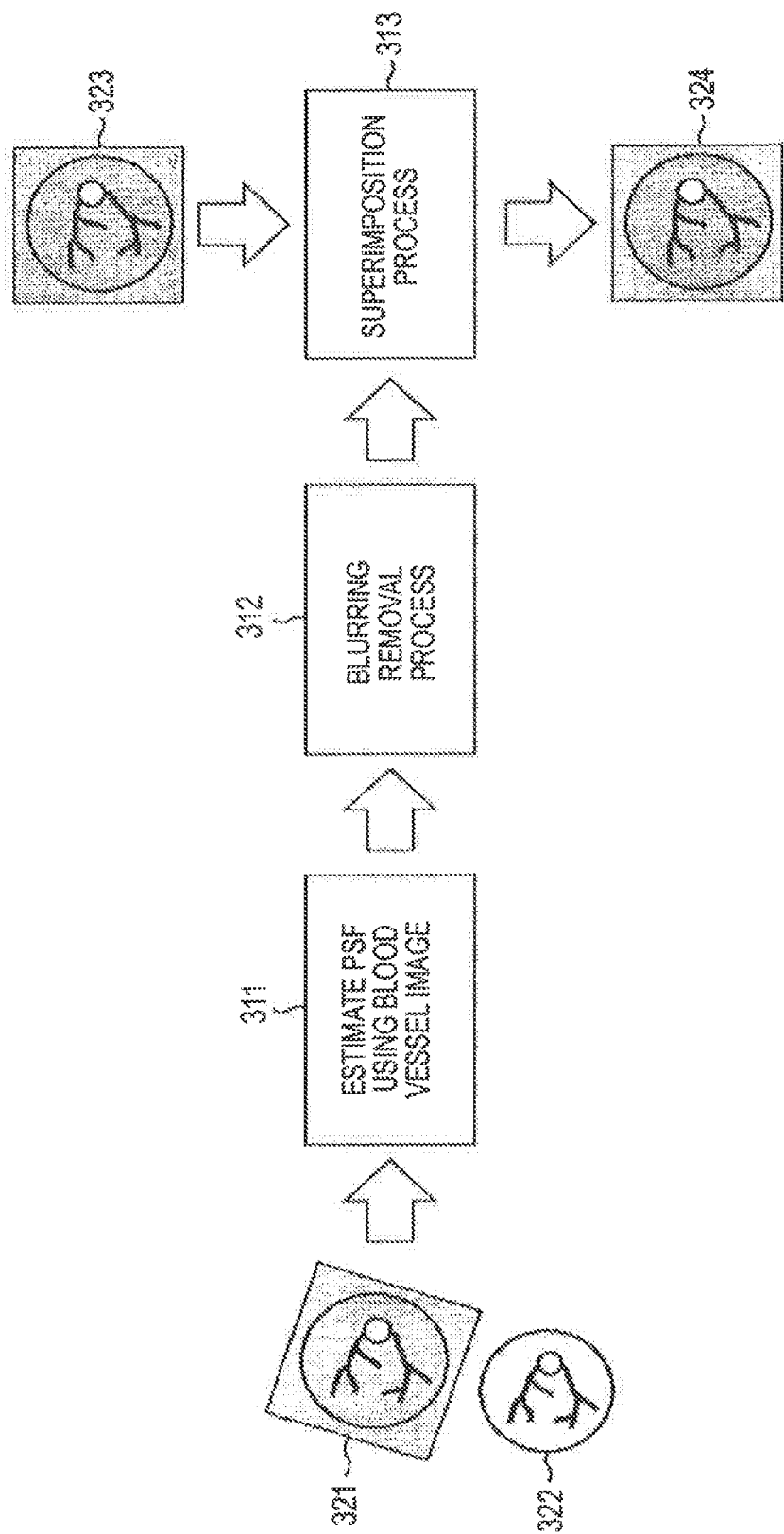
[FIG. 10]

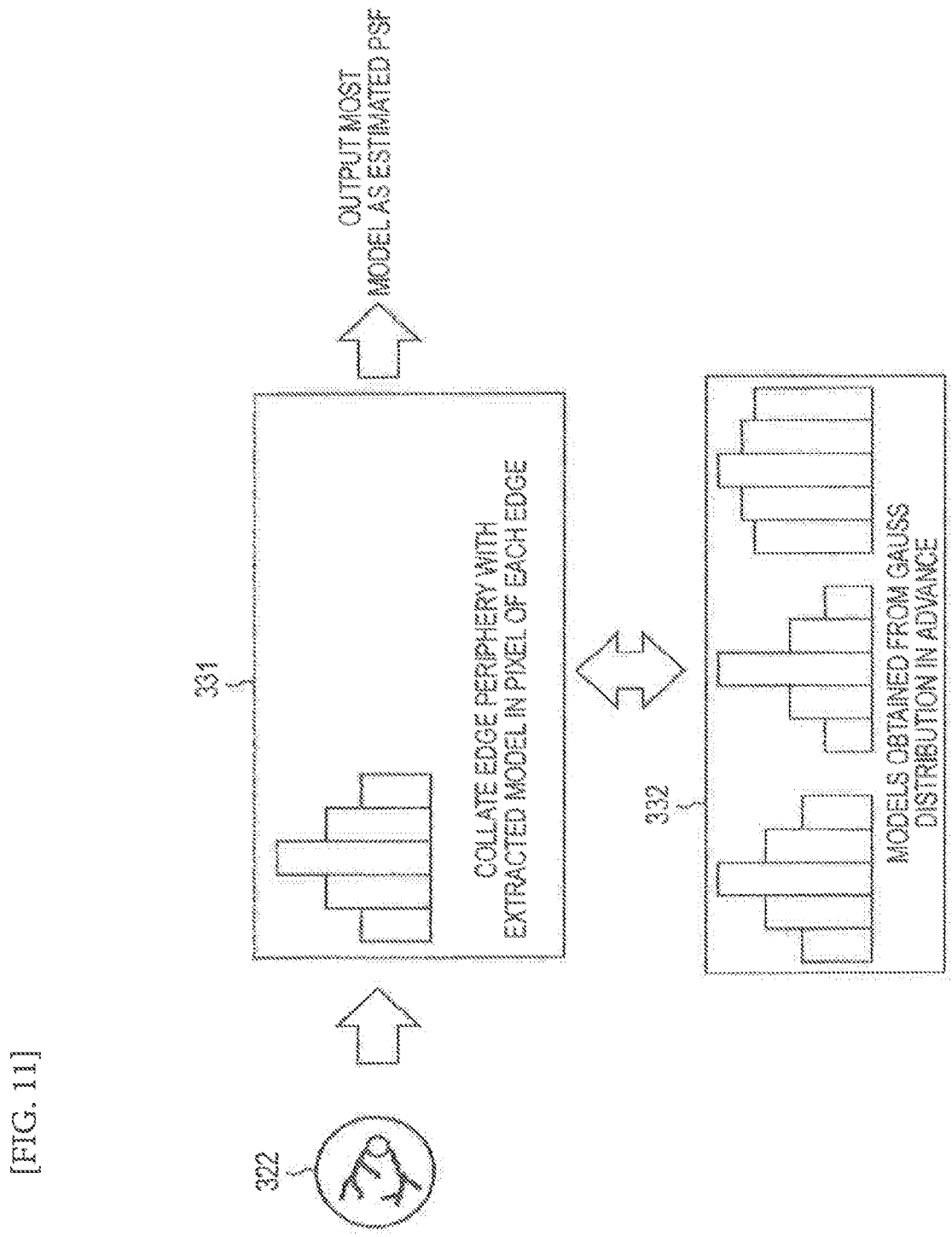
[FIG. 11]

[FIG.12]
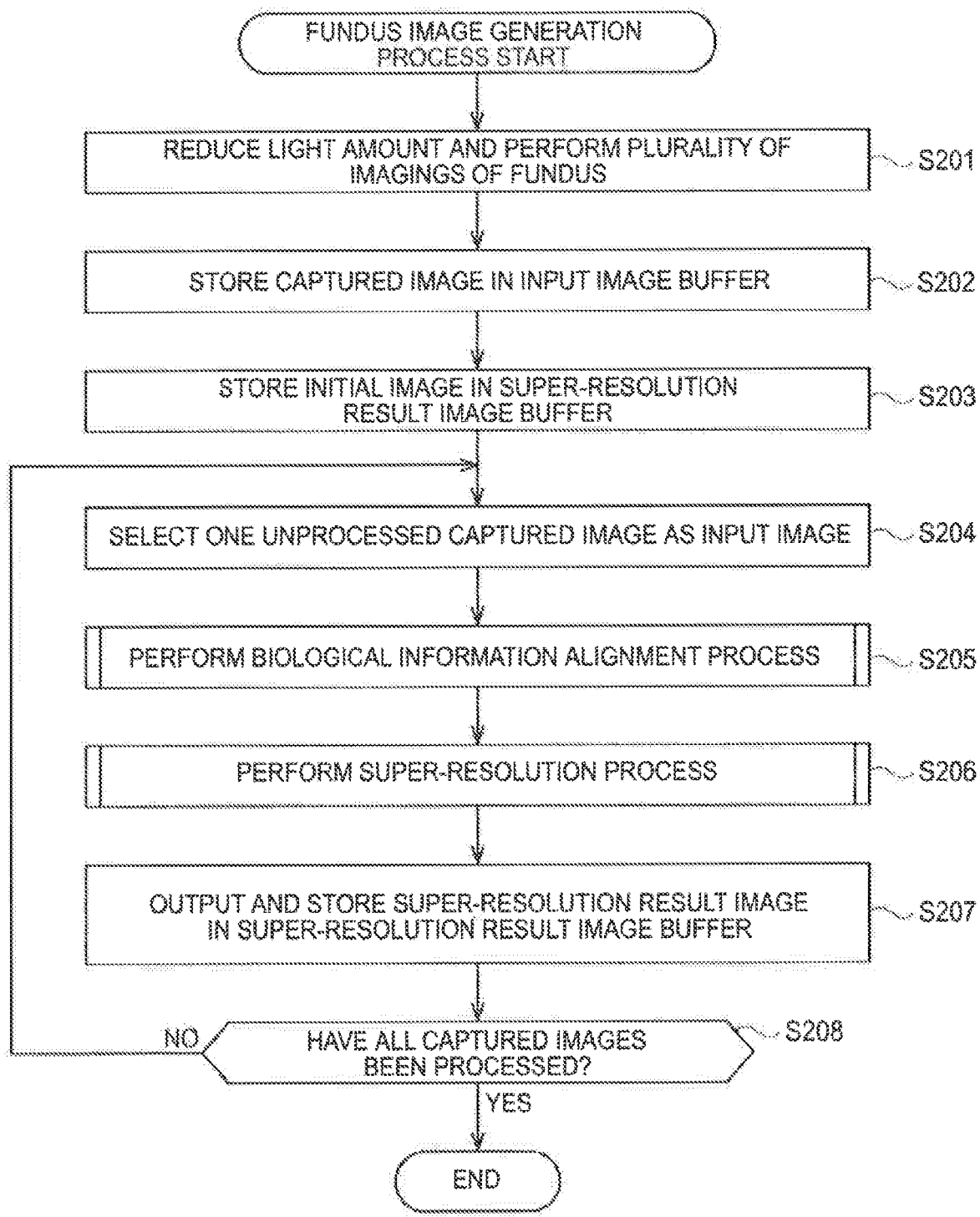

[FIG.13]
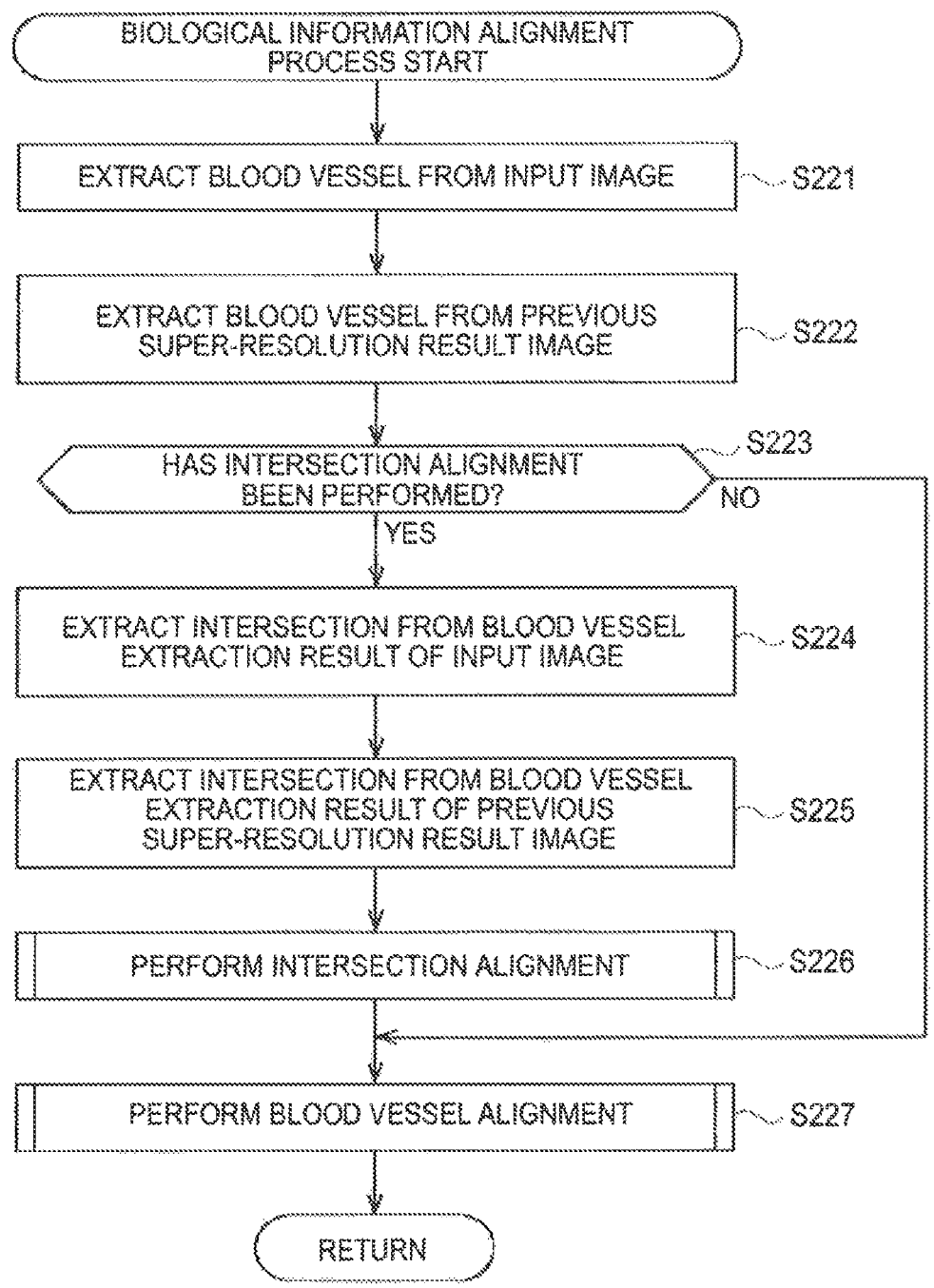

[FIG.14]
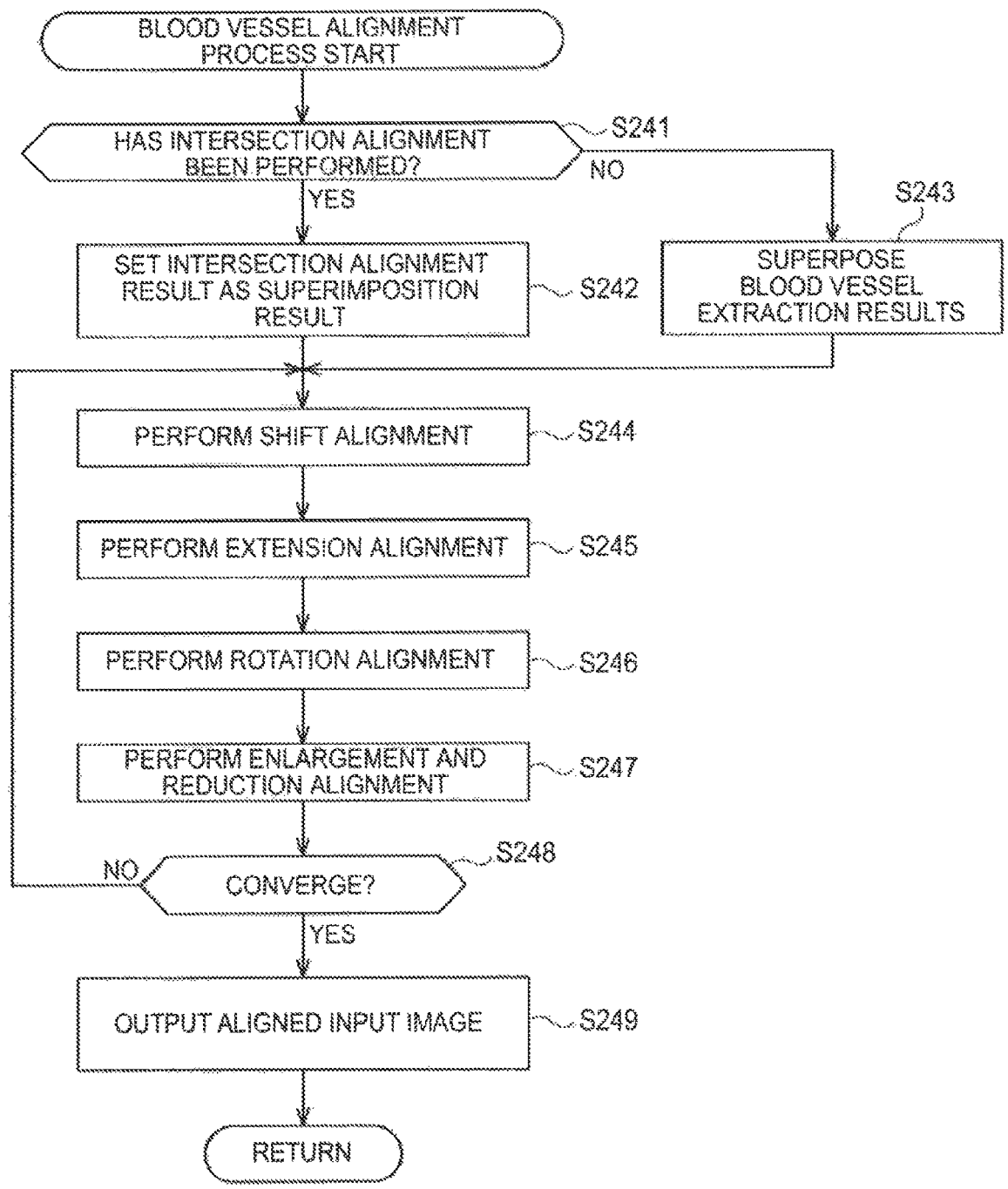

[FIG.15]
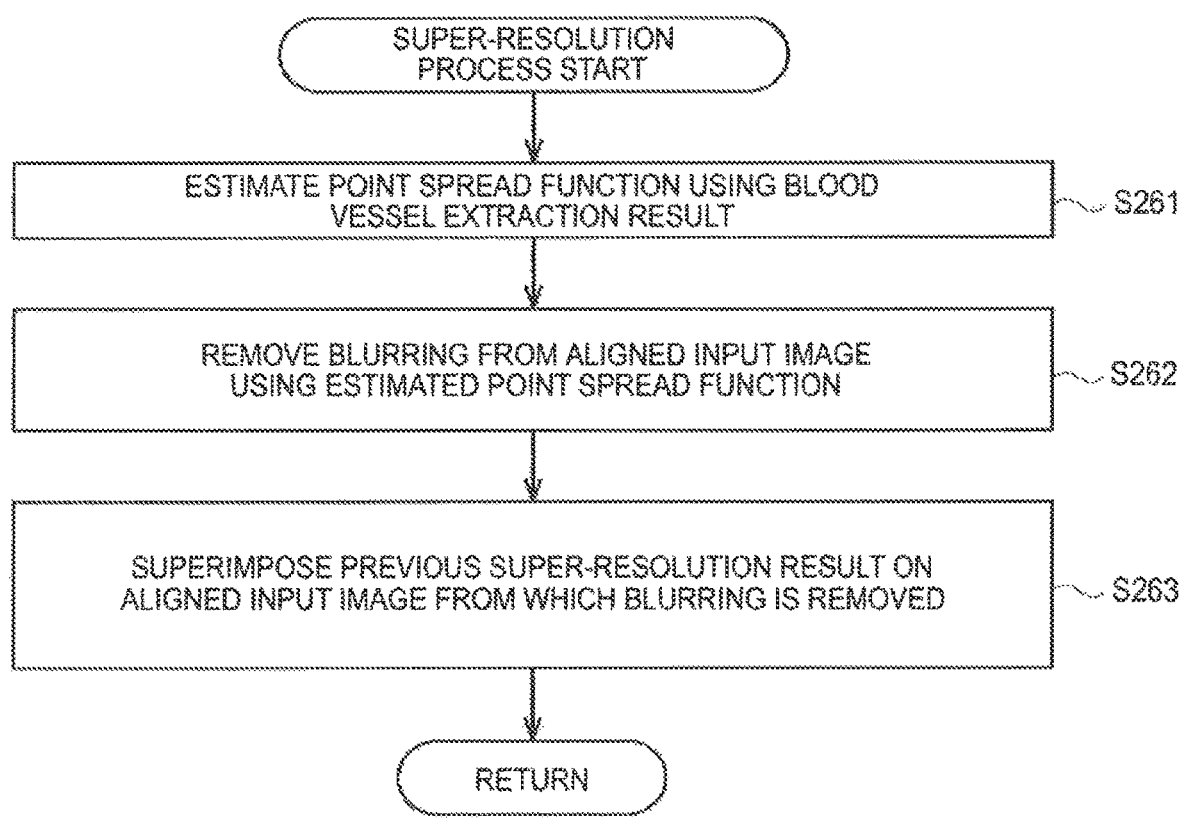

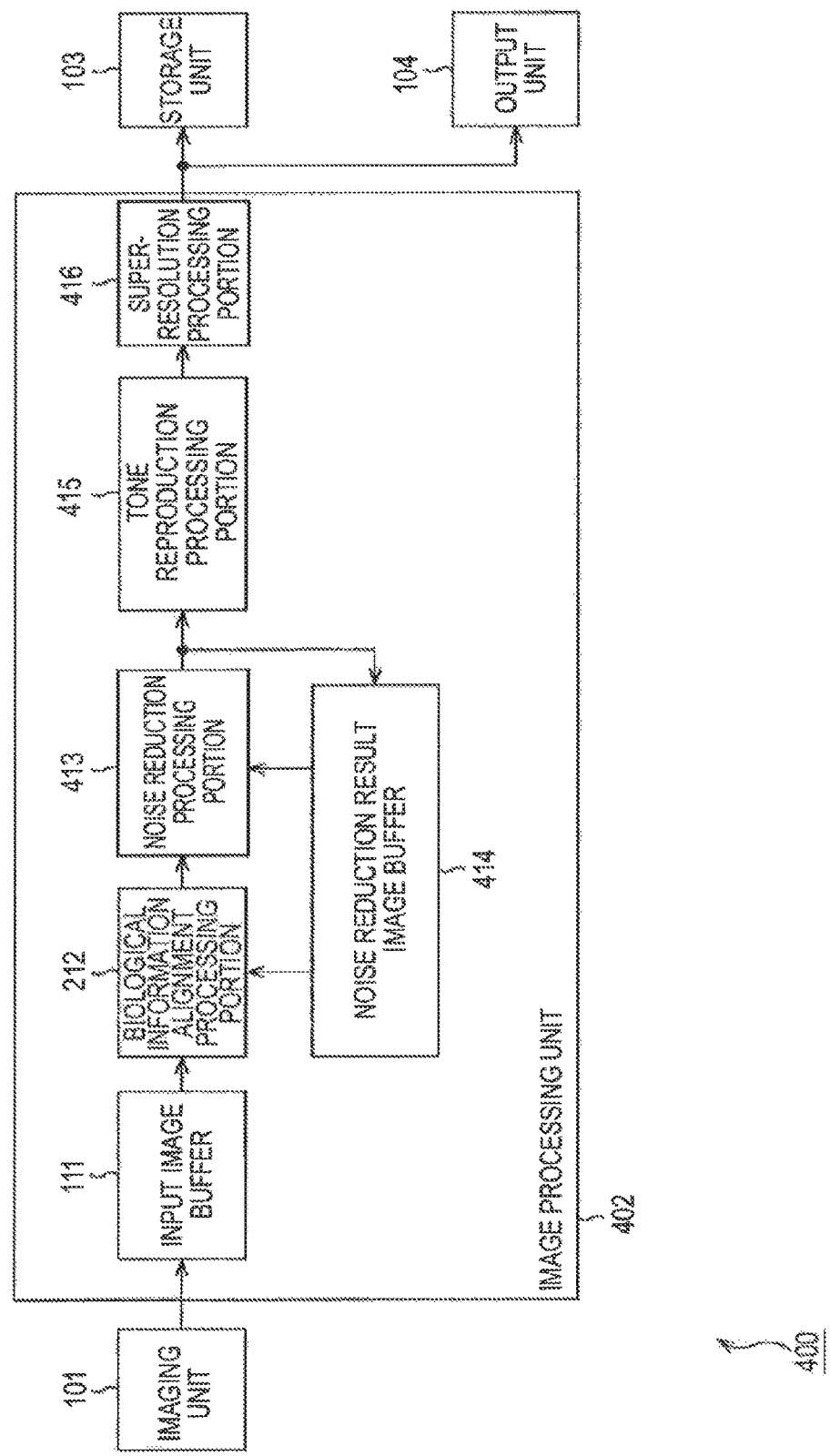
[FIG. 16]

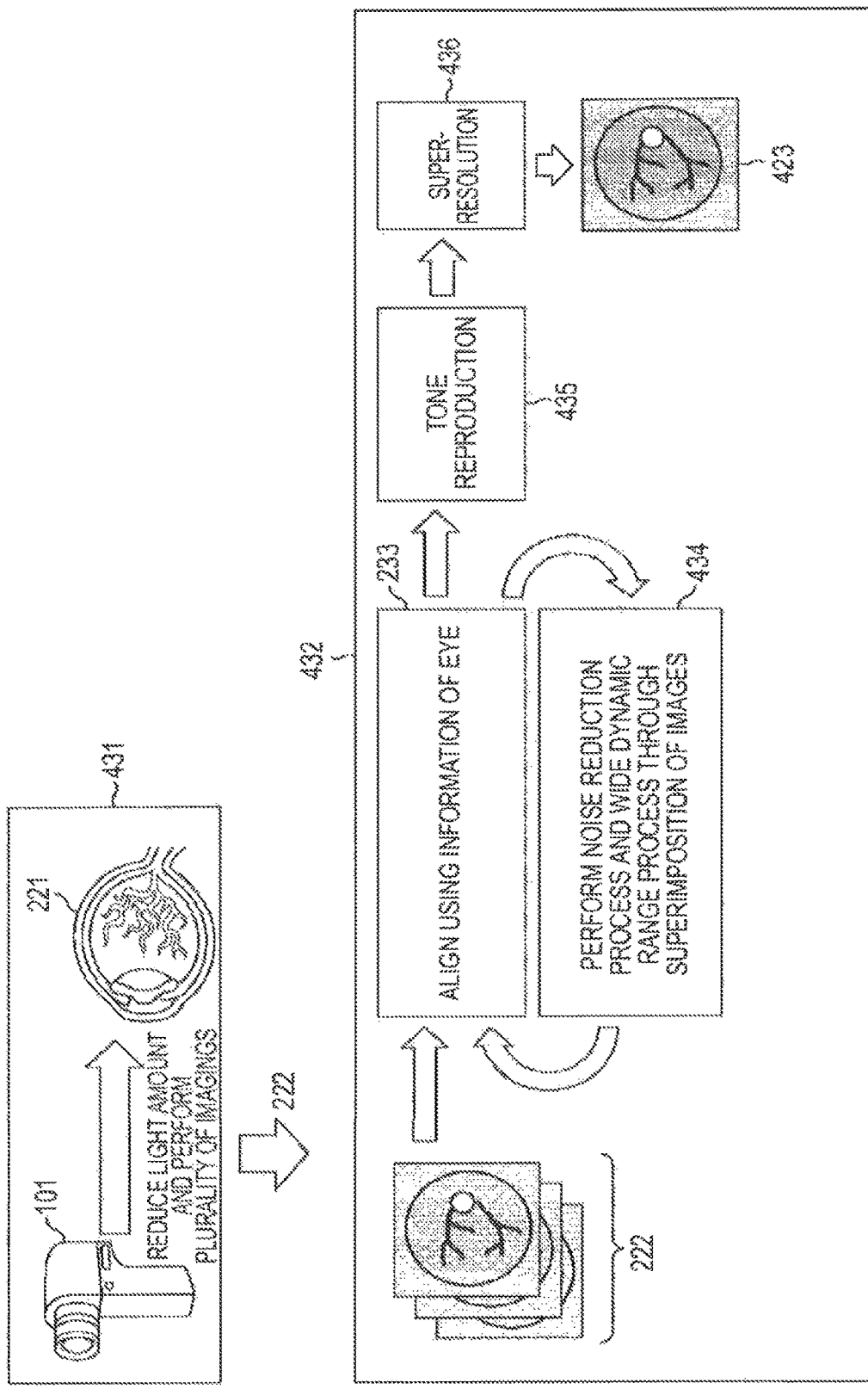

[FIG.18]
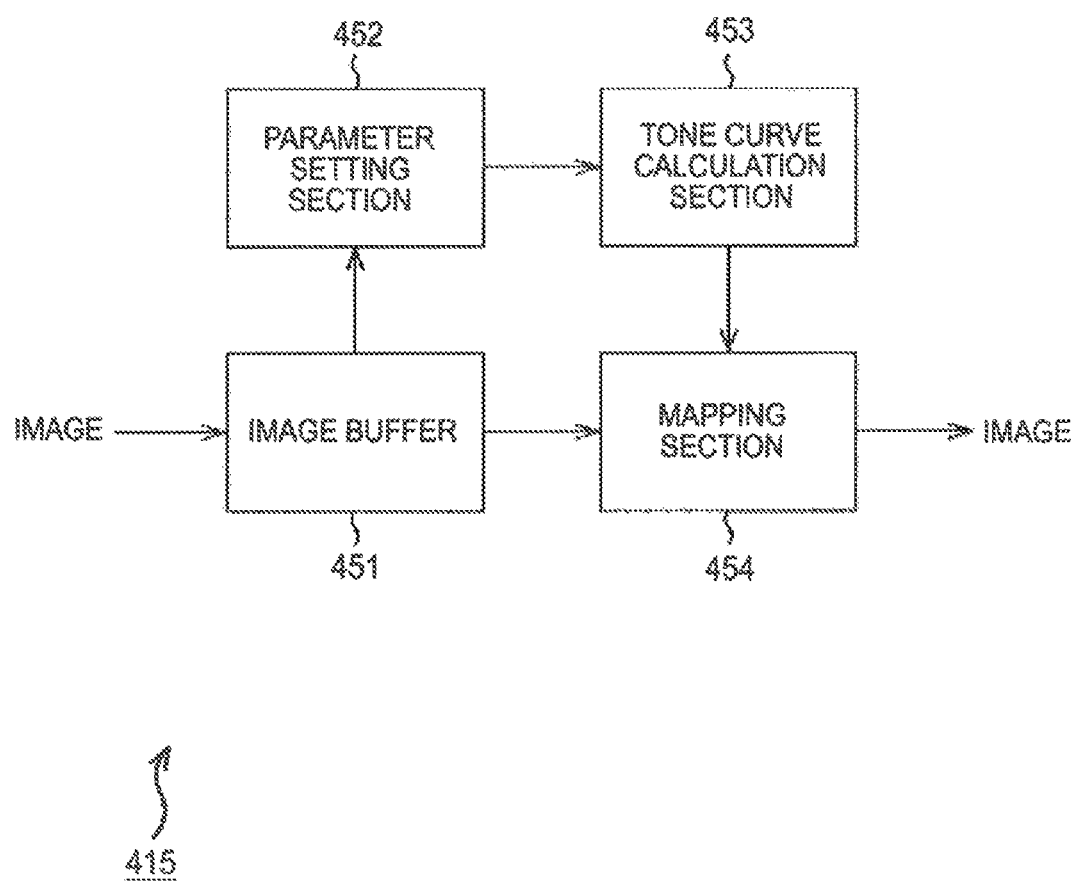

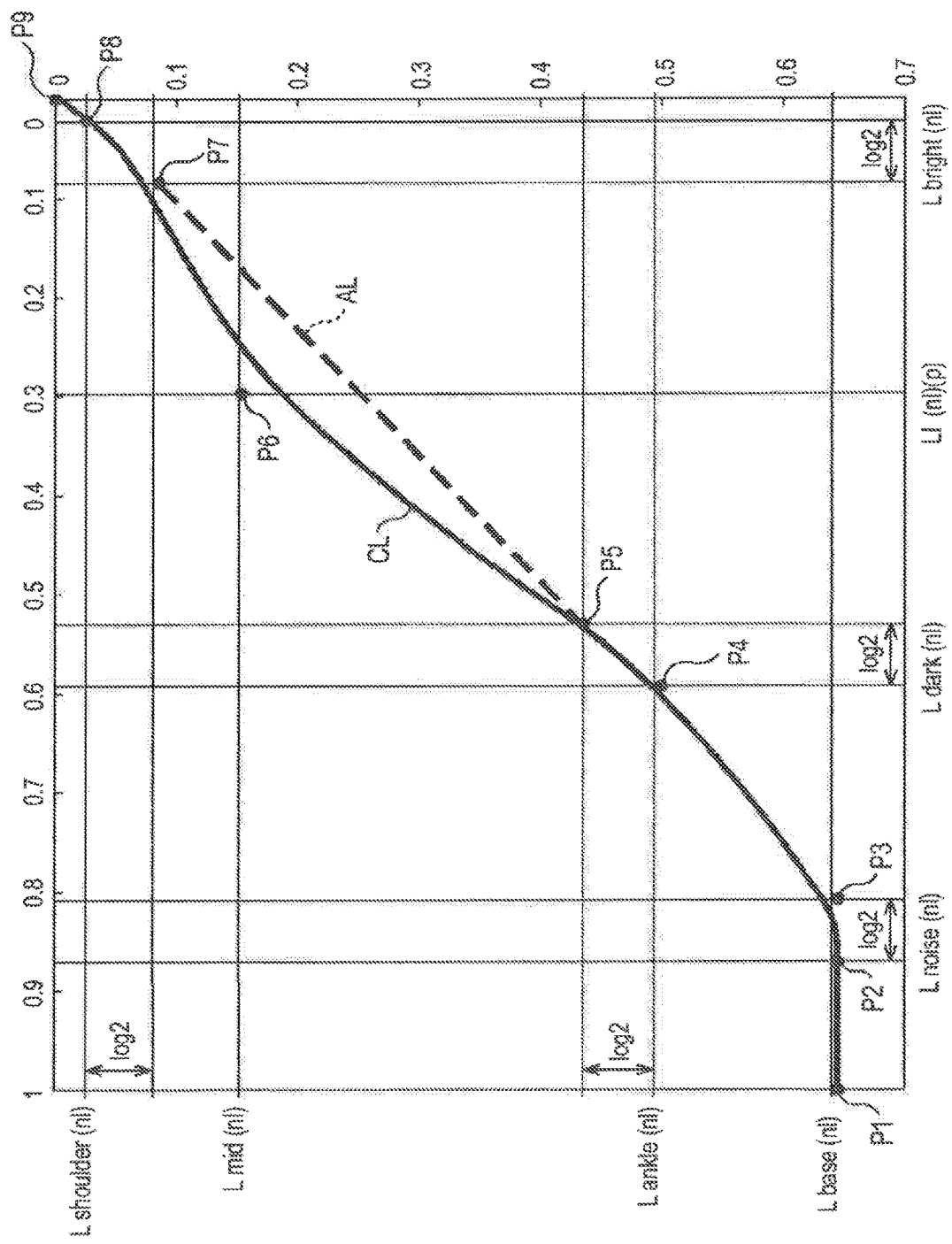
[FIG. 19]

[FIG. 20]
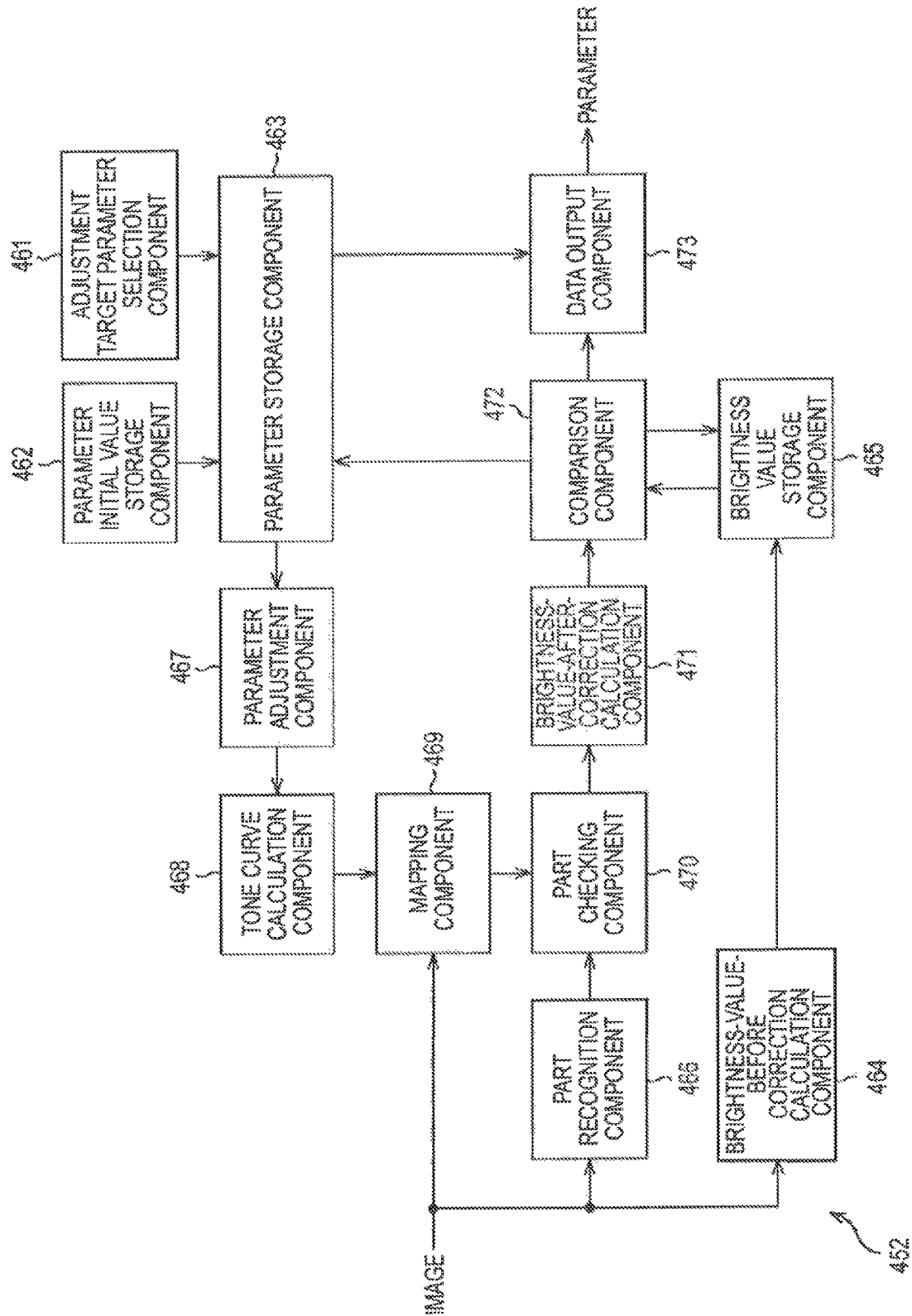

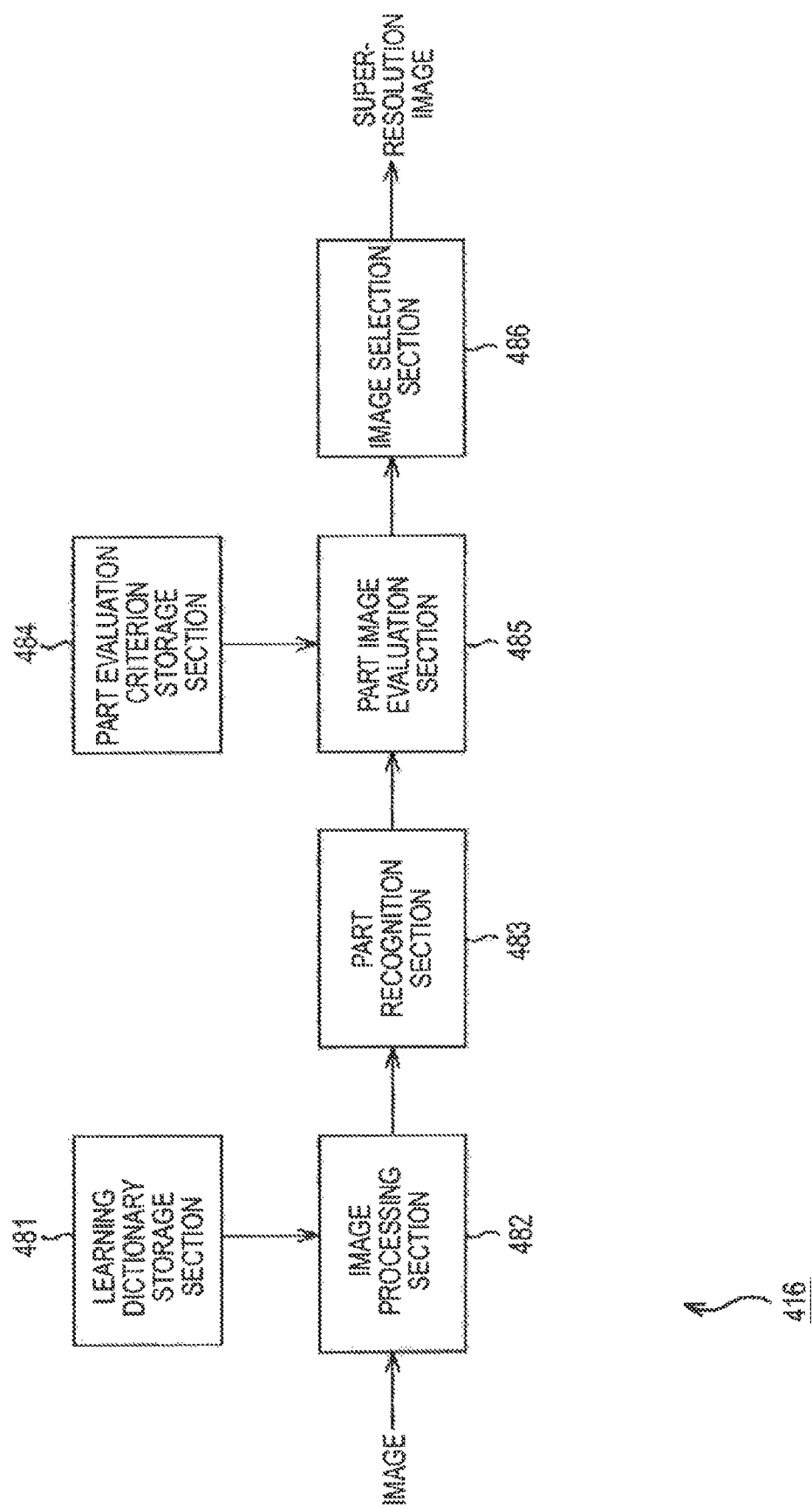

[FIG.22]
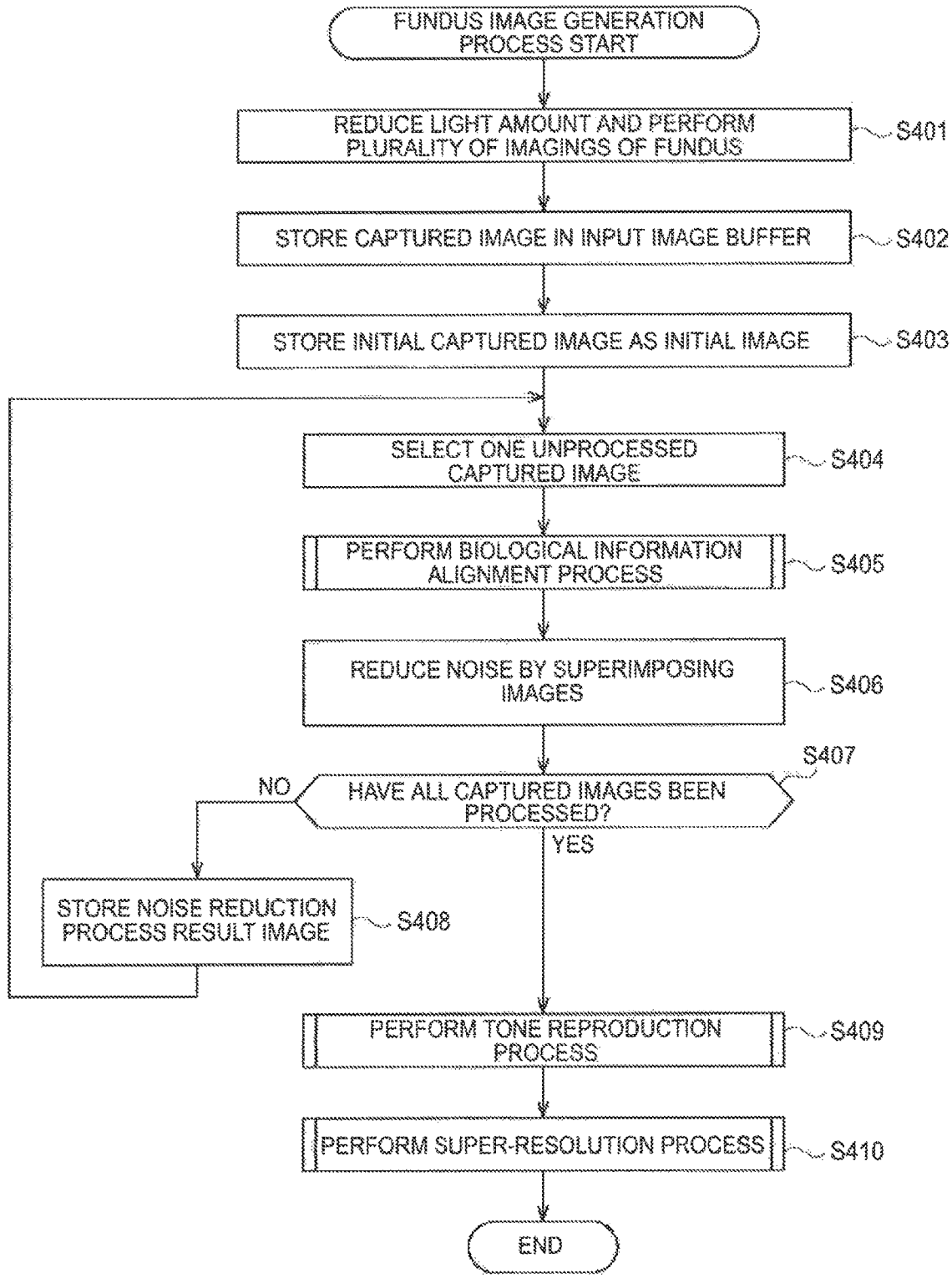

[FIG.23]
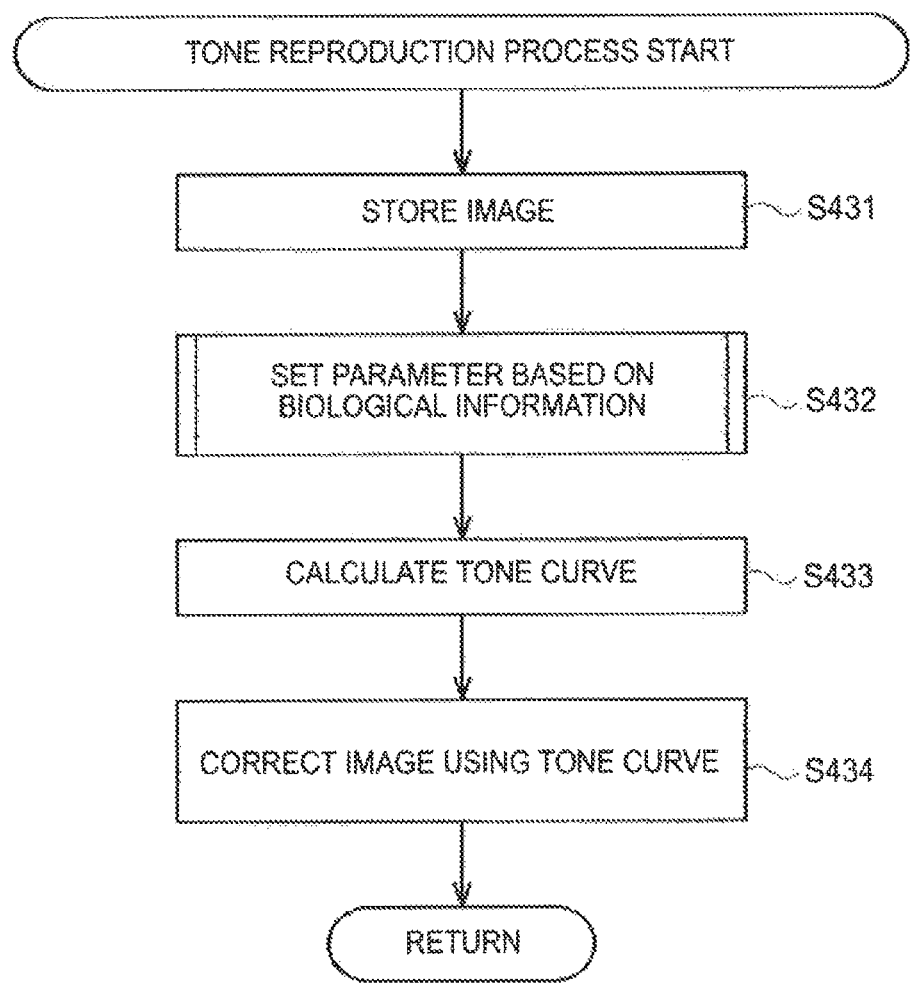

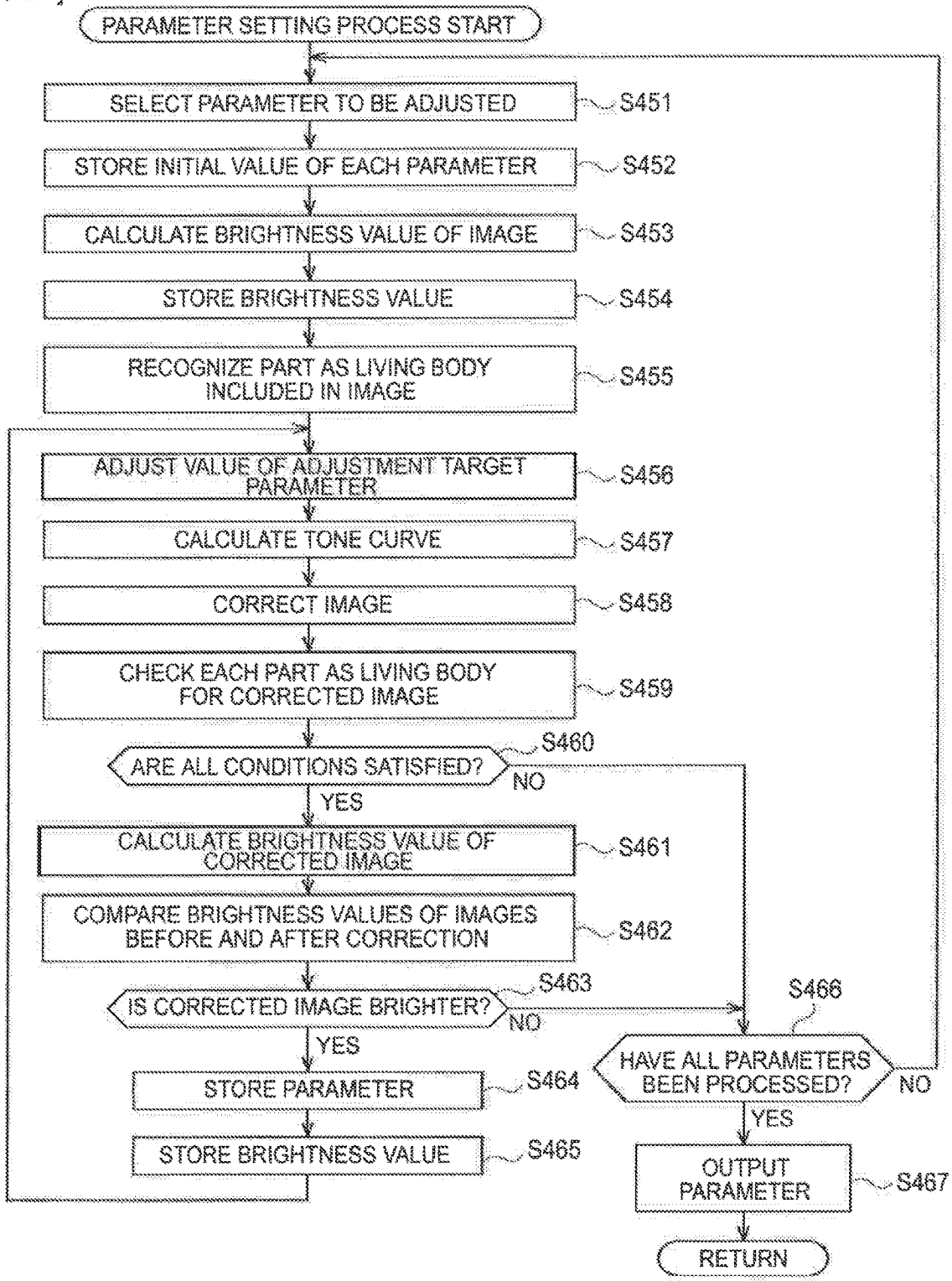

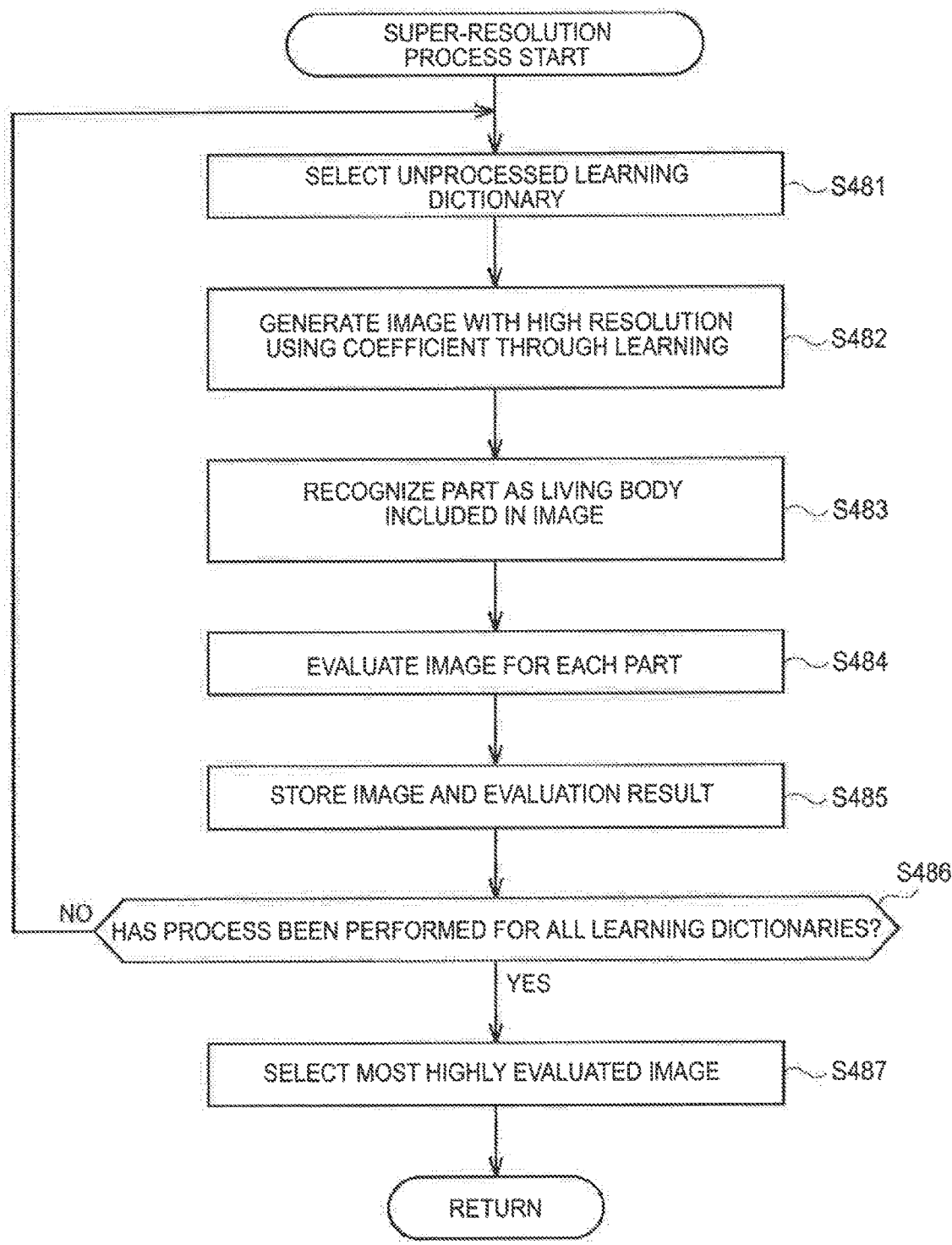

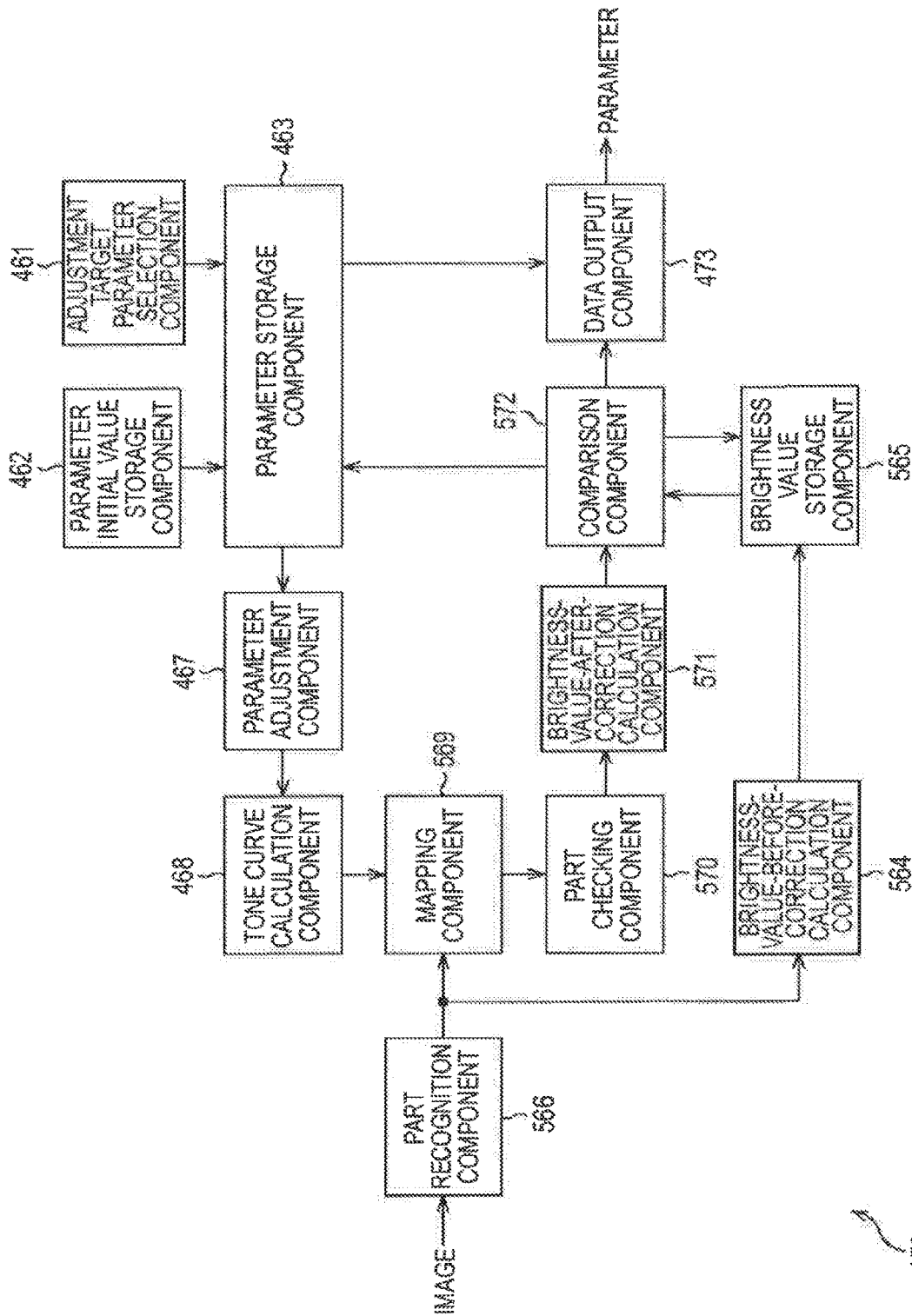
[FIG. 26]

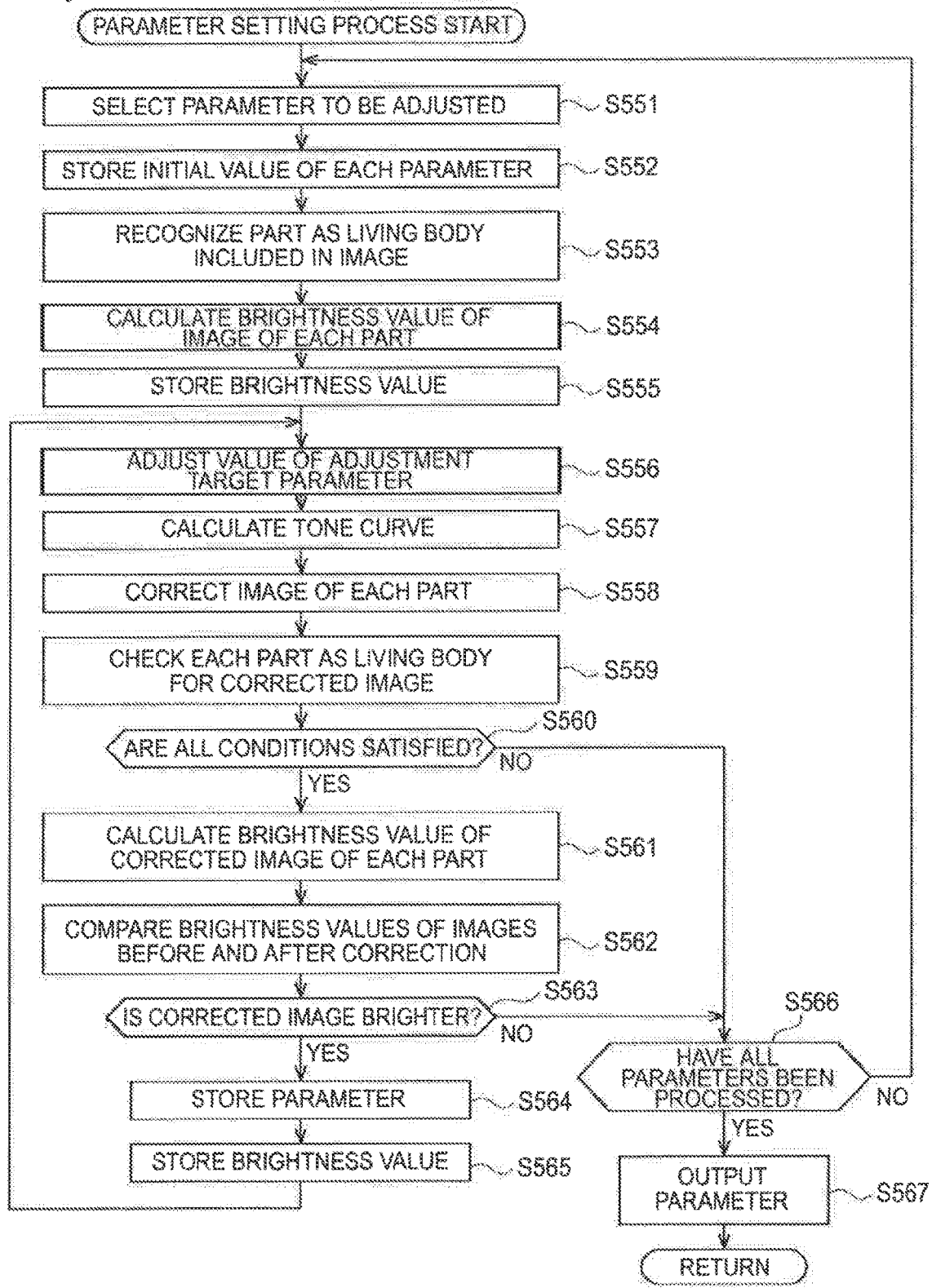

[FIG.28]
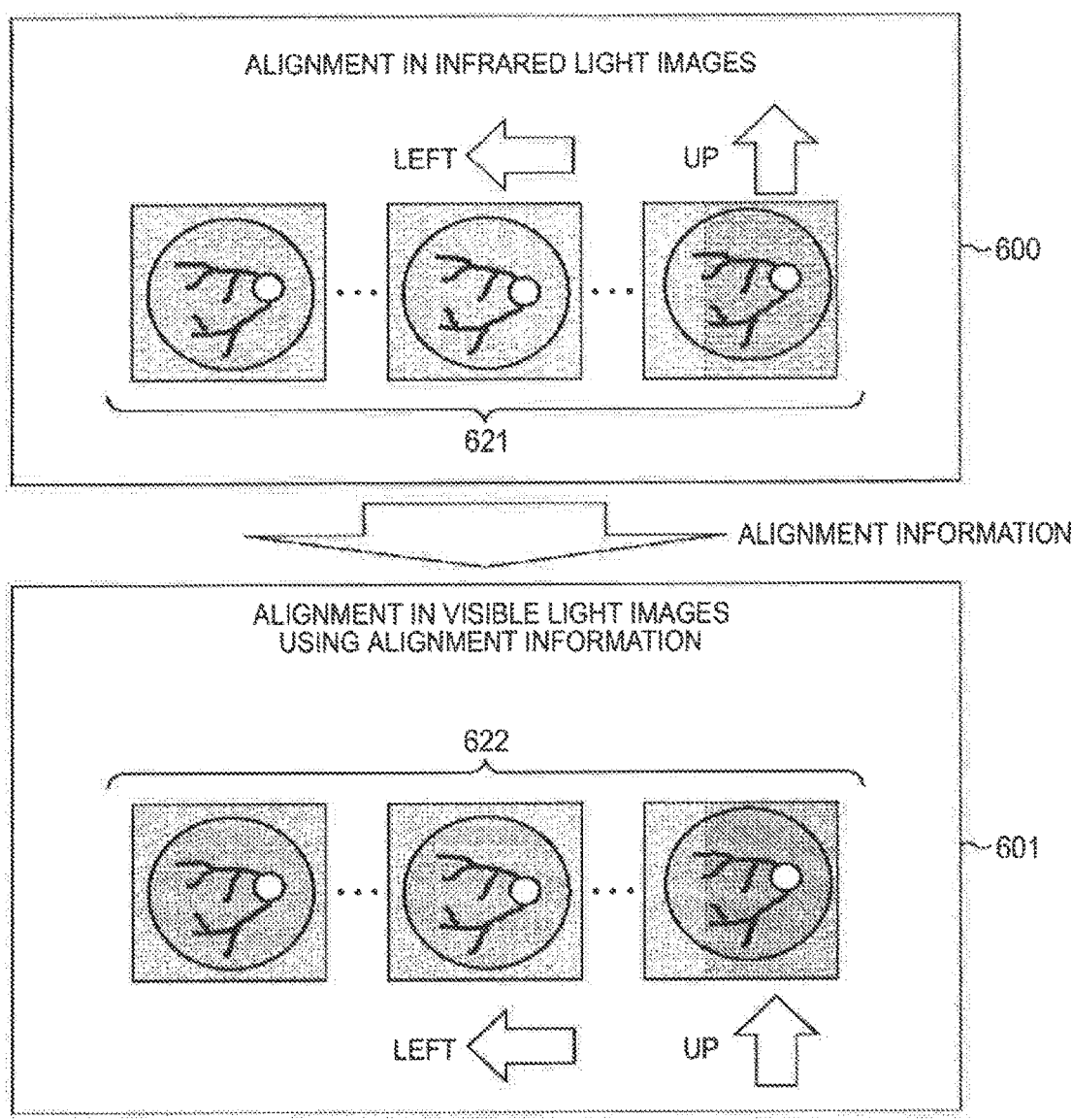

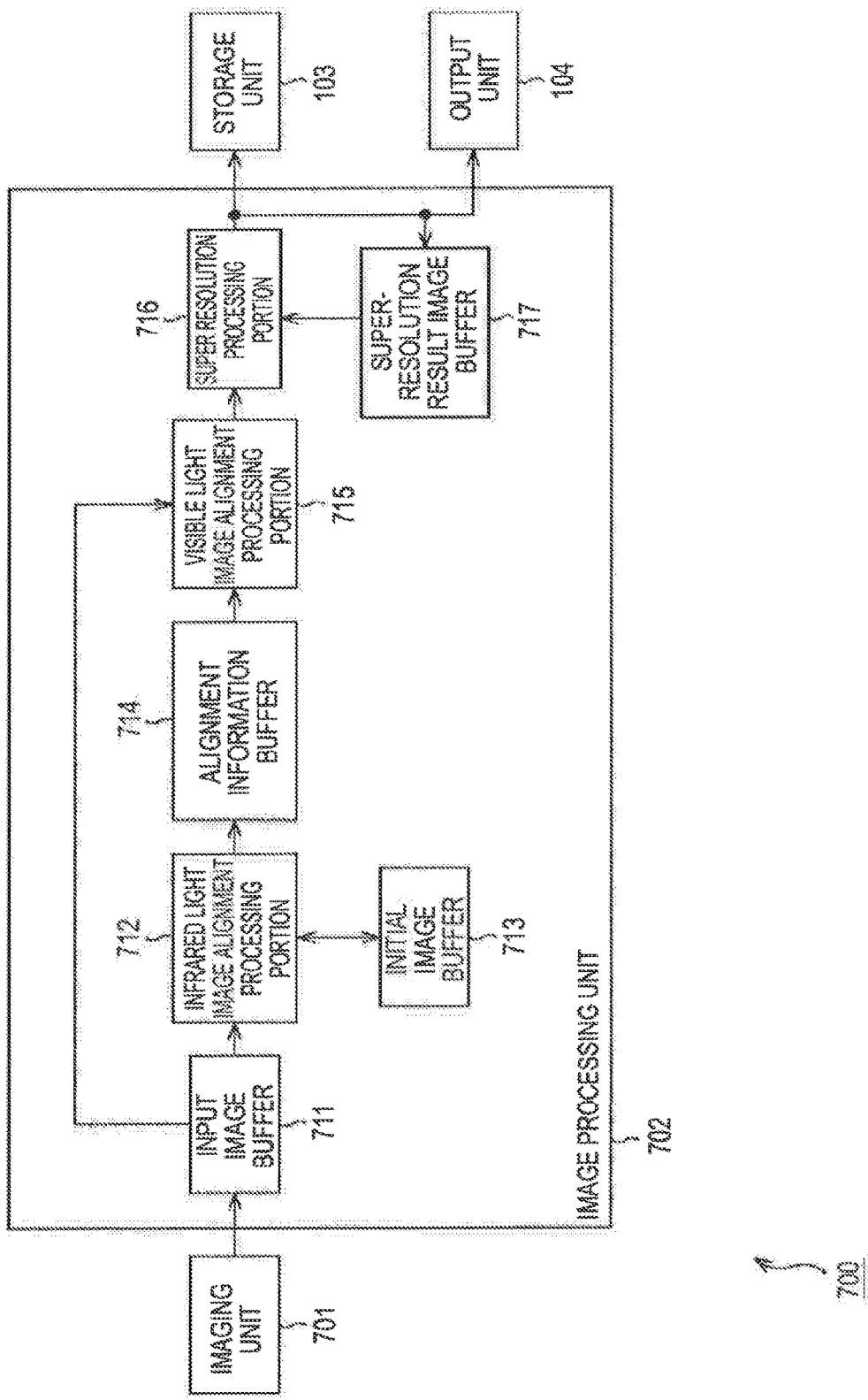
[FIG. 29]

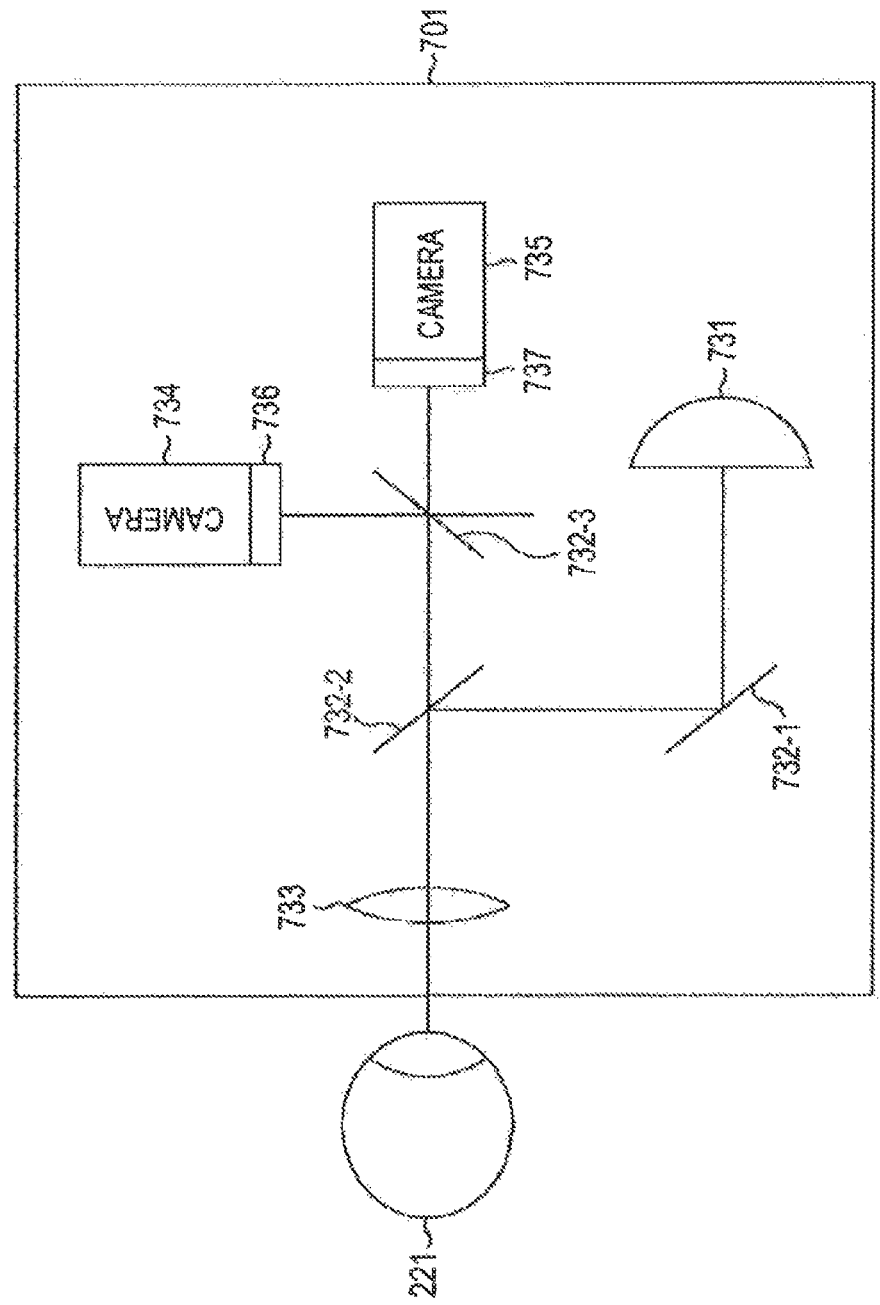
[FIG. 30]

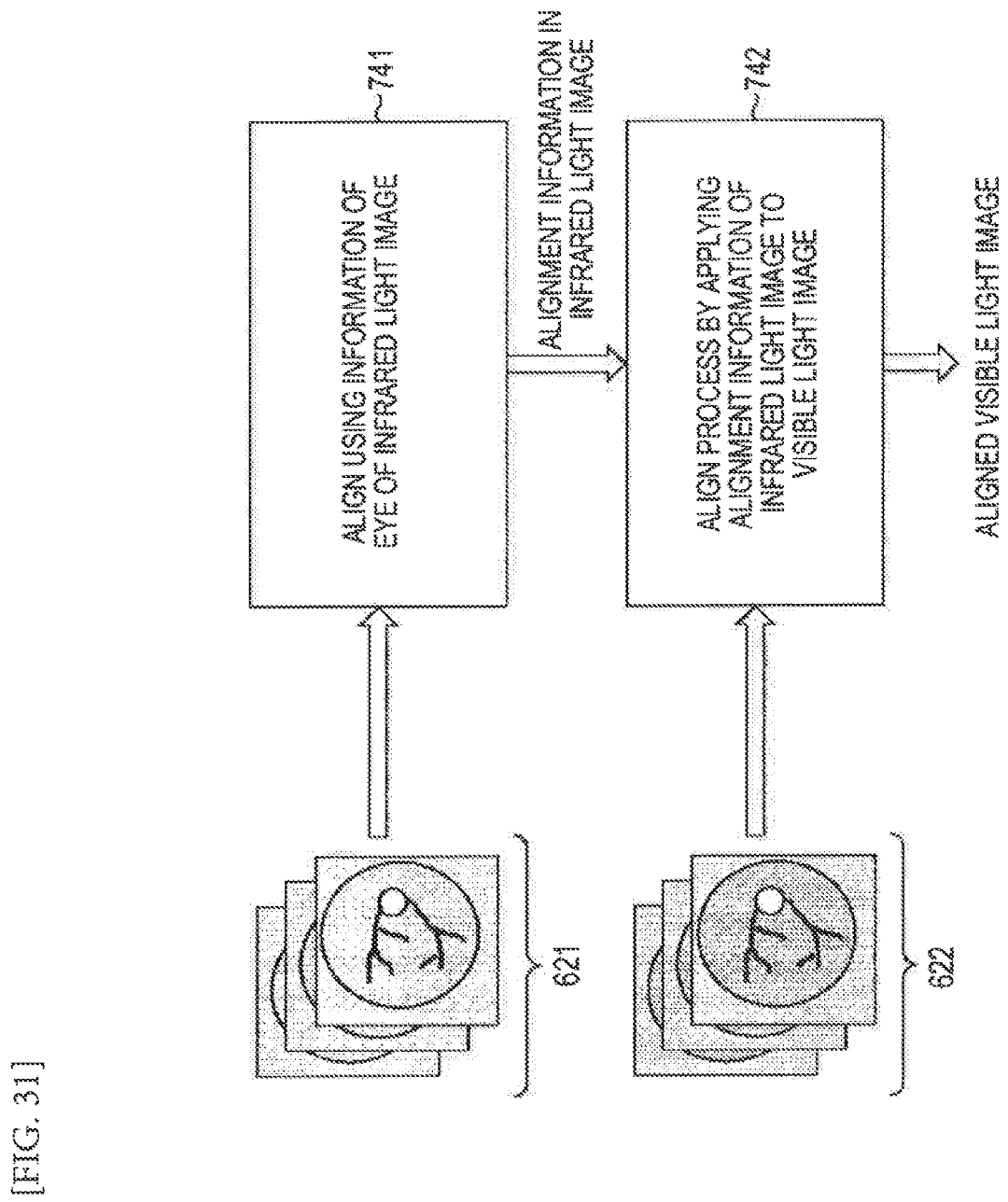

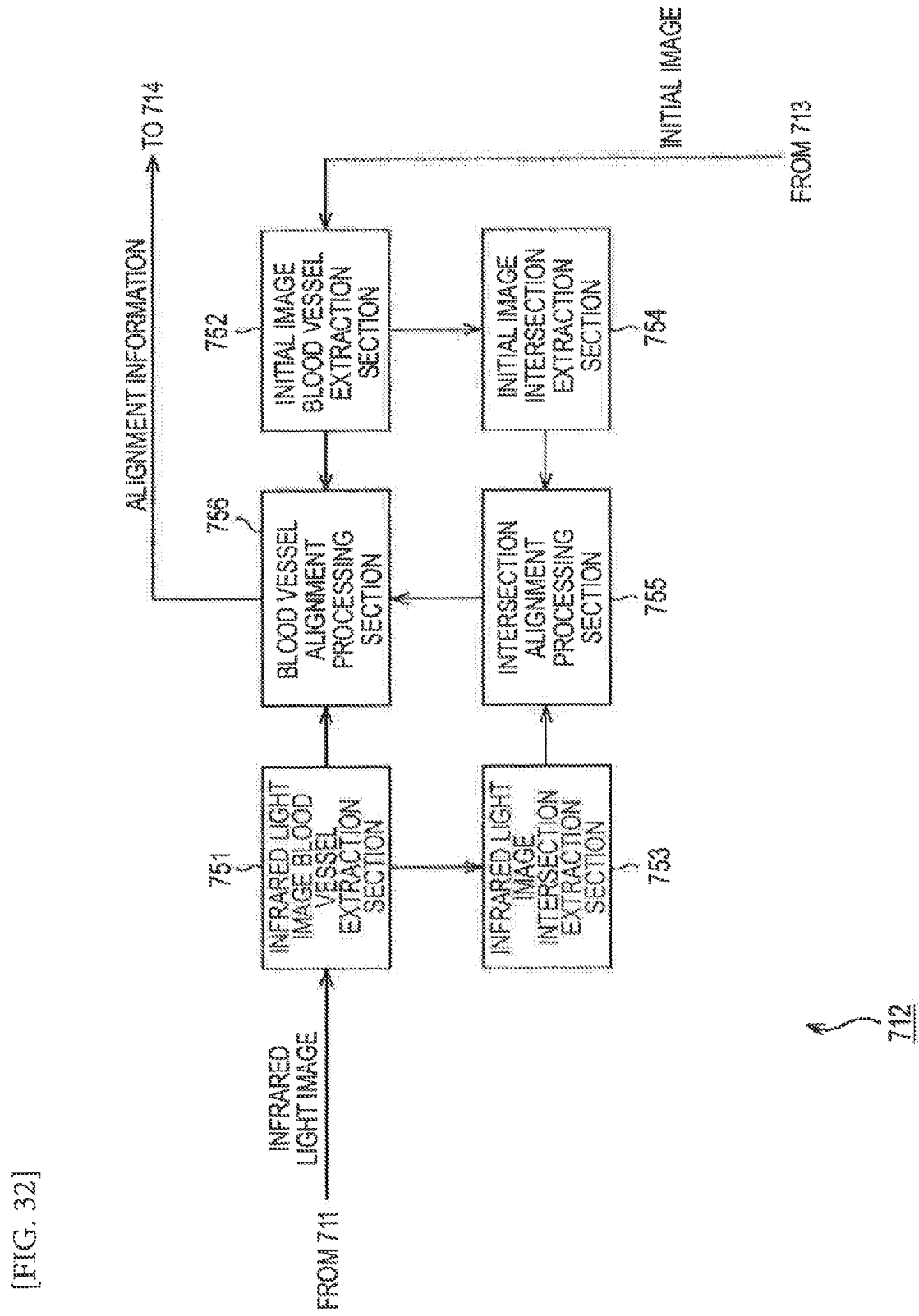
[FIG. 32]

[FIG.33]
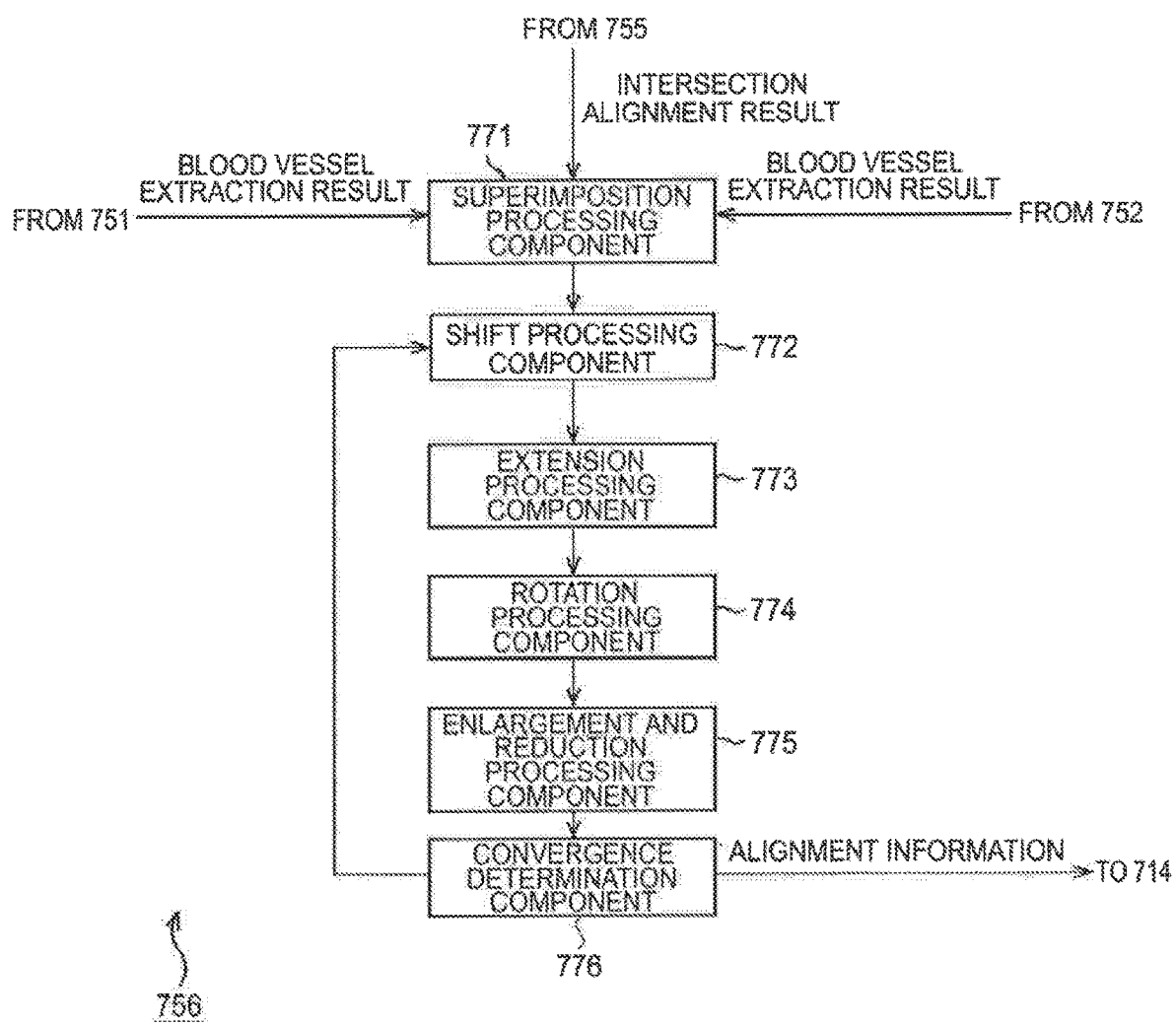

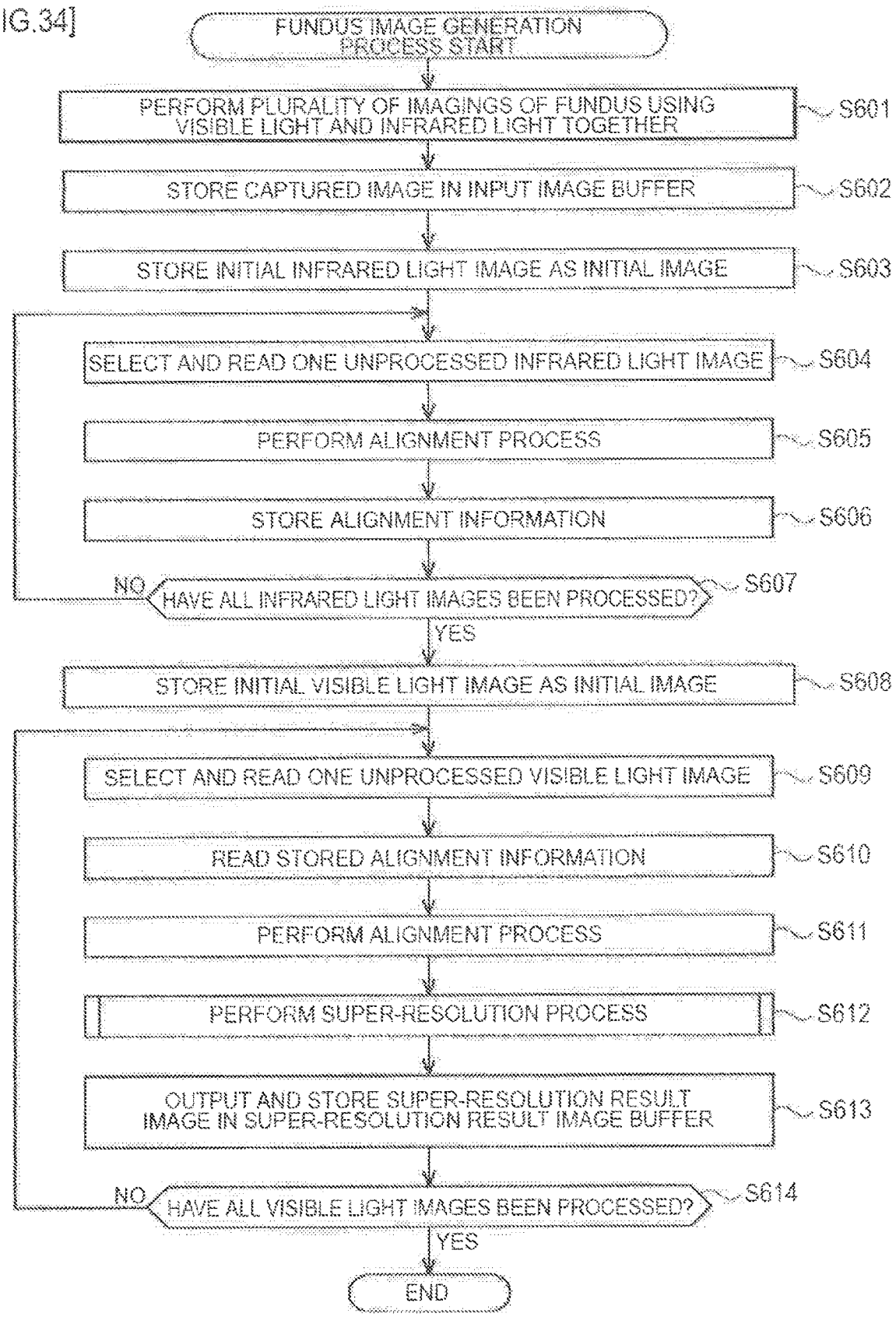

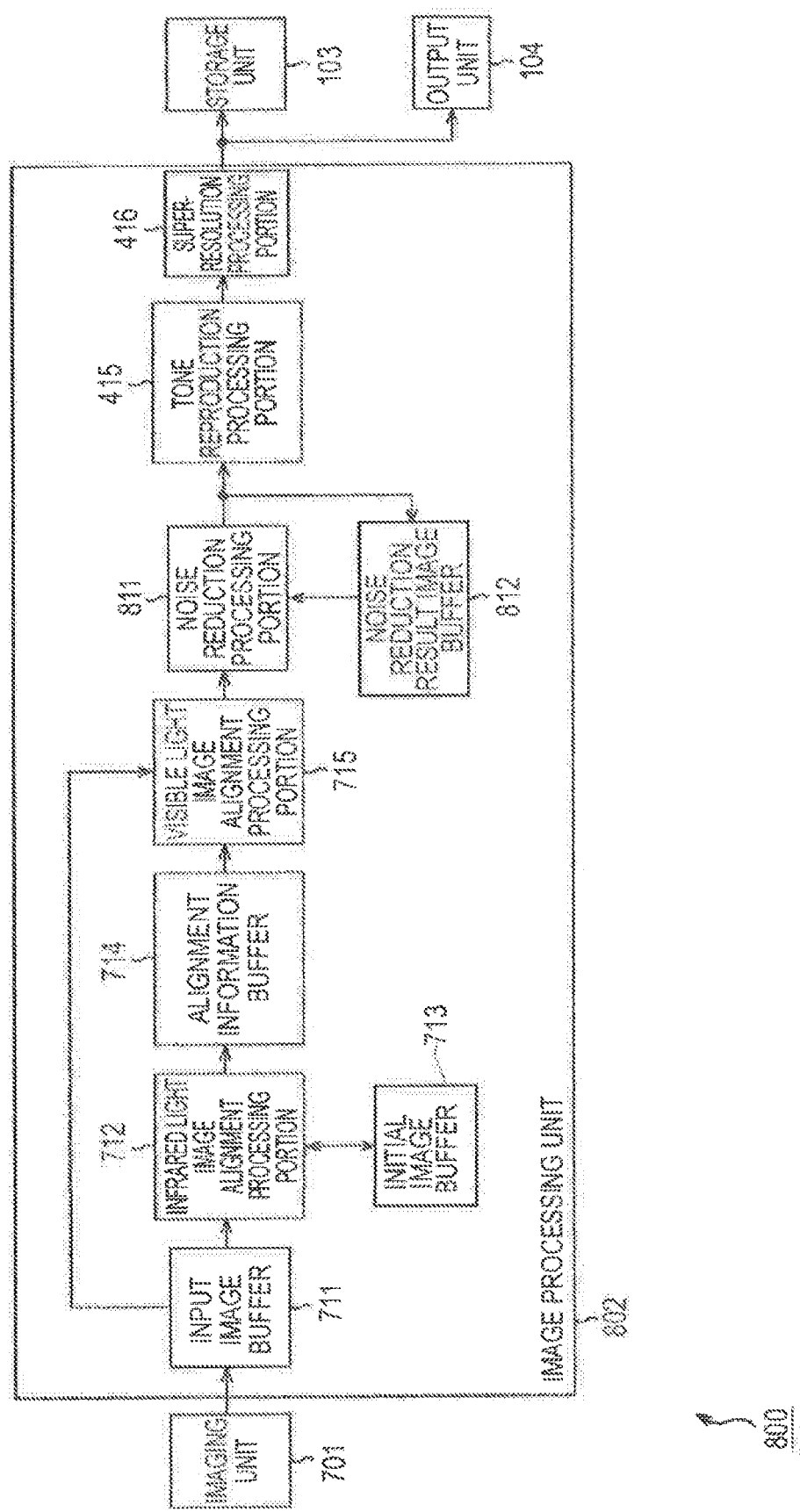
[FIG. 35]

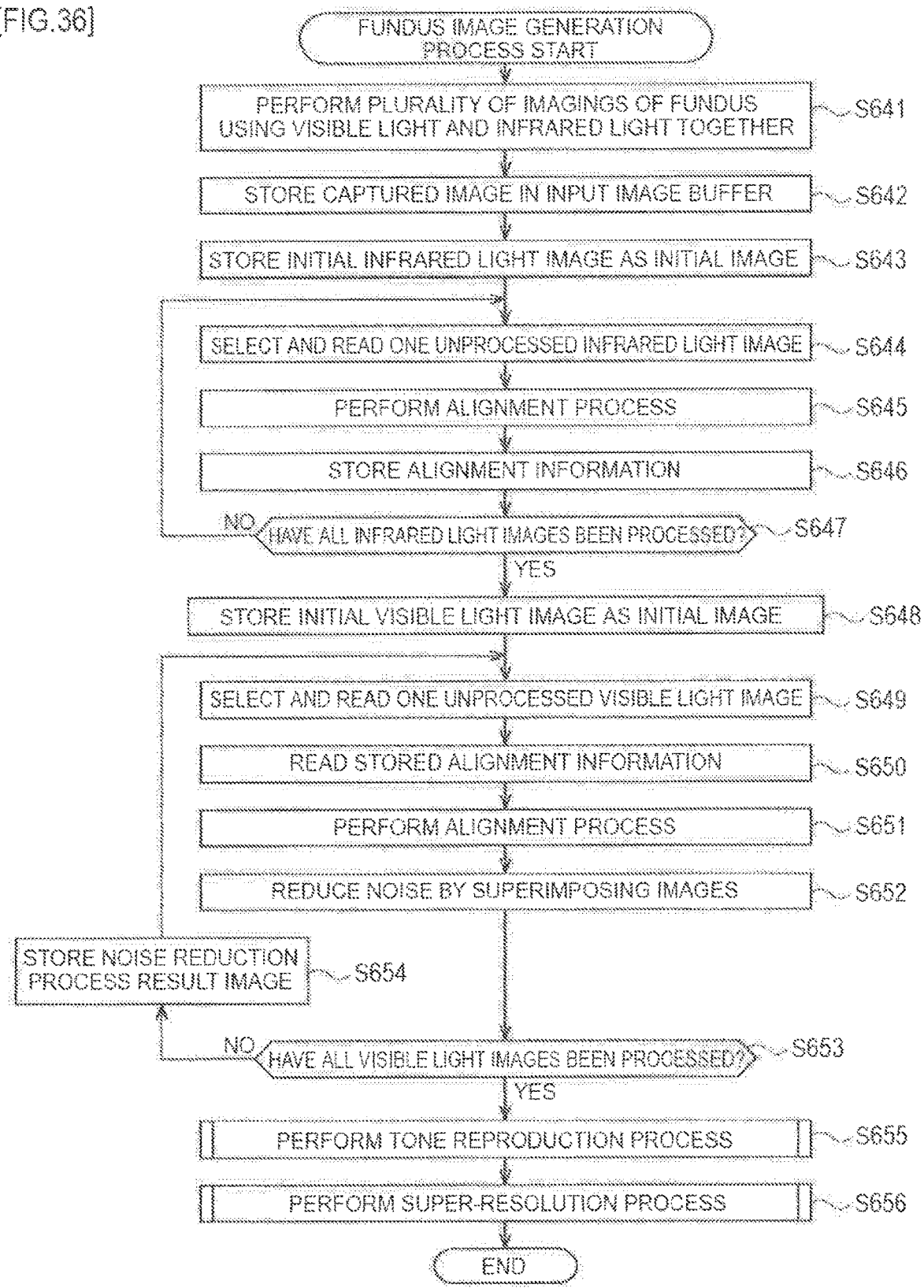

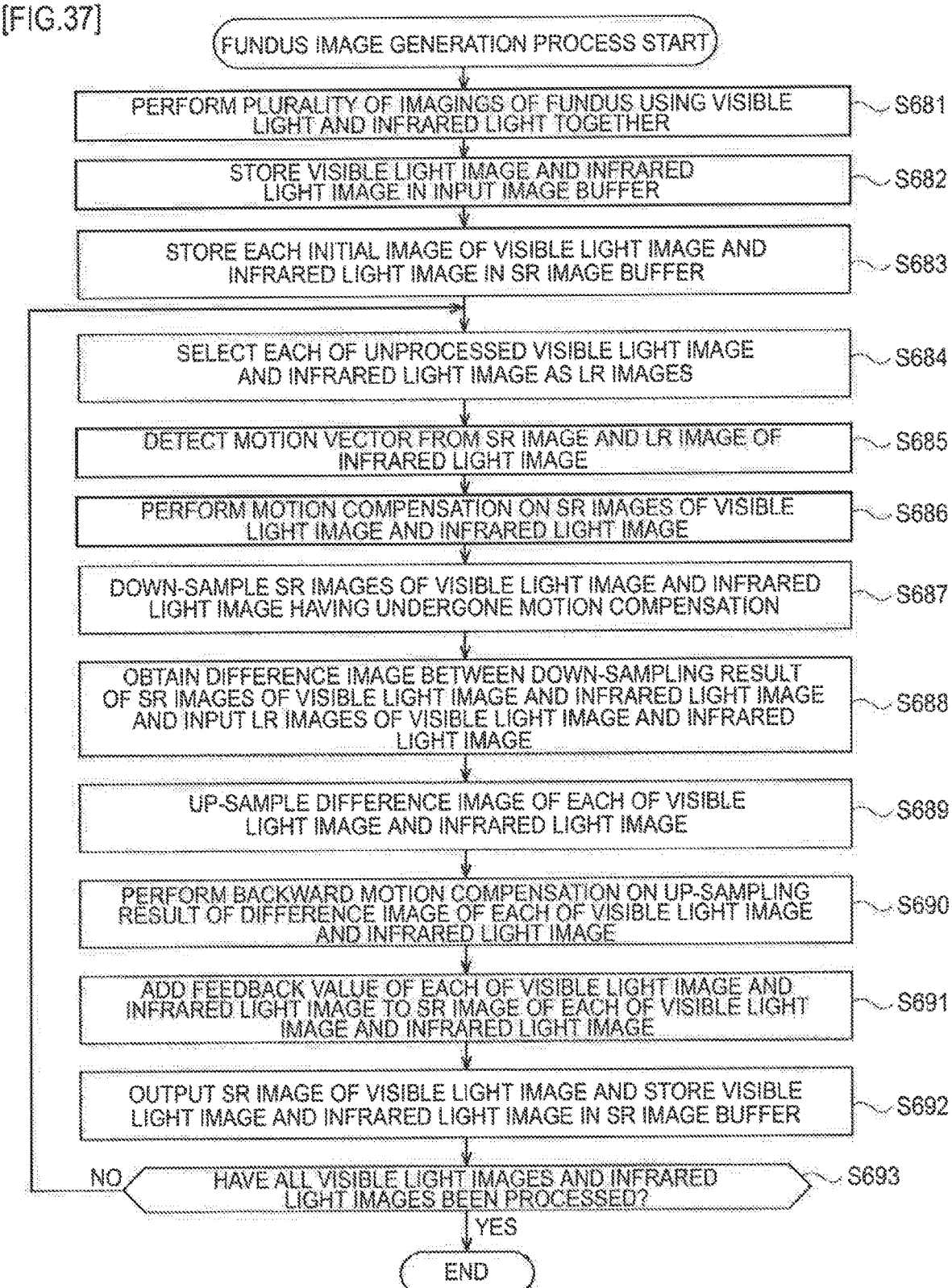

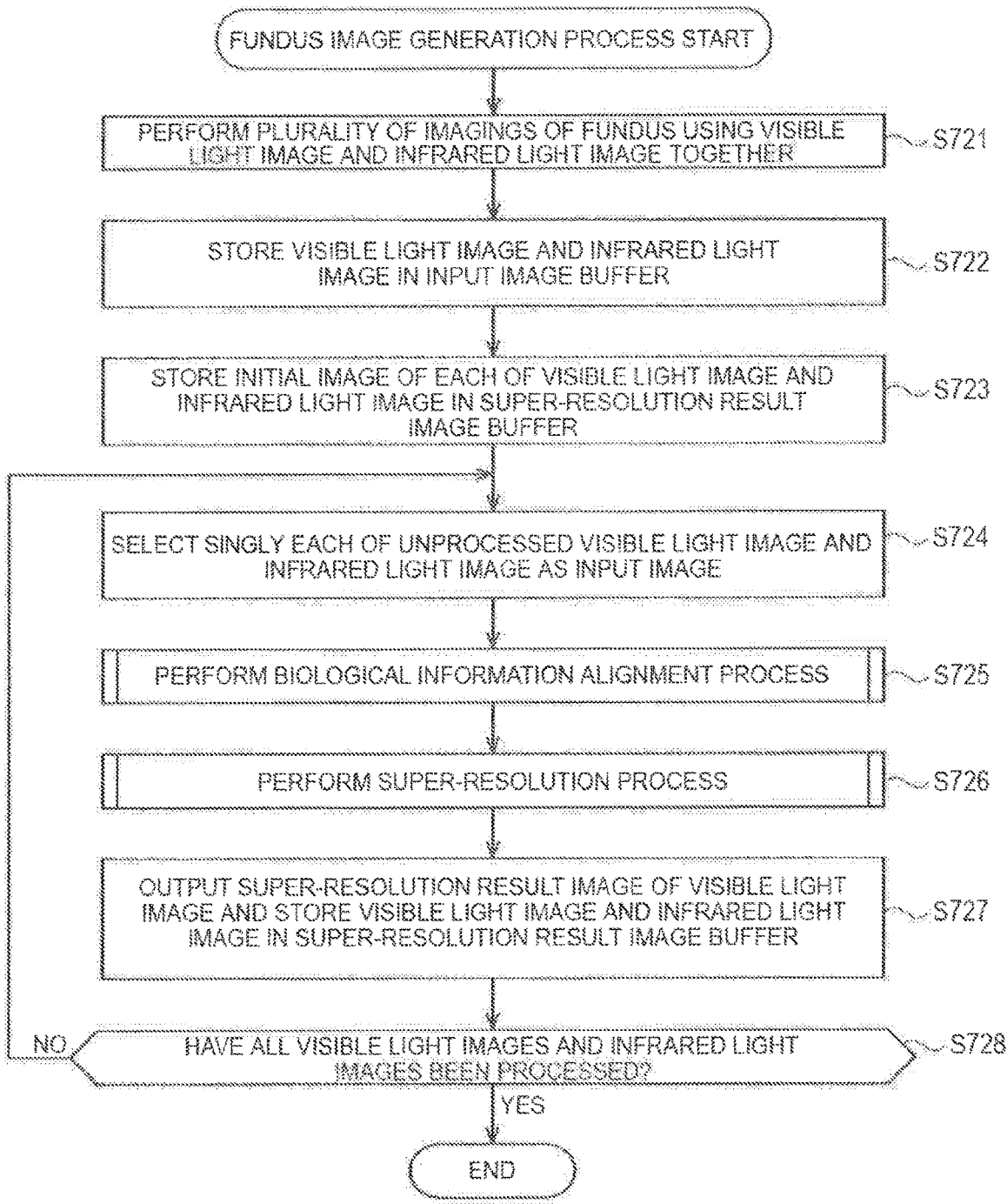

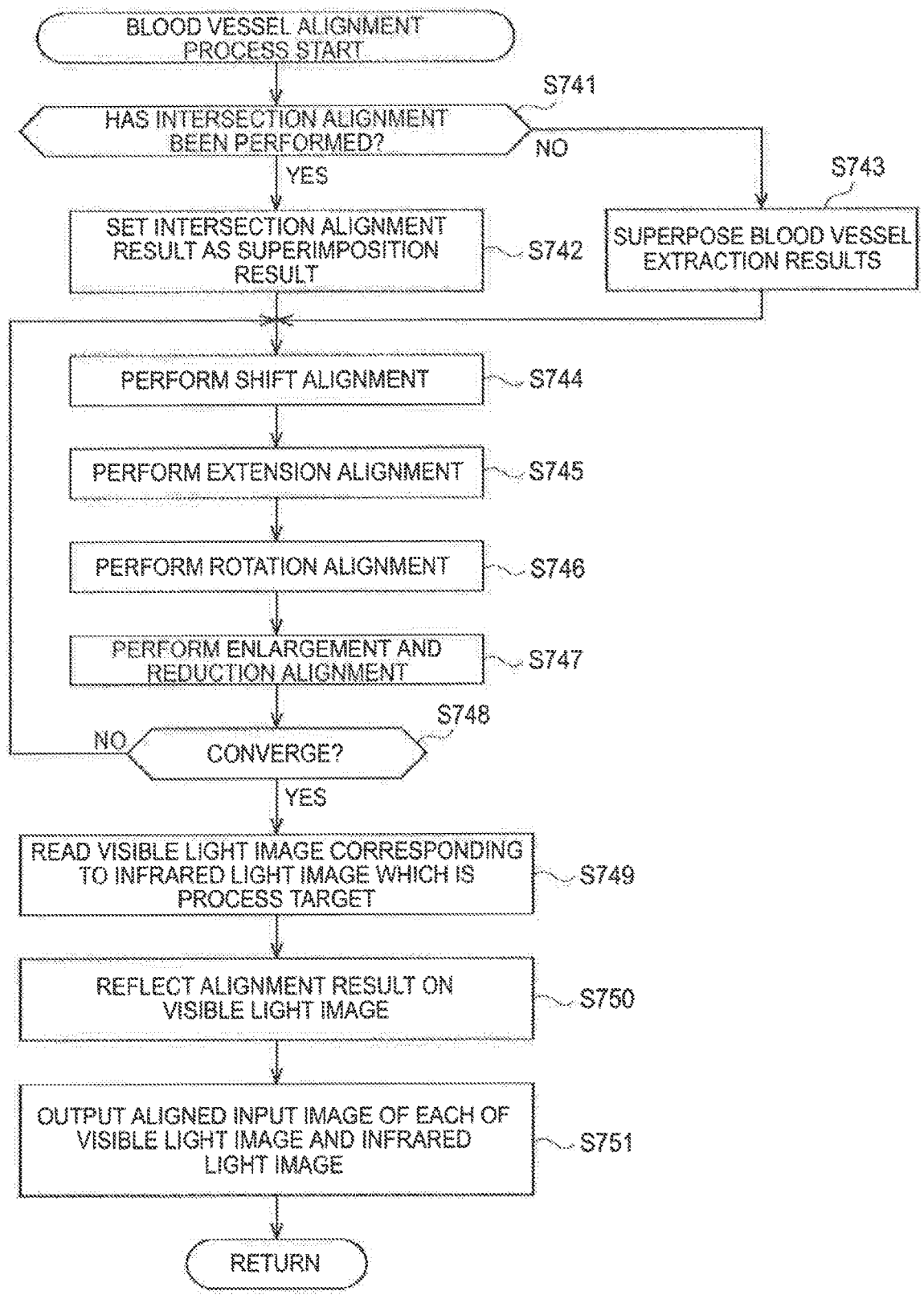
[FIG.39]

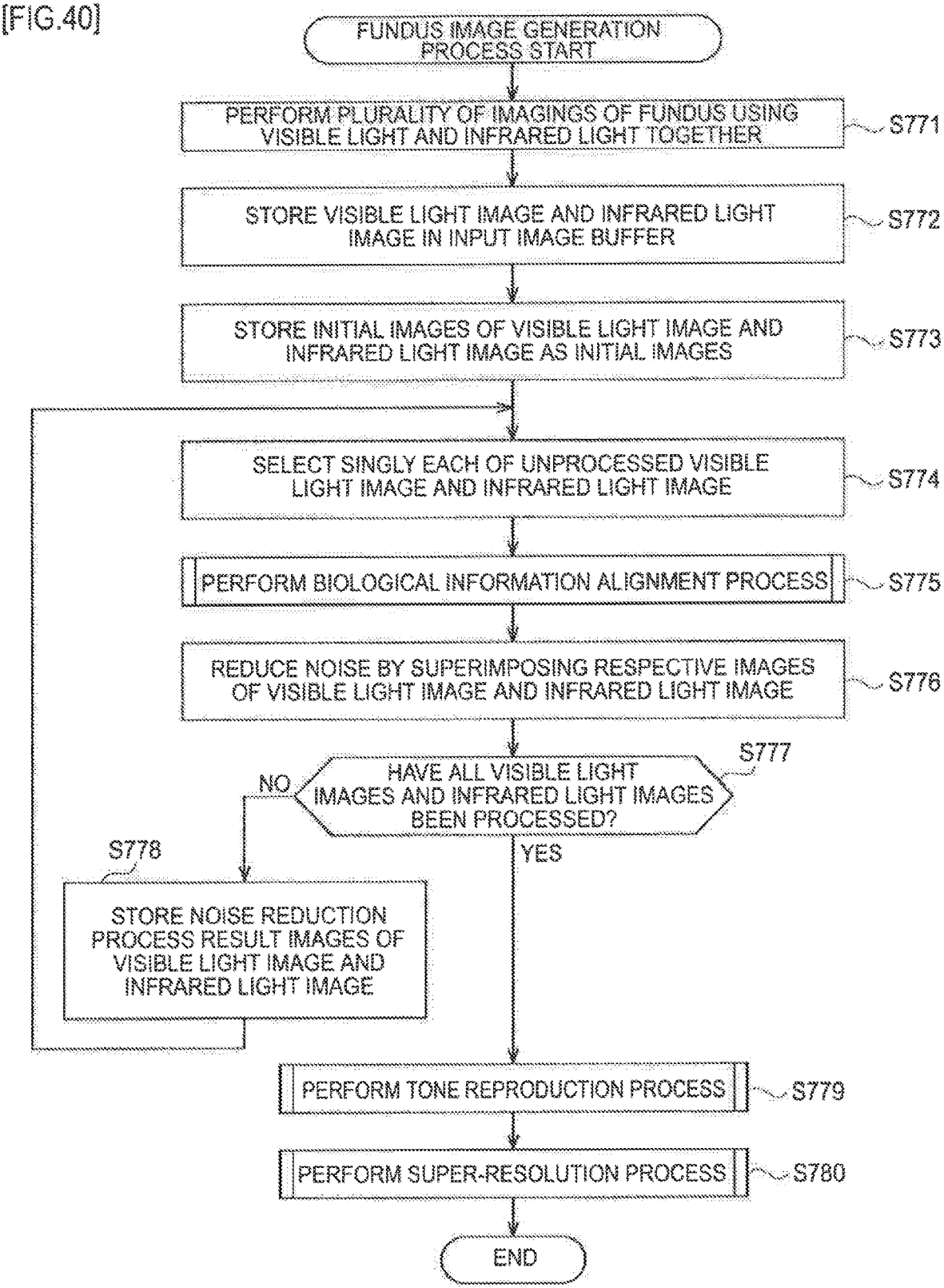

[FIG. 41]
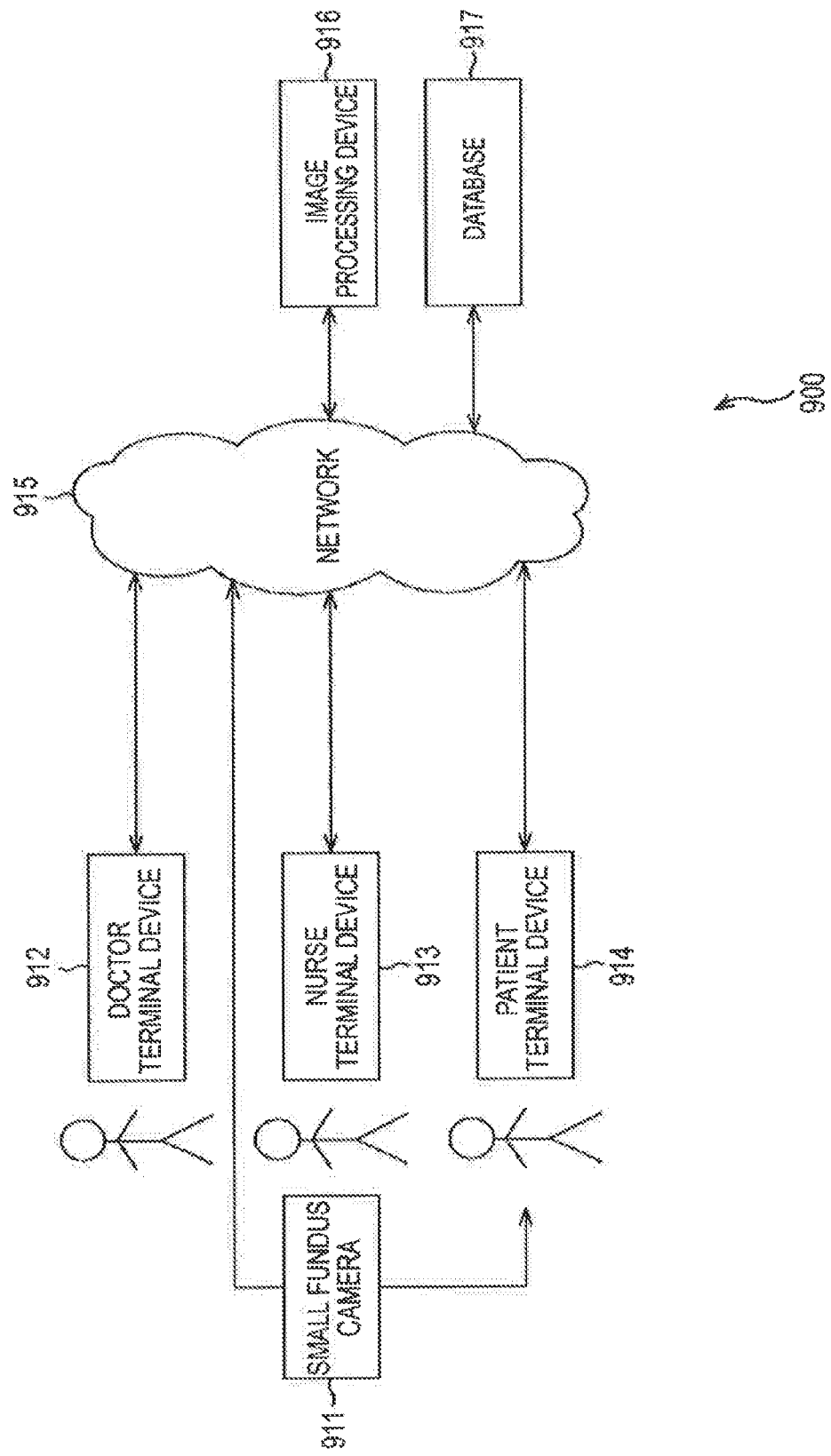

[FIG.42]
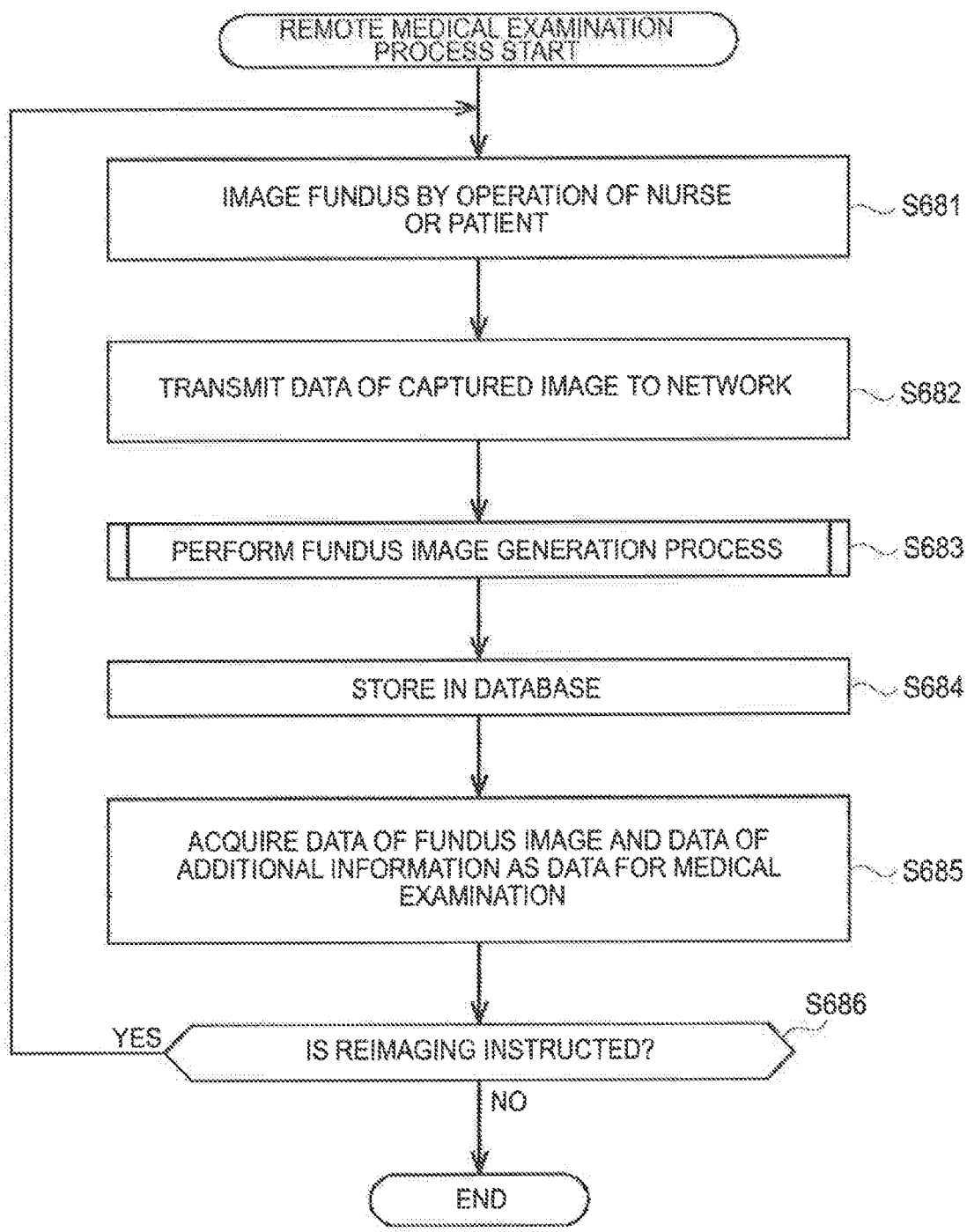

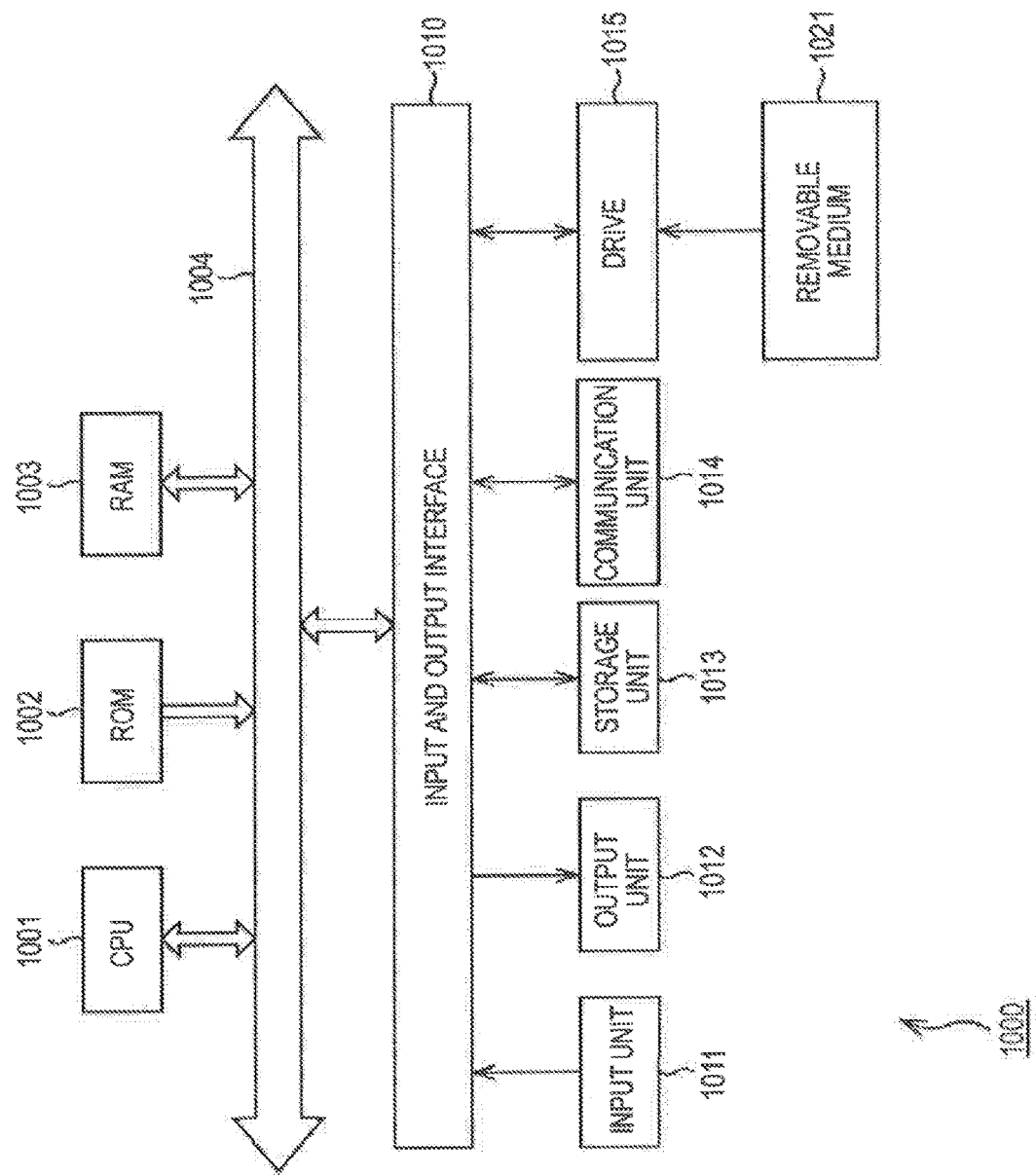
[FIG. 43]

IMAGE PROCESSING APPARATUS AND METHOD

CROSS-REFERENCES TO RELATED APPLICATIONS

The present application is a Continuation of U.S. application Ser. No. 13/818,027, filed Feb. 20, 2013, which is a national phase entry under 35 U.S.C. 371 of International Application No. PCT/JP2011/069339 filed Aug. 26, 2011, published on Mar. 1, 2012 as WO 2012/026597 A1, which claims priority from Japanese Patent Application Nos. JP 2010-190353 filed in the Japanese Patent Office on Aug. 27, 2010 and JP 2010-258556 filed in the Japanese Patent Office on Nov. 19, 2010.

TECHNICAL FIELD

The present technology relates to an image processing apparatus and an image processing method, and particularly to an image processing apparatus and an image processing method capable of suppressing an increase in a load on a subject and obtaining a captured image of the subject with higher image quality.

BACKGROUND ART

In the related art, a so-called fundus examination is performed in which a fundus such as a retina or an optic nerve head in an eyeball is observed through a pupil.

The fundus examination is performed using a dedicated apparatus such as, for example, a funduscope or a fundus camera. For example, an observer images an examinee's fundus in the eyeball which is an observation target with a fundus camera, displays a captured image obtained on a monitor or the like, and performs an observation.

In order to perform the observation more accurately, it is necessary to generate a captured image of the fundus (fundus image) with high image quality.

As a method of generating a fundus image with high image quality, for example, it is considered that an amount of light which is applied to the fundus is increased when the fundus is imaged.

In addition, it is considered that image processes are performed on a captured image obtained by imaging the fundus so as to obtain a fundus image with high image quality.

For example, PTL 1 discloses a method of performing noise reduction from a plurality of fundus images. In addition, for example, PTL 2 discloses a method of obtaining a high resolution image through irradiation of a periodic pattern. Further, for example, PTL 3 discloses a method of performing noise reduction from a plurality of fundus images. Furthermore, NPL 1 discloses a method of removing blurring through a combination of wavefront sensing and a Wiener filter.

CITATION LIST

Patent Literature

PTL 1: JP-A-2010-110392
PTL 2: JP-A-2008-272489
PTL 3: JP-A-09-253052

Non Patent Literature

NPL 1: "Hybrid technique for high resolution imaging of the eye fundus", Justo Arines and Salvador Bara, 2003

SUMMARY OF THE INVENTION

Technical Problem

However, if the examinee's fundus is irradiated with larger amount of light when imaging is performed, a load on the examinee increases, and thereby there is concern about unnecessary influence on the observation target or an increase in the psychological burden on the examinee. In addition, if the examinee's fundus is irradiated with a larger amount of light when imaging is performed, the examinee feels, what is called, dazzled and thus closes the eyelids, and thereby there is concern that it is not possible for a captured image with high image quality to be obtained.

In addition, in the method disclosed in PTL 1, it is necessary to display a positional deviation and for a user to correct the deviation. Further, this method is a method relating to noise removal, and it is difficult to emphasize outlines in this method.

In addition, in the method disclosed in PTL 2, since light is applied in different patterns and information thereof is used when imaging is performed, it is difficult to reduce a light amount in each irradiation.

Further, the method disclosed in PTL 3 is a method relating to noise removal, and it is difficult to emphasize outlines in this method.

Furthermore, the method disclosed in NPL 1 is a process regarding blurring removal of an image, and it is difficult to emphasize outlines in this method.

The present technology has been made in consideration of these circumstances, and an object thereof is to suppress an increase in load on a subject and obtain a captured image of the subject with higher image quality.

Solution to Problem

According to a first aspect of the present technology, there is provided an image processing apparatus including an alignment unit that performs alignment so as to adjust positions of a subject in a plurality of captured images obtained by an imaging unit which images the subject, by using biological information of the subject; and a superimposition unit that superimposes the captured images aligned by the alignment unit so as to generate an image of the subject having a dynamic range wider than that of the captured image.

The superimposition unit may include a detection portion that detects a motion vector between the captured image and the image of the subject generated through the superimposition; a motion compensation portion that performs motion compensation on the image of the subject by using the motion vector detected by the detection portion; a subtraction portion that subtracts the captured image from the image of the subject having undergone the motion compensation by the motion compensation portion; a backward motion compensation portion that performs motion compensation on a difference value between the image of the subject by the subtraction portion and the captured image in a reverse direction to the motion compensation by the motion compensation portion, by using the motion vector detected by the detection portion; and an adding portion that adds the difference value having undergone the motion compensation by the backward motion compensation portion to the image of the subject.

The superimposition unit may further include a down-sampling portion that down-samples the image of the subject having undergone the motion compensation by the motion compensation portion so as to reduce a resolution of the subject to the resolution of the captured image; and an up-sampling portion that up-samples the difference value between the image of the subject by the subtraction portion and the captured image so as to increase the resolution of the difference value to the resolution of the image of the subject, wherein the subtraction portion subtracts the captured image from the image of the subject down-sampled by the down-sampling portion, and wherein the backward motion compensation portion performs motion compensation on the difference value up-sampled by the up-sampling portion in a reverse direction to the motion compensation by the motion compensation portion, by using the motion vector detected by the detection portion.

The alignment unit may perform alignment so as to adjust positions of the subject in the captured images obtained by the imaging unit to a position of the subject in the image of the subject generated the previous time, and the superimposition unit may superimpose the captured images aligned by the alignment unit on the image of the subject generated the previous time one by one so as to generate the image of the subject which is obtained by superimposing the plurality of captured images on each other and has a dynamic range wider than that of the captured image.

The subject may be a fundus, and the alignment unit may use a blood vessel as the biological information.

The alignment unit may further use an intersection of the blood vessel as the biological information.

The image processing apparatus may further include an estimation unit that estimates a point spread function of the captured images aligned by the alignment unit; and a removal unit that removes blurring from the captured images by using the point spread function estimated by the estimation unit. Here, the superimposition unit may superimpose, the captured images which have been aligned by the alignment unit and from which the blurring has been removed by the removal unit, on the image of the subject generated the previous time one by one so as to generate the image of the subject which is obtained by superimposing the plurality of captured images on each other and has a dynamic range wider than that of the captured image.

The imaging unit may perform a plurality of imagings of the subject while irradiating the subject with irradiation light which is relatively dark.

According to the first aspect of the present technology, there is provided an image processing method of an image processing apparatus, including causing an alignment unit to perform alignment so as to adjust positions of a subject in a plurality of captured images obtained by an imaging unit which images the subject, by using biological information of the subject; and causing a superimposition unit to superimpose the captured images aligned so as to generate an image of the subject having a dynamic range wider than that of the captured image.

According to a second aspect of the present technology, there is provided an image processing apparatus including a superimposition unit that superimposes a plurality of captured images on each other obtained by an imaging unit which images a subject; and a grayscale correction unit that performs grayscale correction on a captured image which is generated by the superimposition unit superimposing the plurality of captured images according to biological information of the subject.

The grayscale correction unit may include a parameter setting portion that sets a value of a parameter for calculating a tone curve used for the grayscale correction of the captured image, according to the biological information of the subject.

The parameter setting portion may include an adjustment section that adjusts a value of a parameter for calculating the tone curve used for the grayscale correction of the captured image in a predetermined method; a correction section that corrects the captured image by using the parameter where the value has been adjusted by the adjustment section; a part checking section that checks a corrected captured image which is the captured image corrected by the correction section, for each part as a living body included in the captured image, in a method according to a feature of an image of each part; a comparison section that compares brightness of an uncorrected captured image which is the captured image before being corrected by the correction section with brightness of the corrected captured image when the corrected captured image passes checking performed by the part checking section; and an output section that outputs the value of the parameter as a set value when the adjustment by the adjustment section, the correction by the correction section, the checking by the part checking section, and the comparison by the comparison section are repeatedly performed, and it is determined by the comparison section that the corrected captured image is not brighter than the uncorrected captured image.

The parameter setting portion may further include a part recognition section that analyzes the captured image and recognizes a part as a living body included in the captured image, and the part checking section may check each part recognized by the part recognition section.

The parameter setting portion may further include a brightness value calculation section that calculates a brightness value indicating brightness of the captured image, and the comparison section may compare a brightness value of the uncorrected captured image with a brightness value of the corrected captured image, calculated by the brightness value calculation section.

The parameter setting portion may further include a parameter selection section that selects an adjustment target parameter to be adjusted by the adjustment section from a plurality of parameters.

The parameter setting portion may further include a part recognition section that analyzes the captured image and recognizes a part as a living body included in the captured image. Here, the correction section may correct an image of each part recognized by the part recognition section, the part checking section may check the image of each part corrected by the correction section, and the comparison section may compare brightness of the image of each part before and after corrected by the correction section.

The image processing apparatus may further include a high resolution unit that increases the resolution of the captured image having undergone the grayscale correction by the grayscale correction unit.

The high resolution unit may increase the resolution of the captured image having undergone the grayscale correction by the grayscale correction unit, according to the biological information of the subject.

According to the second aspect of the present technology, there is provided an image processing method of an image processing apparatus, including causing a superimposition unit to superimpose a plurality of captured images on each other obtained by an imaging unit which images a subject; and causing a grayscale correction unit to perform grayscale correction on a captured image which is generated by superimposing the plurality of captured images, according to biological information of the subject.

According to a third aspect of the present technology, there is provided an image processing apparatus including a superimposition unit that superimposes a plurality of captured images on each other obtained by an imaging unit which images a subject; and a high resolution unit that increases the resolution of a captured image which is generated by the superimposition unit superimposing the plurality of captured images, according to biological information of the subject.

The high resolution unit may include a super-resolution processing portion that performs a super-resolution process of improving the resolution of the captured image through learning on the captured image according to each of a plurality of kinds of learning dictionaries, so as to generate a plurality of super-resolution result images which are captured images with a high resolution; a part image evaluation portion that evaluates each super-resolution result image which is generated through the super-resolution process by the super-resolution processing portion by using each learning dictionary, for each part as a living body included in the super-resolution result image, in a method according to a feature of an image of each part; and an image selection portion that selects the optimal super-resolution result image from the plurality of super-resolution result images on the basis of the evaluation by the part image evaluation portion.

The high resolution unit may further include a part recognition portion that analyzes the super-resolution result image and recognizes a part as a living body included in the super-resolution result image, and the part image evaluation portion may evaluate each super-resolution result image for each part recognized by the part recognition portion, in a method according to a feature of an image of each part.

The image processing apparatus may further include a grayscale correction unit that performs grayscale correction on a captured image which is generated by the superimposition unit superimposing the plurality of captured images. Here, the high resolution unit may increase the resolution of the captured image having undergone the grayscale correction by the grayscale correction unit, according to the biological information of the subject.

The grayscale correction unit may perform grayscale correction on a captured image which is generated by the superimposition unit superimposing the plurality of captured images, according to the biological information of the subject.

According to the third aspect of the present technology, there is provided an image processing method of an image processing apparatus, including causing a superimposition unit to superimpose a plurality of captured images on each other obtained by an imaging unit which images a subject; and causing a high resolution unit to increase the resolution of a captured image which is generated by superimposing the plurality of captured images, according to biological information of the subject.

According to a fourth aspect of the present technology, there is provided an image processing apparatus including an infrared light image alignment unit that performs alignment so as to adjust positions of a subject in a plurality of infrared light images obtained by an imaging unit which images the subject, by using biological information of the subject; an alignment information storage unit that stores alignment information which is a result of the alignment by the infrared light image alignment unit; a visible light image alignment unit that performs alignment so as to adjust positions of the subject in a plurality of visible light images obtained by the imaging unit, by using the alignment information stored in the alignment information storage unit; and a superimposition unit that superimposes the visible light images aligned by the visible light alignment unit so as to generate an image of the subject having a dynamic range wider than that of the visible light image.

The imaging unit may perform a plurality of imagings of the subject while irradiating the subject with irradiation light including visible light with a predetermined light amount and infrared light with a light amount larger than the predetermined light amount.

The infrared light image alignment unit may perform the alignment such that a position of the subject in an infrared light image obtained by the imaging unit is adjusted to a position of the subject in the infrared light image which is first obtained out of the plurality of infrared light images obtained by the imaging unit, and the superimposition unit may superimpose the visible light images aligned by the visible light image alignment unit on the image of the subject generated the previous time one by one, so as to generate the image of the subject which is obtained by superimposing the plurality of visible light images on each other and has a dynamic range wider than that of the visible light image.

The subject may be a fundus, and the infrared light image alignment unit may use a blood vessel as the biological information.

The infrared light image alignment unit may further use an intersection of the blood vessel as the biological information.

According to the fourth aspect of the present technology, there is provided an image processing method of an image processing apparatus, including causing an infrared light image alignment unit to perform alignment so as to adjust positions of a subject in a plurality of infrared light images obtained by an imaging unit which images the subject, by using biological information of the subject; causing an alignment information storage unit to store alignment information which is a result of the alignment by the infrared light image alignment unit; causing a visible light image alignment unit to perform alignment so as to adjust positions of the subject in a plurality of visible light images obtained by the imaging unit, by using the alignment information stored in the alignment information storage unit; and causing a superimposition unit to superimpose the visible light images aligned by the visible light alignment unit so as to generate an image of the subject having a dynamic range wider than that of the visible light image.

According to a fifth aspect of the present technology, there is provided an image processing apparatus including an infrared light image alignment unit that performs alignment so as to adjust positions of a subject in a plurality of infrared light images obtained by an imaging unit which images the subject, by using biological information of the subject; an alignment information storage unit that stores alignment information which is a result of the alignment by the infrared light image alignment unit; a visible light image alignment unit that performs alignment so as to adjust positions of the subject in a plurality of visible light images obtained by the imaging unit, by using the alignment information stored in the alignment information storage unit; a superimposition unit that superimposes the plurality of visible light images aligned by the visible light alignment unit on each other; and a grayscale correction unit that performs grayscale correction on a visible light image generated by the superimposition unit superimposing the plurality of visible light images, according to biological information of the subject.

The imaging unit may performs a plurality of imagings of the subject while irradiating the subject with irradiation light including visible light with a predetermined light amount and infrared light with a light amount larger than the predetermined light amount.

The image processing apparatus may further include a high resolution unit that increases the resolution of the visible light image having undergone the grayscale correction by the grayscale correction unit.

The high resolution unit may increase the resolution of the visible light image having undergone the grayscale correction by the grayscale correction unit, according to the biological information of the subject.

The subject may be a fundus, and the infrared light image alignment unit may use a blood vessel as the biological information.

The infrared light image alignment unit may further use an intersection of the blood vessel as the biological information.

According to the fifth aspect of the present technology, there is provided an image processing method of an image processing apparatus, including causing an infrared light image alignment unit to perform alignment so as to adjust positions of a subject in a plurality of infrared light images obtained by an imaging unit which images the subject, by using biological information of the subject; causing an alignment information storage unit to store alignment information which is a result of the alignment by the infrared light image alignment unit; causing a visible light image alignment unit to perform alignment so as to adjust positions of the subject in a plurality of visible light images obtained by the imaging unit, by using the alignment information stored in the alignment information storage unit; causing a superimposition unit to superimpose the plurality of visible light images aligned by the visible light alignment unit on each other; and causing a grayscale correction unit to perform grayscale correction on a visible light image generated by the superimposition unit superimposing the plurality of visible light images, according to biological information of the subject.

According to a sixth aspect of the present technology, there is provided a medical examination system including an imaging unit that images a subject; an imaging processing unit that acquires a plurality of captured images obtained by the imaging unit via a network and performs an image process on the plurality of captured images acquired; a storage unit that stores the captured images having undergone the image process by the imaging processing unit; and an output unit that outputs the captured images stored in the storage unit.

The image processing unit may include an alignment portion that performs alignment so as to adjust positions of a subject in the plurality of captured images by using biological information of the subject; and a superimposition portion that superimposes the captured images aligned by the alignment portion so as to generate an image of the subject having a dynamic range wider than that of the captured image.

The image processing unit may further include a superimposition portion that superimposes a plurality of captured images obtained by the imaging unit on each other; and a grayscale correction portion that performs grayscale correction on a captured image which is generated by the superimposition portion superimposing the plurality of captured images, according to biological information of the subject.

The image processing unit may further include a high resolution portion that increases the resolution of the captured image having undergone the grayscale correction by the grayscale correction unit.

The imaging unit may perform a plurality of imagings of the subject while irradiating the subject with irradiation light including visible light with a predetermined light amount and infrared light with a light amount larger than the predetermined light amount. In addition, the image processing unit may further include an infrared light image alignment portion that performs alignment so as to adjust positions of a subject in a plurality of infrared light images obtained by the imaging unit, by using biological information of the subject; an alignment information storage portion that stores alignment information which is a result of the alignment by the infrared light image alignment portion; a visible light image alignment portion that performs alignment so as to adjust positions of the subject in a plurality of visible light images obtained by the imaging unit, by using the alignment information stored in the alignment information storage portion; and a superimposition portion that superimposes the visible light images aligned by the visible light alignment portion so as to generate an image of the subject having a dynamic range wider than that of the visible light image.

The imaging unit may perform a plurality of imagings of the subject while irradiating the subject with irradiation light including visible light with a predetermined light amount and infrared light with a light amount larger than the predetermined light amount. In addition, the image processing unit may further include an infrared light image alignment portion that performs alignment so as to adjust positions of a subject in a plurality of infrared light images obtained by the imaging unit, by using biological information of the subject; an alignment information storage portion that stores alignment information which is a result of the alignment by the infrared light image alignment portion; a visible light image alignment portion that performs alignment so as to adjust positions of the subject in a plurality of visible light images obtained by the imaging unit, by using the alignment information stored in the alignment information storage portion; a superimposition portion that superimposes the plurality of visible light images aligned by the visible light alignment portion on each other; and a grayscale correction portion that performs grayscale correction on a visible light image generated by the superimposition portion superimposing the plurality of visible light images, according to biological information of the subject.

The subject may be a fundus.

In the first aspect of the present technology, a plurality of captured images are obtained through alignment so as to adjust positions of a subject in a plurality of captured images obtained by an imaging unit which images the subject, by using biological information of the subject, and the captured images are aligned and superimposed, thereby generating an image of the subject having a dynamic range wider than that of the captured image.

In the second aspect of the present technology, a plurality of captured images obtained by an imaging unit which images a subject are superimposed on each other, and grayscale correction is performed on a captured image which is generated by the superimposing the plurality of captured images, according to biological information of the subject.

In the third aspect of the present technology, a plurality of captured images obtained by an imaging unit which images a subject are superimposed on each other, and the resolution of a captured image which is generated by superimposing the plurality of captured images is increased according to biological information of the subject.

In the fourth aspect of the present technology, alignment is performed so as to adjust positions of a subject in a plurality of infrared light images obtained by an imaging unit which images the subject, by using biological information of the subject, alignment information which is a result of the alignment is stored, alignment is performed so as to adjust positions of the subject in a plurality of visible light images by using the alignment information, and the aligned visible light images are superimposed so as to generate an image of the subject having a dynamic range wider than that of the visible light image.

In the fifth aspect of the present technology, alignment is performed so as to adjust positions of a subject in a plurality of infrared light images obtained by an imaging unit which images the subject by using biological information of the subject, alignment information which is a result of the alignment is stored, alignment is performed so as to adjust positions of the subject in a plurality of visible light images by using the alignment information, the plurality of aligned visible light images are superimposed on each other, and grayscale correction is performed on a visible light image generated by superimposing the plurality of visible light images according to biological information of the subject.

In the sixth aspect of the present technology, a subject is imaged, a plurality of captured images are acquired via a network, an image process is performed on the plurality of captured images acquired, the captured images having undergone the image process are stored, and the captured images stored are output.

Advantageous Effects of Invention

According to the present technology, it is possible to process an image. Particularly, it is possible to suppress an increase in a load on a subject and obtain a captured image of the subject with higher image quality.

BRIEF DESCRIPTION OF DRAWINGS

FIG. 1 is a block diagram illustrating a main configuration example of the fundus image processing apparatus to which the present technology is applied.

FIG. 2 is a flowchart illustrating an example of the flow of the fundus image generation process.

FIG. 3 is a block diagram illustrating another configuration example of the fundus image processing apparatus to which the present technology is applied.

FIG. 4 is a diagram illustrating an example of the flow of the overall processes.

FIG. 5 is a block diagram illustrating a main configuration example of the biological information alignment processing portion.

FIG. 6 is a diagram illustrating an example of the flow of the alignment process using biological information.

FIG. 7 is a block diagram illustrating a main configuration example of the blood vessel alignment processing section.

FIG. 8 is a diagram illustrating an example of the flow of the blood vessel alignment process.

FIG. 9 is a block diagram illustrating a main configuration example of the super-resolution processing portion.

FIG. 10 is a diagram illustrating an example of the flow of the super-resolution process.

FIG. 11 is a diagram illustrating an example of the flow of the PSF estimation process using a blood vessel image.

FIG. 12 is a flowchart illustrating an example of the flow of the fundus image generation process.

FIG. 13 is a flowchart illustrating an example of the flow of the biological information alignment process.

FIG. 14 is a flowchart illustrating an example of the flow of the blood vessel alignment process.

FIG. 15 is a flowchart illustrating an example of the flow of the super-resolution process.

FIG. 16 is a block diagram illustrating still another configuration example of the fundus image processing apparatus to which the present technology is applied.

FIG. 17 is a diagram illustrating an example of the flow of the overall processes.

FIG. 18 is a block diagram illustrating a main configuration example of the tone reproduction processing portion.

FIG. 19 is a diagram illustrating an example of the tone curve.

FIG. 20 is a block diagram illustrating a main configuration example of the parameter setting section.

FIG. 21 is a block diagram illustrating a main configuration example of the super-resolution processing portion.

FIG. 22 is a flowchart illustrating another example of the flow of the fundus image generation process.

FIG. 23 is a flowchart illustrating an example of the flow of the tone reproduction process.

FIG. 24 is a flowchart illustrating an example of the flow of the parameter setting process.

FIG. 25 is a flowchart illustrating an example of the flow of the super-resolution process.

FIG. 26 is a block diagram illustrating another configuration example of the parameter setting portion.

FIG. 27 is a flowchart illustrating another example of the flow of the parameter setting process.

FIG. 28 is a diagram illustrating an outline of a fourth embodiment.

FIG. 29 is a block diagram illustrating still another configuration example of the fundus image processing apparatus to which the present technology is applied.

FIG. 30 is a diagram illustrating a main configuration example of the imaging unit.

FIG. 31 is a diagram illustrating the flow of the process performed by the image processing unit.

FIG. 32 is a block diagram illustrating a main configuration example of the infrared light image alignment processing portion.

FIG. 33 is a block diagram illustrating a main configuration example of the blood vessel alignment processing section.

FIG. 34 is a flowchart illustrating another example of the flow of the fundus image generation process.

FIG. 35 is a block diagram illustrating another configuration example of the fundus image processing apparatus.

FIG. 36 is a flowchart illustrating another example of the flow of the fundus image generation process.

FIG. 37 is a flowchart illustrating another example of the flow of the fundus image generation process.

FIG. 38 is a flowchart illustrating another example of the flow of the fundus image generation process.

FIG. 39 is a flowchart illustrating another example of the flow of the blood vessel alignment process.

FIG. 40 is a flowchart illustrating another example of the flow of the fundus image generation process.

FIG. 41 is a diagram illustrating a configuration example of the remote medical examination system.

FIG. 42 is a flowchart illustrating an example of the flow of the remote medical examination process.

FIG. 43 is a block diagram illustrating a main configuration example of the personal computer to which the present technology is applied.

DESCRIPTION OF EMBODIMENTS

Hereinafter, embodiments of the present technology will be described. In addition, the description will be made in the following order.

1. First embodiment (fundus image processing apparatus)
2. Second embodiment (fundus image processing apparatus)
3. Third embodiment (fundus image processing apparatus)
4. Fourth embodiment (fundus image processing apparatus)
5. Fifth embodiment (fundus image processing apparatus)
6. Sixth embodiment (remote medical examination system)
7. Seventh embodiment (personal computer)

1. First Embodiment

Configuration of Fundus Image Processing Apparatus

FIG. 1 is a block diagram illustrating a main configuration example of the fundus image processing apparatus to which the present technology is applied. The fundus image processing apparatus 100 illustrated in FIG. 1 is an apparatus which images the fundus such as the retina or the optic nerve head in the eyeball of an examinee who is an observation target, and obtains an image of the fundus (fundus image) which is a captured image thereof.

The fundus image processing apparatus 100 restricts an amount of light applied to a subject and performs imaging in order to suppress an increase in a load on the subject (the examinee's fundus). In addition, in order to obtain a fundus image with higher image quality, the fundus image processing apparatus 100 performs a plurality of imagings so as to obtain a plurality of images, and perform a super-resolution process using them.

The fundus image processing apparatus 100 includes an imaging unit 101, an image processing unit 102, a storage unit 103, and an output unit 104.

The imaging unit 101 includes an imaging device using, for example, a CCD (Charge Coupled Device), a CMOS (Complementary Metal Oxide Semiconductor), or the like, and images the examinee's fundus at a predetermined position. The imaging unit 101 may employ any device as long as the device images the examinee's fundus and obtains a fundus image. However, the imaging unit 101 has a function of irradiating a subject with light at the time of imaging in order to obtain a fundus image with higher image quality.

Generally, a light amount of light to be applied (irradiation light) is preferably increased (the fundus is irradiated with stronger irradiation light to so as to be brighter) in order to obtain a fundus image with higher image quality; however, if an amount of irradiation light is merely increased, a load on the subject increases, and thereby there is concern about unnecessary influence on the observation target or an increase in the psychological burden on the examinee. In addition, the examinee feels, dazzled and thus closes the eyelids, and, as a result, there is concern that it is not possible for a captured image with high image quality to be obtained.

Therefore, the imaging unit 101 performs a plurality of imagings instead of increasing a light amount of irradiation light. In other words, the imaging unit 101 applies a small amount of irradiation light and repeatedly performs a plurality of imagings of the fundus. Therefore, the imaging unit 101 preferably performs a plurality of imagings in as short a time as possible such that the respective fundus images obtained through the imagings can be as close to each other as possible.

The respective fundus images obtained through these imagings have low quality since the irradiation light is weak (dark). The imaging unit 101 supplies a plurality of low quality fundus images obtained in this way to the image processing unit 102.

The image processing unit 102 generates a single fundus image with higher image quality by using the plurality of fundus images with low image quality supplied from the imaging unit 101, and stores the fundus image in the storage unit 103 or outputs the fundus image from the output unit 104.

The storage unit 103 includes any recording medium such as, for example, a hard disk, a flash memory, or a RAM (Random Access Memory), and stores the fundus image with higher image quality supplied from the image processing unit 102. The fundus image stored in the storage unit 103 is read by a reproduction unit (not shown) or the like and is displayed on the output unit 104 or is transmitted to other devices or undergoes image processes by an image processing unit (not shown).

The output unit 104 includes any monitor such as a CRT (Cathode Ray Tube) display or an LCD (Liquid Crystal Display), an output terminal, or the like, and displays the fundus image supplied from the image processing unit 102 on the monitor thereof or outputs an external apparatus of the fundus image processing apparatus 100.

As illustrated in FIG. 1, the image processing unit 102 includes an input image buffer 111, a super-resolution processing portion 112, an SR (Super-Resolution) image buffer 113, and a calculation portion 114.

The input image buffer 111 includes any recording medium such as, for example, a hard disk, a flash memory, or a RAM, holds a plurality of fundus images (captured images) with low image quality supplied from the imaging unit 101 as input images, and supplies the respective input images to the super-resolution processing portion 112 as an LR (Low Resolution) images at a predetermined timing.

[Configuration of Super-Resolution Processing Portion]

The super-resolution processing portion 112 performs the same super-resolution process as a super-resolution processor disclosed in, for example, JP-A-2009-093676 (hereinafter, referred to as PTL 4). That is to say, the super-resolution processing portion 112 recursively repeats a super-resolution process of calculating and outputting a feedback value for generating a new SR image by using an LR image supplied from the input image buffer 111, and an SR image, generated in the past, supplied from the SR image buffer 113. The super-resolution processing portion 112 supplies a feedback value calculated as a result of the super-resolution process to the calculation portion 114.

The SR image buffer 113 includes any recording medium such as, for example, a hard disk, a flash memory, or a RAM, and holds a generated SR image and supplies the SR image to the super-resolution processing portion 112 or the calculation portion 114 at a predetermined timing.

The calculation portion 114 generates a new SR image by adding the feedback value supplied from the super-resolution processing portion 112 to the SR image, generated in the past, supplied from the SR image buffer 113. The calculation portion 114 supplies the new generated SR image to the SR image buffer 113 so as to be held, and the SR image is used for a subsequent super-resolution process (generation of a new SR image). In addition, the calculation portion 114 supplies the generated SR image to the storage unit 103 so as to be stored, supplies the SR image to the output unit 104 so as to be displayed, or outputs the SR image to an external device or the like.

As illustrated in FIG. 1, the super-resolution processing portion 112 includes a motion vector detection section 121, a motion compensation section 122, a down-sampling filter 123, a calculation section 124, an up-sampling filter 125, and a backward motion compensation section 126.

The SR image read from the SR image buffer 113 is supplied to the motion vector detection section 121 and the motion compensation section 122, and the LR image read from the input image buffer 111 is supplied to the motion vector detection section 121 and the calculation section 124.

The motion vector detection section 121 detects a motion vector using the SR image as a reference on the basis of the SR image and the LR image which are input thereto, and supplies the detected motion vector to the motion compensation section 122 and the backward motion compensation section 126.

The motion compensation section 122 performs motion compensation on the SR image on the basis of the motion vector supplied from the motion vector detection section 121, and supplies an image obtained through the motion compensation to the down-sampling filter 123. A position of an object reflected in the image obtained through the motion compensation is a position close to a position of an object reflected in the LR image.

The down-sampling filter 123 generates an image with the same resolution as that of the LR image by down-sampling the image supplied from the motion compensation section 122, and supplies the generated image to the calculation section 124.

As such, a motion vector obtained from an SR image and an LR image and an image obtained through motion compensation using the obtained motion vector is used as an image with the same resolution as that of the LR image that corresponds to simulating a fundus image (LR image) obtained through imaging on the basis of the SR image stored in the SR image buffer 113.

The calculation section 124 generates a difference image indicating a difference between the LR image and an image simulated in this way, and supplies the generated difference image to the up-sampling filter 125.

The up-sampling filter 125 generates an image with the same resolution as that of the SR image by up-sampling the difference image supplied from the calculation section 124, and outputs the generated image to the backward motion compensation section 126.

The backward motion compensation section 126 performs backward motion compensation on the image supplied from the up-sampling filter 125 on the basis of the motion vector supplied from the motion vector detection section 121, and supplies a feedback value indicating the image obtained through the backward motion compensation to the calculation portion 114. A position of an object reflected in the image obtained through the backward motion compensation is a position close to a position of an object reflected in the SR image stored in the SR image buffer 113.

The image processing unit 102 performs the super-resolution process on each of a plurality of fundus images (LR images) held in the input image buffer 111 by using the super-resolution processing portion 112, and finally generates a single SR image with higher image quality.

[Flow of Fundus Image Generation Process]

With reference to a flowchart of FIG. 2, a description will be made of an example of the fundus image generation process performed by the fundus image processing apparatus 100.

When the fundus image generation process for obtaining a fundus image with higher image quality starts, the imaging unit 101 reduces a light amount and performs a plurality of imagings of the examinee's fundus (subject) in step S101.

In step S102, the image processing unit 102 stores the captured image obtained through the process in step S101 in the input image buffer 111. In step S103, the image processing unit 102 generates an initial image which is an initial SR image using any method and is stored in the SR image buffer 113. For example, the image processing unit 102 generates an initial image by up-sampling the captured image (LR image) which has been first obtained to an image with the same resolution as that of the SR image.

In step S104, the input image buffer 111 selects one of the captured images (LR images) which are unprocessed and are held therein, and supplies the selected captured image to the super-resolution processing portion 112. In step S105, the motion vector detection section 121 detects a motion vector from the SR image and the LR image. In step S106, the motion compensation section 122 performs motion compensation on the SR image by using the motion vector.

In step S107, the down-sampling filter 123 down-samples the SR image, having undergone the motion compensation, to the same resolution as that of the LR image. In step S108, the calculation section 124 obtains a difference image between the down-sampling result of the SR image and the input LR image.

In step S109, the up-sampling filter 125 up-samples the difference image. In step S110, the backward motion compensation section 126 performs backward motion compensation on the up-sampling result of the difference image by using the motion vector detected through the process in step S105.

In step S111, the calculation portion 114 adds a feedback value which is a result of the up-sampling of the difference image calculated through the process in step S110 to the SR image, generated in the past, held in the SR image buffer 113. In step S112, the image processing unit 102 stores or outputs the generated new SR image in the storage unit 103 or from the output unit 104, and stores the new SR image in the SR image buffer 113.

In step S113, the input image buffer 111 determines whether or not all the captured images (LR images) have been processed, and, if it is determined that there are unprocessed captured images (LR images), the input image buffer returns the process to step S104, selects a new captured image as a process target, and repeatedly performs the subsequent processes on the captured image.

In step S113, if it is determined that all of a plurality of captured images obtained through a plurality of imagings by the imaging unit 101 have been processed, and thus a single fundus image with higher image quality has been obtained, the input image buffer 111 finishes the fundus image generation process.

In this way, the fundus image processing apparatus 100 can obtain a fundus image with higher image quality without increasing a light amount of irradiation light applied to the fundus. That is to say, the fundus image processing apparatus 100 can suppress an increase in load on a subject and obtain a captured image of the subject with higher image quality.

Although, in the above description, a description has been made that an SR image with a higher resolution than that of a captured image (LR image) is obtained as a fundus image with higher image quality by performing the super-resolution process, the present technology is not limited thereto, and the resolution thereof may be same as that of the captured image. In this case, in the fundus image processing apparatus 100 of FIG. 1, the down-sampling filter 123 and the up-sampling filter 125 are omitted.

Fundamentally, since a dynamic range is widened by superimposing a plurality of fundus images on each other obtained by the imaging unit 101, a fundus image with higher image quality can be obtained. However, a plurality of fundus images obtained by the imaging unit 101 are obtained through a plurality of imagings and thus are not exactly the same image as each other. For example, positional deviation or deformation may occur partially or entirely in an image. Therefore, if a plurality of fundus images are merely superimposed, there is concern that an image may be blurred due to positional deviation or the like and is thus twofold, and thereby the image may not have high image quality.

The super-resolution processing portion 112 performs motion detection in the motion vector detection section 121 and performs appropriate motion compensation by using the motion compensation section 122 or the backward motion compensation section 126, and thus it is possible to reduce a difference (positional deviation or the like) between superimposed images. Therefore, the fundus image processing apparatus 100 can obtain a captured image of a subject with higher image quality even without increasing the resolution in the super-resolution process.

The above super-resolution process may be performed with any unit. For example, the super-resolution process may be performed on an entire captured image, or may be performed for each partial image with a predetermined size called a macro block.

2. Second Embodiment

Configuration of Fundus Image Processing Apparatus

In the meanwhile, in a fundus image, there are many cases where an entire image basically includes an approximately uniform color. In addition, a light amount of irradiation light is reduced, and thus a fundus image is a relatively dark image. Further, generally, a plurality of imagings by the imaging unit 101 are performed in a relatively short time under as equal a condition as possible. Therefore, in many cases, a motion amount between images is relatively small. Further, even in a case where there is motion, there are few cases where a part of an image is moved so as to be radically moved by more than the other part, and there are many cases where approximately the entirety is moved approximately uniformly.

Therefore, in a method of performing motion detection by comparing images for each predetermined unit as in the fundus image processing apparatus 100, there is concern that motion detection may be difficult.

Therefore, a motion vector is not detected for each predetermined region but alignment of images may be performed on the entire image by using biological information of a subject.

FIG. 3 is a block diagram illustrating a main configuration example of the fundus image processing apparatus in that case. The fundus image processing apparatus 200 illustrated in FIG. 3 is the same apparatus as the fundus image processing apparatus 100 of FIG. 1, and has basically the same configuration as the fundus image processing apparatus 100 but includes an image processing unit 202 instead of the image processing unit 102.

The image processing unit 202 aligns a plurality of fundus images with relatively low image quality by using biological information of a subject, and superimposes the fundus images, thereby generating a single fundus image with higher image quality.

As illustrated in FIG. 3, the image processing unit 202 includes an input image buffer 111, a biological information alignment processing portion 212, a super-resolution processing portion 213, and a super-resolution result image buffer 214.

The biological information alignment processing portion 212 performs image alignment on a fundus image (input image) supplied from the input image buffer 111 and a fundus image (an image superimposed by the super-resolution processing portion 213) supplied from the super-resolution result image buffer 214 by using biological information of a subject.

The biological information alignment processing portion 212 uses, for example, a blood vessel, a nerve, the optic nerve head, or the like as the biological information used for the alignment. Of course, any biological information may be used, and others may be used. For example, in a case of observing a tissue or a cell which is used as a subject, a shape of the cell or the nucleus thereof may be used for image alignment as the biological information of a subject. In addition, a plurality of kinds of biological information (for example, the blood vessel, the optic nerve head, and the like) may be used.

The super-resolution processing portion 213 acquires a super-resolution process result image (an image obtained as a result of the super-resolution process) generated in the past from the super-resolution result image buffer 214, and superimposes the super-resolution result image on an input image aligned by the biological information alignment processing portion 212, thereby generating a new super-resolution result image. The super-resolution processing portion 213 stores or outputs the super-resolution result image in the storage unit 103 or from the output unit 104, and supplies the super-resolution result image to the super-resolution result image buffer 214 so as to be stored.

The super-resolution result image buffer 214 includes any recording medium such as, for example, a hard disk, a flash memory, or a RAM, holds the super-resolution result image generated by the super-resolution processing portion 213, and supplies the super-resolution result image to the biological information alignment processing portion 212 or the super-resolution processing portion 213 at a predetermined timing.

In other words, in the same manner as the case of FIG. 1, the imaging unit 101 reduces a light amount and generates a plurality of fundus images 222 by imaging the fundus of the eye 221 multiple times as illustrated in the rectangle 231 of FIG. 4. As illustrated in the rectangle 232 of FIG. 4, the input image buffer 111 stores a plurality of dark fundus images 222 with low image quality, and supplies the fundus images 222 to the biological information alignment processing portion 212 one by one at a predetermined timing.

The biological information alignment processing portion 212 aligns the fundus images 222 with the super-resolution result image by using information of the eye (biological information) as illustrated in the rectangle 233 of FIG. 4. As illustrated in the rectangle 234 of FIG. 4, the super-resolution processing portion 213 performs a super-resolution process and a high dynamic range process through image superimposition by using the aligned fundus images 222 (input images), and generates a super-resolution result image.

The fundus image 223 which is generated through the repetition of the alignment and the super-resolution process and has a higher resolution and a wider dynamic range is stored in the storage unit 103 or is output from the output unit 104. In addition, here, the high resolution indicates an image from which blurring is removed and which is thus sharp, and, the resolution may not be high in practice.

In other words, the fundus image processing apparatus 200 can suppress an increase in a load on a subject and obtain a fundus image with a higher image quality (with a wider dynamic range since blurring is suppressed) than that of a captured image obtained through imaging.

[Configuration of Biological Information Alignment Processing Portion]

FIG. 5 is a block diagram illustrating a main configuration example of the biological information alignment processing portion 212 of FIG. 3. As illustrated in FIG. 5, the biological information alignment processing portion 212 includes an input image blood vessel extraction section 241, a super-resolution result image blood vessel extraction section 242, an input image intersection extraction section 243, a super-resolution result image intersection extraction section 244, an intersection alignment processing section 245, and a blood vessel alignment processing section 246.

The input image blood vessel extraction section 241, as illustrated in FIG. 6, extracts a blood vessel part from an input image 251 (a fundus image with low image quality) supplied from the input image buffer 111 (process 261), and supplies the extracted blood vessel part to the blood vessel alignment processing section 246. For example, the input image blood vessel extraction section 241 extracts blood vessels from the input image by using an R component of RGB components as in a method disclosed in "Automatic Composition of Color Ocular Fundus Images", Katsuyoshi TANABE, Tetsuro TSUBOUCHI, Hidenori OKUDA, and Masahiro OKU, 2007 (hereinafter, referred to as NPL 2).

Similarly, the super-resolution result image blood vessel extraction section 242, as illustrated in FIG. 6, extracts a blood vessel part from a previous super-resolution result image 252 (a fundus image with high image quality) supplied from the super-resolution result image buffer 214 (process 262), and supplies it (the blood vessel extraction result 253) to the blood vessel alignment processing section 246.

As illustrated in FIG. 6, the blood vessel alignment processing section 246 aligns the blood vessels with each other between the input image 251 and the previous super-resolution result image 252 by using the blood vessel extraction result extracted from each image (process 266), and supplies the aligned input image 254 to the super-resolution processing portion 213 along with the blood vessel extraction result 253.

In addition, simple alignment may be performed using a position of an intersection of the blood vessel before the alignment (process 266) using the blood vessel extraction result (a shape or a position of the entire blood vessel). In addition, the intersection of the blood vessel is a portion (practically, also including a case where a blood vessel is at a twisted position) at which the blood vessels intersect each other or a branching portion in a captured image.

In this case, the input image blood vessel extraction section 241, as illustrated in FIG. 6, supplies the blood vessel extraction result from the input image 251 (a fundus image with low image quality), obtained through the process 261, to the input image intersection extraction section 243.

The input image intersection extraction section 243, as illustrated in FIG. 6, extracts an intersection from the blood vessel extraction result which is supplied from the input image blood vessel extraction section 241 (process 263), and supplies the intersection extraction result to the intersection alignment processing section 245.

In addition, the super-resolution result image blood vessel extraction section 242, as illustrated in FIG. 6, supplies the blood vessel extraction result 253 from the previous super-resolution result image 252 (a fundus image with high image quality), obtained through the process 262, to the super-resolution result image intersection extraction section 244.

The super-resolution result image intersection extraction section 244, as illustrated in FIG. 6, is an intersection from the blood vessel extraction result 253 supplied from the super-resolution result image blood vessel extraction section 242 (process 264), and supplies the intersection extraction result to the intersection alignment processing section 245.

The intersection alignment processing section 245, as illustrated in FIG. 6, aligns the intersections with each other between the input image 251 and the previous super-resolution result image 252 by using the intersection extraction result extracted from each image (process 265). In addition, the intersection alignment result is supplied to the blood vessel alignment processing section 246.

The blood vessel alignment processing section 246 sets the intersection alignment result supplied from the intersection alignment processing section 245 to an initial state, and performs input image alignment using the blood vessels, by the use of the blood vessel extraction result (process 266). In other words, the alignment is performed according to the intersection alignment result in the same manner as the intersection alignment, and the respective blood vessel extraction results are superimposed so as to be set to an initial state.

In this way, the blood vessel alignment processing section 246 can start alignment from a state of being simply aligned using the intersection, and thereby it is possible to perform alignment more easily and at high speed.

In addition, alignment using other pieces of biological information may also be performed. For example, first, the input image 251 may be superimposed on the previous super-resolution result image 252 while performing alignment at a position of the optic nerve head, the superimposed image may be set as an initial value, and alignment using an intersection may be performed.

[Configuration of Blood Vessel Alignment Processing Section]

Next, alignment using a position or a shape of the entire blood vessel will be described. FIG. 7 is a block diagram illustrating a main configuration example of the blood vessel alignment processing section 246. As illustrated in FIG. 7, the blood vessel alignment processing section 246 includes a superimposition processing component 271, a shift processing component 272, an extension processing component 273, a rotation processing component 274, an enlargement and reduction processing component 275, and a convergence determination component 276.

The superimposition processing component 271 superimposes the respective blood vessel extraction results supplied from the input image blood vessel extraction section 241 and the super-resolution result image blood vessel extraction section 242. In a case of performing alignment using an intersection, the superimposition processing component 271 superimposes the respective blood vessel extraction results while performing the same alignment as the intersection alignment by using the intersection alignment result supplied from the intersection alignment processing section 245. The superimposition processing component 271 supplies the superimposition result to the shift processing component 272.

In addition, the blood vessel alignment processing section 246, as illustrated in FIG. 8, sets the blood vessel extraction result 291 which is supplied from the input image blood vessel extraction section 241 and is extracted from the input image as a source, and performs alignment by setting the blood vessel extraction result 292 which is supplied from the super-resolution result image blood vessel extraction section 242 and is extracted from the previous super-resolution result image as a target. That is to say, the alignment is performed such that the blood vessel extraction result 291 is close to the blood vessel extraction result 292.

The shift processing component 272, as illustrated in FIG. 8, performs a longitudinal and transverse shift 281 of moving (shifting) the entire blood vessel extraction result 291 in any direction such as a longitudinal direction or a transverse direction, and supplies the superimposition result to the extension processing component 273 in a state where the blood vessel extraction result 291 is closest to the blood vessel extraction result 292. A method of determining to what extent the blood vessel extraction result 291 is close to the blood vessel extraction result 292 may use any method, and, for example, the determination is performed using an absolute value difference between both images. In other words, the shift processing component 272 moves (shifts) the entire blood vessel extraction result 291 and detects a position where an absolute value difference between the blood vessel extraction result 291 and the blood vessel extraction result 292 is the minimum. This determination method is also the same for the following processing components.

The extension processing component 273, as illustrated in FIG. 8, performs longitudinal and transverse extension 282 of extending (deforming) the blood vessel extraction result 291 in any direction such as a longitudinal direction or a transverse direction, and supplies the superimposition result to the rotation processing component 274 in a state where the blood vessel extraction result 291 is closest to the blood vessel extraction result 292. For example, the extension processing component 273 extends (deforms) the blood vessel extraction result 291 in any direction, and searches for a shape in which an absolute value difference between the blood vessel extraction result 291 and the blood vessel extraction result 292 is the minimum.

The rotation processing component 274, as illustrated in FIG. 8, performs rotation 283 of rotating the blood vessel extraction result 291 from side to side and supplies the superimposed result to the enlargement and reduction processing component 275 in a state where the blood vessel extraction result 291 is closest to the blood vessel extraction result 292. For example, the rotation processing component 274 rotates the blood vessel extraction result 291 from side to side, and searches for a direction in which an absolute value difference between the blood vessel extraction result 291 and the blood vessel extraction result 292 is the minimum.

The enlargement and reduction processing component 275, as illustrated in FIG. 8, performs enlargement and reduction 284 of enlarges or reduces the blood vessel extraction result 291 and supplies the superimposed result to the convergence determination component 276 in a state where the blood vessel extraction result 291 is closest to the blood vessel extraction result 292. For example, the rotation processing component 274 enlarges or reduces the blood vessel extraction result 291, and searches for a size where an absolute value difference between the blood vessel extraction result 291 and the blood vessel extraction result 292 is the minimum.

The convergence determination component 276 determines whether or not the alignment converges based on the superimposition results. For example, the convergence determination component 276 compares the alignment result obtained this time with the alignment result obtained the previous time by repeatedly performing the above-described respective processes multiple times, and, if the blood vessel extraction result 291 is closer to the blood vessel extraction result 292 than the previous time, it is determined that the alignment does not converge, and, if the blood vessel extraction result 291 is not closer to the blood vessel extraction result 292 than the previous time (for example, an absolute value difference between the blood vessel extraction result 291 and the blood vessel extraction result 292 is not smaller than the previous time), it is determined that the alignment converges.

If it is determined that the alignment does not converge (for example, an absolute value difference between the blood vessel extraction result 291 and the blood vessel extraction result 292 is smaller than the previous time), the convergence determination component 276 returns the superimposition result to the shift processing component 272 such that alignment is performed again. In addition, if it is determined that the alignment converges, the convergence determination component 276 performs alignment on the input image 251 on the basis of the superimposition result (for example, a superimposition result when an absolute value difference between the blood vessel extraction result 291 and the blood vessel extraction result 292 is the minimum) of the blood vessel extraction result which is the alignment result, and supplies the aligned input image 251 and the blood vessel extraction result to the super-resolution processing portion 213.

In addition, although, in the above description, a description has been made that the four processes including the longitudinal and transverse shift 281, the longitudinal and transverse extension 282, the rotation 283, and the enlargement and reduction 284 are performed in this order as a detailed example of the alignment, the present technology is not limited thereto, and processes other than the above-described processes may be further performed, or some of the above-described processes may be omitted. In addition, in a case where a plurality of processes are performed as described above, the processes may be performed in any order.

In addition, the biological information alignment processing portion 212 may perform alignment using a histogram of an edge part as disclosed in, for example, "Shape Matching and Object Recognition Using Shape Contexts", Serge Belongie, JitendraMalik, Jan Puzicha, 2002 (hereinafter, referred to as NPL 3).

Further, a method of determining convergence may use any method, and methods other than the above-described method may be used. For example, if an absolute value difference between the blood vessel extraction result 291 and the blood vessel extraction result 292 is equal to or less than a predetermined threshold value, it may be determined that convergence is performed.

In addition, alignment using an intersection of the blood vessels is basically performed in the same manner as alignment using the entire blood vessel. In other words, the intersection alignment processing section 245 has basically the same configuration as the blood vessel alignment processing section 246, and basically performs the same process except for a difference between the entire blood vessel and an intersection thereof which are biological information used for alignment.

As described above, the fundus image is an image of a living body, and thus the fundus image processing apparatus 200 makes good use of features of the image and performs alignment on the entire image by using biological information included in the fundus image. In this way, the fundus image processing apparatus 200 can realize alignment more easily and accurately.

[Configuration of Super-Resolution Processing Portion]

FIG. 9 is a block diagram illustrating a main configuration example of the super-resolution processing portion 213. In this case, alignment is performed by the biological information alignment processing portion 212, and thus the super-resolution processing portion 213 performs blurring removal and superimposition on an input image.

As illustrated in FIG. 9, the super-resolution processing portion 213 includes a PSF (Point Spread Function) estimation section 301, a blurring removal processing section 302, and a superimposition processing portion 303.

The PSF estimation section 301 estimates a PSF (Point Spread Function) by using the blood vessel extraction result supplied from the biological information alignment processing portion 212 (process 311 of FIG. 10). The estimation of a PSF is performed, for example, using a method as illustrated in FIG. 11.

In other words, the PSF estimation section 301 holds models of pixel values of the edge periphery which are obtained from a Gauss distribution in advance as illustrated in the rectangle 332 of FIG. 11. The PSF estimation section 301, as illustrated in the rectangle 331, specifies an edge part from the aligned blood vessel extraction result 322, extracts pixel values of each edge periphery, collates the pixel values with the held models, and specifies a matching or similar model. In addition, the PSF estimation section 301 supplies the most present model of the specified models to the blurring removal processing section 302 as an estimated PSF.

The blurring removal processing section 302 removes blurring from the aligned input image in a method corresponding to the model by using the estimation information of the PSF supplied from the PSF estimation section 301. In other words, the blurring removal processing section 302 removes blurring in a method corresponding to a blurring way (point spread pattern) of the image.

The blurring removal processing section 302 removes blurring by using, for example, a Wiener filter. In addition, as disclosed in "High-quality Motion Deblurring from a Single Image", Qi Shan, Jiava Jia, Aseem Agarwala, 2008 (hereinafter, referred to as NPL 4), a method of removing motion blurring may be used.

The blurring removal processing section 302 supplies the input image from which blurring has been removed to the superimposition processing portion 303.

The superimposition processing portion 303 supplementarily incorporates the input image (the input image having undergone the alignment and blurring removal) supplied from the blurring removal processing section 302 into the previous super-resolution result image supplied from the super-resolution result image buffer 214 so as to superimpose both the images, outputs the superimposition result as a new super-resolution result image, stores or outputs the new super-resolution result image in the storage unit 103 or to an external device from the output unit 104, and stores the new super-resolution result image in the super-resolution result image buffer 214.

The fundus image is captured by reducing a light amount of irradiation light as described above, and is thus basically a dark, red and approximately uniform image as a whole. In addition, a subject may be moved at the time of imaging. Therefore, focusing is not easy, and thus defocusing (so-called out of focus) tends to occur. Further, the entire image is substantially uniform, and a blurring state tends to be uniform.

Therefore, as described above, the super-resolution processing portion 213 removes blurring efficiently by removing blurring using the PSF estimation result, thereby easily obtaining a fundus image with higher image quality.

In addition, for example, the PSF estimation section 301 may determine a blurring state of an edge part and applies a PSF corresponding to the blurring state as disclosed in JP-A-2009-169943 (hereinafter, referred to as PTL 5).

In addition, the superimposition processing portion 303 may increase the resolution by performing down-sampling or up-sampling in the same manner as the case in FIG. 1 when superimposing the input image and the previous super-resolution result image.

In addition, more strictly, the fundus has a spherical shape. In addition, the optic nerve head rises as compared with the periphery thereof, and thus the fundus also has irregularities. Therefore, for example, there is a high probability that a blurring state may be different depending on the regions since some regions of the fundus are focused, and other regions are not focused.

Therefore, the PSF estimation section 301 may estimate a PSF for each predetermined partial region of the fundus image, and the blurring removal processing section 302 may remove blurring by setting a filter function for each partial region on the basis of the estimation result. That is to say, blurring may be removed with a filter function according to a location (region) or a pattern of the fundus image (methods (for example, a filter function) of removing blurring may be different depending on a position of a region or a shape of the fundus).

In this way, blurring can be removed more accurately, and thus the fundus image processing apparatus 200 can obtain a fundus image with higher image quality.

[Flow of Fundus Image Generation Process]

Next, each process performed by the fundus image processing apparatus 200 will be described. First, an example of the flow of the fundus image generation process will be described with reference to a flowchart of FIG. 12.

When the fundus image generation process starts, the respective processes in steps S201 to S204 are performed in the same manner as the respective processes in steps S101 to S104 of FIG. 2. However, in step S203, an initial image is stored in the super-resolution result image buffer 214. In addition, in step S204, a captured image which has not been processed is selected singly as an input image.

When a process target is set, the biological information alignment processing portion 212 performs a biological information alignment process in step S205. In step S206, the super-resolution processing portion 213 performs a super-resolution process by using the alignment result.

In step S207, the super-resolution processing portion 213 outputs a new super-resolution result image obtained through the super-resolution process to the storage unit 103 or the output unit 104, and stores the new super-resolution result image in the super-resolution result image buffer 214.

In step S208, the input image buffer 111 determines whether or not all the captured images have been processed, and, if there are captured images which have not been processed, the input image buffer returns the process to step S204 so as to execute the subsequent processes.

If it is determined that all the captured images have been processed in step S208, the input image buffer 111 finishes the fundus image generation process.

[Flow of Biological Information Alignment Process]

Next, with reference to a flowchart of FIG. 13, a description will be made of an example of the flow of the biological information alignment process executed in step S205 of FIG. 12.

When the biological information alignment process starts, the input image blood vessel extraction section 241 extracts an image of a blood vessel part from the input image in step S221. In step S222, the super-resolution result image blood vessel extraction section 242 extracts an image of a blood vessel part from the previous super-resolution result image.

In step S223, the biological information alignment processing portion 212 determines whether or not to perform intersection alignment. If it is determined that intersection alignment is performed, the biological information alignment processing portion 212 makes the process proceed to step S224.

In step S224, the input image intersection extraction section 243 extracts an intersection from the blood vessel extraction result of the input image. In step S225, the super-resolution result image intersection extraction section 244 extracts an intersection from the blood vessel extraction result of the previous super-resolution result image.

In step S226, the intersection alignment processing section 245 aligns the intersections with each other by using the intersection extraction results generated in steps S224 and S225.

When the intersection alignment is completed, the intersection alignment processing section 245 makes the process proceed to step S227. In addition, if it is determined that the intersection alignment is not performed in step S224, the process proceeds to step S227.

In step S227, the blood vessel alignment processing section 246 aligns the blood vessels with each other.

When the process in step S227 is completed, the blood vessel alignment processing section 246 finishes the biological information alignment process and returns the process to step S205 of FIG. 12 so as to execute the subsequent processes from step S206.

[Flow of Blood Vessel Alignment Process]

Next, with reference to a flowchart of FIG. 14, a description will be made of an example of the flow of the blood vessel alignment process executed in step S227 of FIG. 13.

When the blood vessel alignment process starts, in step S241, the superimposition processing component 271 determines whether or not the intersection alignment has been performed, and, if it is determined that the intersection alignment has been performed, the process proceeds to step S242 where the intersection alignment result is set as a superimposition result, and the blood vessel extraction result extracted in the input image blood vessel extraction section 241 and the blood vessel extraction result extracted in the super-resolution result image blood vessel extraction section 242 are superimposed according to the superimposition result, and the process proceeds to step S244.

In step S241, if it is determined that the intersection alignment has not been performed, the superimposition processing component 271 makes process proceed to step S243 and superimposes the blood vessel extraction result extracted in the input image blood vessel extraction section 241 on the blood vessel extraction result extracted in the super-resolution result image blood vessel extraction section 242, and the process proceeds to step S244.

In step S244, the shift processing component 272 performs shift alignment of shifting the blood vessel extraction result of the input image. In step S245, the extension processing component 273 performs extension alignment of extending or contracting the blood vessel extraction result of the input image. In step S246, the rotation processing component 274 performs rotation alignment of rotating the blood vessel extraction result of the input image. In step S247, the enlargement and reduction processing component 275 performs enlargement and reduction alignment of enlarging or reducing the blood vessel extraction result of the input image.

In step S248, the convergence determination component 276 determines whether or not the alignment converges, and returns the process to step S244 so as to perform the subsequent processes if it is determined that the alignment does not converge. If it is determined that the alignment converges in step S248, the convergence determination component 276 aligns the input images with each other on the basis of the alignment result and outputs the aligned input images and the blood vessel extraction result to the super-resolution processing portion 213 in step S249.

When the process in step S249 is completed, the convergence determination component 276 finishes the blood vessel alignment process, returns the process to step S227 of FIG. 13 so as to finish the biological information alignment process, and returns the process to step S205 of FIG. 12 so as to execute the subsequent processes from step S206.

In addition, the intersection alignment process executed in step S226 of FIG. 13 is performed in the same manner as the blood vessel alignment process described with reference to FIG. 14 except that an intersection of blood vessels is used for alignment instead of the entire blood vessel.

[Flow of Super-Resolution Process]

Next, with reference to a flowchart of FIG. 15, a description will be made of the flow of the super-resolution process executed in step S206 of FIG. 12.

When the super-resolution process starts, the PSF estimation section 301 estimates a point spread function (PSF) by using the blood vessel extraction result in step S261. In step S262, the blurring removal processing section 302 removes blurring from the aligned input image by using the estimated point spread function.

In step S263, the superimposition processing portion 303 superimposes the aligned input image from which blurring has been removed on a previous super-resolution result and outputs the superimposition result as a new super-resolution result image.

When the process in step S263 is completed, the superimposition processing portion 303 finishes the super-resolution process, and returns the process to the step S206 of FIG. 12 so as to execute the subsequent processes from step S207.

As described above, by executing the respective processes, the fundus image processing apparatus 200 can suppress an increase in a load on a subject and obtain a captured image of the subject with higher image quality.

3. Third Embodiment

Configuration of Fundus Image Processing Apparatus

FIG. 3 is a block diagram illustrating another configuration example of the fundus image processing apparatus. The fundus image processing apparatus 400 illustrated in FIG. 3 generates a fundus image with higher image quality by using biological information (information regarding a blood vessel, the optic nerve head, and the like) for a tone reproduction process or a super-resolution process.

The fundus image processing apparatus 400 is the same apparatus as the fundus image processing apparatus 200 of FIG. 3, has basically the same configuration as the fundus image processing apparatus 200, and performs the same process. However, the fundus image processing apparatus 400 includes an image processing unit 402 instead of the image processing unit 202 included in the fundus image processing apparatus 200.

The image processing unit 402 has basically the same configuration as the image processing unit 202 and performs the same process, but includes a noise reduction processing portion 413, a noise reduction result image buffer 414, a tone reproduction processing portion 415, and a super-resolution processing portion 416 instead of the super-resolution processing portion 213 and the super-resolution result image buffer 214 included in the fundus image processing apparatus 200.

In other words, as illustrated in the rectangle 431 of FIG. 17, the image processing unit 402 reduces a light amount and generates a plurality of fundus images 222 by imaging the fundus of the eye 221 multiple times. As illustrated in the rectangle 432 of FIG. 17, the input image buffer 111 stores a plurality of dark fundus images 222 with low image quality, and supplies the fundus images 222 to the biological information alignment processing portion 212 one by one on the basis of a request of the biological information alignment processing portion 212 or at a predetermined timing.

The biological information alignment processing portion 212 aligns the fundus images 222 with the super-resolution result image by using information of the eye (biological information) as illustrated in the rectangle 233 of FIG. 17. The noise reduction processing portion 413, as illustrated in the rectangle 434 of FIG. 17, superimposes the aligned fundus images 222 (input images) so as to perform noise reduction or enlargement of a dynamic range (noise reduction and wide dynamic range process). These processes are repeatedly performed using the noise reduction result image buffer 414, and thereby a single fundus image is generated from a plurality of fundus images with low image quality.

The generated single fundus image undergoes a tone reproduction process (Tone Reproduction) 435 (FIG. 17) in the tone reproduction processing portion 415. A method of performing the tone reproduction process 435 may use any method. For example, the tone reproduction process 435 may be performed using a method disclosed in JP-A-2009-177558 (hereinafter, referred to as PTL 6).

In addition, setting of parameters for calculating a tone curve in the tone reproduction process 435 is performed so as to be suitable for features as a living body so as to obtain a brighter image with higher image quality.

The fundus image corrected by the tone reproduction process 435 undergoes a super-resolution process 436 (FIG. 17) in the super-resolution processing portion 416. A method of performing the super-resolution process 436 may use any method. For example, the super-resolution process 436 may be performed using a method disclosed in JP-A-2010-102696 (hereinafter, referred to as PTL 7) or a method disclosed in JP-A-2010-103981 (hereinafter, referred to as PTL 8). However, the super-resolution process 436 is performed according to features as a living body so as to obtain an image with less noise and higher resolution.

In other words, the image processing unit 402 performs processes according to the features as a living body and thereby generates a single fundus image with higher image quality and high resolution from a plurality of fundus images with low image quality.

As such, in the image processing unit 402, the tone reproduction process and the super-resolution process are performed (on the generated single fundus image) after images are superimposed.

As described above, the noise reduction processing portion 413 superimposes the fundus image aligned by the biological information alignment processing portion 212 on the image of the previous superimposition result (that is, the noise reduction result) held in the noise reduction result image buffer 414 so as to enlarge a dynamic range, thereby reducing noise. A method of reducing noise through superimposition of images may use any method, and, for example, a method disclosed in JP-A-2008-294601 (hereinafter, referred to as PTL 9) or JP-A-2009-165168 (hereinafter, referred to as PTL 10) may be used.

The noise reduction result image buffer 414 includes any recording medium such as, for example, a hard disk, a flash memory, or a RAM, and stores the noise reduction result image (the superimposition result image) generated by the noise reduction processing portion 413, and supplies the noise reduction result image to the biological information alignment processing portion 212 or the noise reduction processing portion 413 on the basis of a request of the biological information alignment processing portion 212 or the noise reduction processing portion 413, or at a predetermined timing.

In other words, alignment by the biological information alignment processing portion 212 or superimposition by the noise reduction processing portion 413 is repeatedly performed. The biological information alignment processing portion 212 and the noise reduction processing portion 413 set each of a plurality of fundus images accumulated in the input image buffer 111 as a process target, and aligns or superimposes the process target image with or on a previous process result. In this way, a plurality of images obtained through imaging in the imaging unit 101 are all processed, and thereby a single fundus image is generated.

[Tone Reproduction Processing Portion]

FIG. 18 is a block diagram illustrating a main configuration example of the tone reproduction processing portion. As illustrated in FIG. 18, the tone reproduction processing portion 415 includes an image buffer 451, a parameter setting section 452, a tone curve calculation section 453, and a mapping section 454.

The image buffer 451 includes any recording medium such as, for example, a hard disk, a flash memory, or a RAM, and stores a fundus image supplied from the noise reduction processing portion 413. The image buffer 451 supplies the fundus image to the parameter setting section 452 or the mapping section 454 on the basis of a request of the parameter setting section 452 or the mapping section 454, or at a predetermined timing.

The parameter setting section 452 sets parameters for calculating a tone curve used for the tone reproduction process on the basis of features as a living body of the fundus image supplied from the image buffer 451. The tone curve is a curve for correcting grayscales of luminance values, for example, as illustrated in FIG. 19.

In addition, the transverse axis direction of the graph of FIG. 19 indicates a logarithmic value of input luminance before a grayscale is corrected, and the longitudinal axis direction indicates a logarithmic value of output luminance after a grayscale is corrected using the tone curve CL.

The fundus image undergoes grayscale correction according to the tone curve so as to be brighter in the tone reproduction process. At this time, occurrence of noise or blown out highlights is preferably suppressed as much as possible. In other words, the parameter setting section 452 reduces noise as much as possible so as to suppress occurrence of blown out highlights as much as possible, and sets parameters according to the features as a living body included in the fundus image so as to obtain a tone curve for grayscale correction where the fundus image becomes brighter.

For example, the fundus image includes an image of a part as a living body such as a blood vessel, a nerve, or the optic nerve head, and the image of each part has different features. For example, generally, an edge component tends to appear in a part such as a blood vessel or a nerve so as to be stronger than in the periphery. In addition, for example, the optic nerve head tends to be white. Further, for example, the fringe portion (a portion closer to an end of the fundus) of the fundus tends to be darker than the central portion thereof.

As such, the fundus image is an image including a feature of each part of the fundus as a living body. Therefore, the parameter setting section 452 sets parameters so as to obtain a more preferable tone curve (suppressing occurrence of noise or white and allowing an image to be as bright as possible) in consideration of the feature of each part.

Any parameter may be used as long as the parameter is used to calculate a tone curve. For example, the parameter may be a setting value of a level where an input or an output of the tone reproduction process is regarded as noise.

The parameter setting section 452 supplies a parameter, of which a value is set, to the tone curve calculation section 453. The tone curve calculation section 453 calculates a tone curve by using the parameter supplied from the parameter setting section 452, so as to be supplied to the mapping section 454. For example, the tone curve calculation section 453 sets control points (P1 to P9 in a case of the example in FIG. 19) of the tone curve CL illustrated in FIG. 19, and supplies the control points to the mapping section 454. In this case, a shape of the tone curve CL for each process target pixel is defined by obtaining an output luminance value (tone curve value) with respect to each input luminance value through a B-spline interpolation process on the basis of the control point P1 to the control point P9.

The mapping section 454 maps (corrects) the fundus image supplied from the image buffer 451 by using the tone curve supplied from the tone curve calculation section 453. The mapping section 454 supplies the corrected fundus image to the super-resolution processing portion 416.

[Parameter Setting Section]

FIG. 20 is a block diagram illustrating a main configuration example of the parameter setting section 452. As illustrated in FIG. 20, the parameter setting section 452 includes an adjustment target parameter selection component 461, a parameter initial value storage component 462, a parameter storage component 463, a brightness-value-before-correction calculation component 464, and a brightness value storage component 465. In addition, the parameter setting section 452 includes a part recognition component 466, a parameter adjustment component 467, a tone curve calculation component 468, a mapping component 469, a part checking component 470, a brightness-value-after-correction calculation component 471, a comparison component 472, and a data output component 473.

The adjustment target parameter selection component 461 selects a parameter to be adjusted this time. For example, in a case where there are a plurality of parameters for calculating a tone curve, the parameter setting section 452 may adjust all of the parameters at one time or may perform a plurality of adjustments. For example, the parameter setting section 452 may adjust each parameter once. In addition, for example, the parameter setting section 452 may prepare a plurality of sets of combinations of parameter values, may define a combination of optimal parameter values for each set, and may obtain a combination of optimal parameter values of the selected combinations of optimal parameter values of the respective sets.

The parameter initial value storage component 462 includes any recording medium such as, for example, a hard disk, a flash memory, a RAM or a ROM (Read Only Memory), and stores an initial value of a parameter (each initial value in a case where there are a plurality of parameters) necessary to calculate a tone curve. This initial value is any value and is predefined.

The parameter storage component 463 includes any recording medium such as, for example, a hard disk, a flash memory, or a RAM, and acquires an initial value of the parameter (adjustment target parameter) selected by the adjustment target parameter selection component 461 from the parameter initial value storage component 462 and stores the initial value therein.

In addition, the parameter storage component 463 updates a value of a held adjustment target parameter by using a value supplied from the comparison component 472. In other words, the parameter storage component 463 stores a value of an adjustment target parameter supplied from the comparison component 472.

In addition, the parameter storage component 463 supplies a value held at that time point to the parameter adjustment component 467 on the basis of a request from the parameter adjustment component 467 or at a predetermined timing. Further, in a case where there is a non-adjustment target parameter which is not an adjustment target, the parameter storage component 463 supplies not only a value of the adjustment target parameter but also a value of the non-adjustment target parameter to the parameter adjustment component 467.

In a case where a value of a non-adjustment target parameter is not stored, the parameter storage component 463 acquires and stores a value of the non-adjustment target parameter from the parameter initial value storage component 462 so as to be supplied to the parameter adjustment component 467. In addition, since a value of a non-adjustment target parameter acquired from the parameter initial value storage component 462 in the past is already stored in the parameter storage component 463, the parameter storage component 463 supplies the value to the parameter adjustment component 467. Further, since a value of a non-adjustment target parameter (a parameter which was an adjustment target in the past and is a non-adjustment target this time) adjusted in the past is already stored in the parameter storage component 463, the parameter storage component 463 supplies the adjusted value to the parameter adjustment component 467.

In addition, the parameter storage component 463 supplies a value (a value held at that time point) of each parameter to the data output component 473 on the basis of a request of the data output component 473 or at a predetermined timing.

The brightness-value-before-correction calculation component 464 calculates a brightness value which is a parameter indicating the brightness of a fundus image (a single fundus image which is generated by superimposing a plurality of fundus images) supplied from the noise reduction processing portion 413. The brightness value may be any content (calculation method) as long as it can indicate the brightness of an image. For example, the brightness value may use a sum total, an average value, or the like of luminance values of the entire image or a part thereof. In addition, for example, an image may be divided into a plurality of regions, a sum total of luminance values may be calculated each region, each value may be multiplied by a weight coefficient defined for each region, and a sum total of the respective multiplication results may be used as the brightness value.

The brightness-value-before-correction calculation component 464 supplies the calculated brightness value to the brightness value storage component 465 so as to be stored. The brightness value storage component 465 includes any recording medium such as, for example, a hard disk, a flash memory, or a semiconductor memory, and stores a brightness value supplied from the brightness-value-before-correction calculation component 464 or the comparison component 472. For example, the brightness value storage component 465 stores a brightness value of the fundus image before being corrected, supplied from the brightness-value-before-correction calculation component 464, and stores a brightness value (updates the held brightness value) when the brightness value of the fundus image after being corrected, calculated by the brightness-value-after-correction calculation component 471, is supplied from the comparison component 472.

The brightness value storage component 465 supplies the held brightness value to the comparison component 472 on the basis of a request of the comparison component 472 or at a predetermined timing.

The part recognition component 466 analyzes the fundus image (a single fundus image generated by superimposing a plurality of fundus images) supplied from the noise reduction processing portion 413, and recognizes parts as living bodies (fundus) such as, for example, a blood vessel, a nerve, and the optic nerve head, included in the fundus image.

Any part recognition method (image analysis method) may be used. For example, the same method as the blood vessel extraction method performed by the biological information alignment processing portion 212 may be used. For example, there may be a use of a method disclosed in NPL 2, or "Recognition of Optic Nerve Head Using Blood-Vessel-Erased Image and Its Application to Production of Simulated Stereogram in Computer-Aided Diagnosis System for Retinal Images", Toshiaki NAKAGAWA, Yoshinori HAYASHI, Yuji HATANAKA, Akira AOYAMA, Yutaka MIZUKUSA, Akihiro FUJITA, Masakatsu KAKOGAWA, Takeshi HARA, Hiroshi FUJITA, and Tetsuya YAMAMOTO, 2006 (hereinafter, referred to as NPL 5).

For example, in relation to a blood vessel or a nerve, a strong edge component is detected at a border with the periphery thereof. In addition, for example, the optic nerve head tends to be white which has higher luminance than the periphery. Further, a shape or a size is restricted to an extent.

The part recognition component 466 specifies each part included in the fundus image, for example, by using these features in an image.

When the part as a living body included in the fundus image is specified, the part recognition component 466 supplies information indicating a region of each specified part, that is, for example, at which positions a blood vessel, a nerve, the optic nerve head, and the like are respectively located in the image, to the part checking component 470.

The parameter adjustment component 467 adjusts the value of the parameter read from the parameter storage component 463 by using a predetermined method set in advance. For example, the parameter adjustment component 467 increases or decreases the value of the parameter by a predetermined amount. The parameter adjustment component 467 supplies the adjusted value to the tone curve calculation component 468 along with the value of the non-adjustment target parameter.

The tone curve calculation component 468 calculates a tone curve by using the supplied parameter in the same manner as the tone curve calculation section 453, and supplies information indicating the calculated tone curve and the adjustment target parameter to the mapping component 469.

The mapping component 469 performs grayscale correction on a luminance value of the fundus image (a single fundus image generated by superimposing a plurality of fundus images) supplied from the noise reduction processing portion 413 by using the calculated tone curve supplied from the tone curve calculation component 468 in the same manner as the mapping section 454. The mapping component 469 supplies the corrected image and the adjustment target parameter supplied from the tone curve calculation component 468, to the part checking component 470.

The part checking component 470 specifies each part included in the corrected image supplied from the mapping component 469 by using the information indicating the region of each part supplied from the part recognition component 466, and checks an image of each part in a method according to a feature of the image of each part. That is to say, the part checking component 470 checks an image of each part included in the corrected image in a method defined for the part such that appropriate grayscale correction is performed on any part in consideration of a difference between the features of the images of the respective parts.

For example, generally, an image tends to be dark in the fringe portion of the fundus. In other words, a noise component tends to increase in the fringe portion of the fundus. Therefore, the part checking component 470 checks whether or not a noise component exceeds a predetermined allowable amount, for example, in the fringe portion of the fundus, and, if the noise component is equal to or less than the allowable amount, the image is acceptable, and, if the noise component exceeds the allowable amount, the image is unacceptable.

In addition, generally, an image of the optic nerve head tends to be relatively bright. In other words, if the fundus image is made to be bright, blown out highlights tend to occur in the optic nerve head. Therefore, the part checking component 470 checks whether or not blown out highlights occur, for example, in the optic nerve head, and if blown out highlights do not occur, the image is acceptable, and if blown out highlights occur, the image is unacceptable.

As such, the checking contents of the respective parts are independent from each other. In addition, any checking content of each part or any criterion on determination of acceptance may be used. For example, in addition to the above-described examples, a frequency component may be checked, or whether or not a luminance value lower than a predetermined level is detected may be checked. Further, a plurality of items may be checked for a single part.

The part checking component 470 supplies the determination result for each part to the brightness-value-after-correction calculation component 471 along with the corrected image and the adjustment target parameter supplied from the mapping component 469.

The brightness-value-after-correction calculation component 471 calculates a brightness value of the corrected image in a case where all the checking results of the respective parts are acceptable in the part checking component 470. A method of calculating the brightness value is the same as the method of calculating a brightness value of the image before being corrected by the brightness-value-before-correction calculation component 464.

When the brightness value is calculated, the brightness-value-after-correction calculation component 471 supplies the calculated brightness value and the adjustment target parameter supplied from the part checking component 470 to the comparison component 472. In addition, in a case where unacceptable results are included in the checking results of respective parts by the part checking component 470, the brightness-value-after-correction calculation component 471 supplies the checking result to the comparison component 472.

When the brightness value of the corrected image is acquired from the brightness-value-after-correction calculation component 471, the comparison component 472 acquires a brightness value held in the brightness value storage component 465 and compares them with each other.

In a case where the brightness value supplied from the brightness-value-after-correction calculation component 471 is greater than the brightness value supplied from the brightness value storage component 465, the comparison component 472 supplies the adjustment target parameter supplied from the brightness-value-after-correction calculation component 471 to the parameter storage component 463 so as to be stored (a value of the held adjustment target parameter is updated). In addition, in this case, the comparison component 472 supplies the brightness value supplied from the brightness-value-after-correction calculation component 471 to the brightness value storage component 465 so as to be stored (a brightness value held by the brightness value storage component 465 is updated).

As such, the adjustment of each parameter is repeatedly performed through the loop of the parameter storage component 463 to the comparison component 472 (a loop process is performed). In other words, for example, the parameter initial value storage component 462 stores such a value where the fundus image is the darkest as an initial value of the parameter, the parameter adjustment component 467 adjusts a value of the adjustment target parameter such that the fundus image becomes brighter, the tone curve calculation component 468 and the mapping component 469 correct the fundus image by using the adjusted value, and the part checking component 470 to the comparison component 472 check the corrected image. In a case where a checking result for each part is acceptable and a brighter image is obtained, the loop process becomes more complex.

In addition, in a case where a checking result for each part is unacceptable, in a case where a brighter image is unable to be obtained even if a checking result for each part is acceptable, that is, a checking result which is found unacceptable by the part checking component 470 is supplied via the brightness-value-after-correction calculation component 471, or in a case where the brightness value supplied from the brightness-value-after-correction calculation component 471 is not greater than a brightness value supplied from the brightness value storage component 465, the comparison component 472 notifies the data output component 473 thereof (information of the parameter storage component 463 and the brightness value storage component 465 is not updated).

For example, in a case where a parameter which leads to a brighter fundus image as a value thereof becomes greater is set as an adjustment target parameter, the parameter initial value storage component 462 stores the minimum value of the parameter as an initial value, and the parameter adjustment component 467 increases a value of the input parameter by a predetermined amount.

In addition, in a case where a parameter which leads to a brighter fundus image as a value thereof becomes smaller is set as an adjustment target parameter, the parameter initial value storage component 462 stores the maximum value of the parameter as an initial value, and the parameter adjustment component 467 decreases a value of the input parameter by a predetermined amount.

In addition, any initial value of a parameter or any adjustment method may be used, and values or methods other than the above-described examples may be used. For example, the best image may be selected out of all of the corrected images obtained by correcting all values (or representative values) taken by parameters used for the tone reproduction process, and a value of each parameter corresponding to the image may be selected as the best value. In this case, checking of each part and calculation of a brightness value are performed with respect to all the corrected images obtained, all checking results and brightness values are evaluated, and a value of each parameter which is acceptable in the checking of each part and leads to the brightest image is selected as the best value.

In addition, whether or not an image becomes brighter may be determined simply based on which brightness value is greater, or may be determined based on other criterions. For example, it may be determined that an image becomes brighter through the present correction only in a case where a brightness value of the image after the present correction is greater than a brightness value before the present correction by a predetermined amount or more. In addition, for example, it may be determined that an image becomes brighter through the present correction only in a case where, even if a brightness value of the image after the present correction is smaller than a brightness value before the present correction, it is in a predetermined range set in advance.

In a case where a notification of the unacceptance of a checking result by the part checking component 470 is sent, or a notification that an image after the present grayscale correction is not brighter than an image before the present grayscale correction is sent from the comparison component 472, the data output component 473 sends the notification thereof to the adjustment target parameter selection component 461, so as to select another parameter as an adjustment target parameter. That is to say, an adjustment of another parameter starts.

When parameters to be adjusted are all adjusted in this way, the data output component 473 acquires values of the respective parameters stored in the parameter storage component 463 so as to be supplied to the super-resolution processing portion 416.

By setting values of the respective parameters as described above, the parameter setting section 452 can set a value of each parameter to a value with which defects such as occurrence of noise or white can be suppressed and a brighter image can be obtained. In other words, the tone reproduction processing portion 415 can more appropriately perform the tone reproduction process according to features of an image as a living body.

[Super-Resolution Processing Portion]

FIG. 21 is a block diagram illustrating a main configuration example of the super-resolution processing portion 416 of FIG. 16.

As illustrated in FIG. 21, the super-resolution processing portion 416 includes a learning dictionary storage section 481, an image processing section 482, a part recognition section 483, a part evaluation criterion storage section 484, a part image evaluation section 485, and an image selection section 486.

The learning dictionary storage section 481 includes any recording medium such as, for example, a hard disk, a flash memory, or a semiconductor memory, and stores a plurality of learning dictionaries showing learning methods performed in a super-resolution process. The learning dictionary storage section 481 supplies each learning dictionary to the image processing section 482 on the basis of a request of the image processing section 482 or at a predetermined timing.

The image processing section 482 performs a super-resolution process of improving the resolution through learning on a fundus image supplied from the tone reproduction processing portion 415 by using the learning dictionary supplied from the learning dictionary storage section 481. In other words, a super-resolution result image obtained through the super-resolution process performed by the image processing section 482 is different depending on a learning dictionary supplied from the learning dictionary storage section 481. The image processing section 482 performs the super-resolution process in relation to all the learning dictionaries. The image processing section 482 supplies a calculated super-resolution result image corresponding to each learning dictionary to the part recognition section 483.

The part recognition section 483 analyzes each super-resolution result image supplied, and recognizes parts as living bodies (fundus) such as, for example, a blood vessel, a nerve, and the optic nerve head, included in each super-resolution result image, in the same manner as the part recognition component 466. The part recognition section 483 recognizes each part using, for example, the method disclosed in NPL 2 or NPL 4.

When the part as a living body included in each super-resolution result image is specified, the part recognition section 483 supplies information indicating a region of each specified part, that is, for example, at which positions a blood vessel, a nerve, the optic nerve head, and the like are respectively located in the image, to the part image evaluation section 485 along with a super-resolution result image corresponding to the information.

The part evaluation criterion storage section 484 includes any recording medium such as, for example, a hard disk, a flash memory, a RAM or a ROM, and stores information (for example, how to evaluate what kind of information of which portion on the fundus image) indicating an evaluation method of an image of each part or a criterion thereof performed by the part image evaluation section 485.

The part evaluation criterion storage section 484 supplies the held information indicating a criterion of evaluation of an image of each part to the part image evaluation section 485 on the basis of a request of the part image evaluation section 485 or at a predetermined timing.

The part image evaluation section 485 evaluates the image of each part recognized by the part recognition section 483 of each super-resolution result image by using the information indicating a criterion of image evaluation supplied from the part evaluation criterion storage section 484.

For example, the part image evaluation section 485 analyzes a frequency component of an image of a blood vessel with respect to each super-resolution result image, and evaluates a high frequency component amount (the spectral magnitude of a predetermined frequency band component) included in the image of a blood vessel and whether or not the high frequency component amount is included in a predetermined target range set in advance.

In addition, for example, the part image evaluation section 485 analyzes a frequency component of an image of a flat portion such as the fringe portion with respect to each super-resolution result image, and evaluates whether a noise component amount (the spectral magnitude of a predetermined frequency band component) included in the image of the flat portion is small.

The part image evaluation section 485 supplies the evaluation result of each part obtained in this way with respect to each super-resolution result image, to the image selection section 486 along with the super-resolution result images.

The image selection section 486 selects an optimal super-resolution result image from the super-resolution result image group supplied from the part image evaluation section 485 on the basis of the image evaluation results supplied from the part image evaluation section 485. For example, the image selection section 486 selects a super-resolution result image of which the high frequency component of the image of a blood vessel is as large as possible in a predetermined target range set in advance and the noise component of the image of the flat portion is as small as possible.

In addition, any image selection method or image selection criterion may be used. For example, an image may be selected based only on an evaluation result of an image of a blood vessel or may be selected in consideration of evaluation results other than the above-described evaluation results.

As described above, the image selection section 486 selects an optimal super-resolution result image from a plurality of super-resolution result images generated using different learning dictionaries. That is to say, the image selection section 486 selects a learning dictionary where a super-resolution result image becomes the most favorable.

The image selection section 486 outputs the selected super-resolution result image to an external unit (the storage unit 103 or the output unit 104) of the image processing unit 402.

As such, the super-resolution processing portion 416 can perform the super-resolution process accompanied by learning by using different learning dictionaries, perform image evaluation for each part as a living body with respect to each super-resolution result image, and select super-resolution result image generated using an optimal learning dictionary on the basis of the evaluation result.

Generally, an appropriate learning dictionary used for the super-resolution process is different depending on image content. In other words, an optimal learning dictionary for a certain image may not be the optimum for other images. However, the super-resolution processing portion 416 evaluates a generated super-resolution result image as described above, and thus can select an optimal learning dictionary for any fundus image. In addition, the super-resolution processing portion 416 performs image evaluation for each part as a living body (fundus) and thus can select a more appropriate learning dictionary.

In other words, the super-resolution processing portion 416 can obtain a fundus image with a smaller noise component and higher resolution (a fundus image with higher image quality and high resolution).

[Flow of Fundus Image Generation Process]

Next, with reference to a flowchart of FIG. 22, a description will be made of an example of the flow of the fundus image generation process performed by the fundus image processing apparatus 400.

When the fundus image generation process starts, the imaging unit 101 reduces a light amount and performs a plurality of imagings of the fundus in step S401 in the same manner as in the case in step S201 of FIG. 12. In step S402, the input image buffer 111 stores captured images (fundus images) obtained through the imaging in step S401 in the same manner as in the case in step S202 of FIG. 12.

In step S403, the noise reduction result image buffer 414 stores an initial captured image as an initial image in the same manner as in the case in step S203 of FIG. 12.

In step S404, the biological information alignment processing portion 212 selects one of the captured images, stored in the input image buffer 111, which have not been processed, in the same manner as in the case in step S204 of FIG. 12. In step S405, the biological information alignment processing portion 212 performs an alignment process (biological information alignment process) using biological information of the captured image (fundus image) selected in step S404 and a captured image (fundus image) which is supplied from the noise reduction result image buffer 414 and is a previous superimposition result in the same manner as in the case in step S205 of FIG. 12. Details of the biological information alignment process are basically the same as those described with reference to the flowcharts of FIGS. 13 and 14, and thus description thereof will be omitted.

In step S406, the noise reduction processing portion 413 superimposes both the captured images (fundus images) aligned through the process in step S405 so as to reduce noise.

In step S407, the noise reduction processing portion 413 determines whether or not all the captured images (fundus images) have been processed. If it is determined that there is an unprocessed captured image in the input image buffer 111, the noise reduction processing portion 413 makes the process proceed to step S408.

In step S408, the noise reduction result image buffer 414 stores the noise reduction process result image obtained through the process in step S406, that is, the captured image being superimposed. When the captured image is stored, the noise reduction result image buffer 414 returns the process to step S404 and repeatedly performs the subsequent processes.

If the processes in steps S404 to S408 are repeatedly performed, and it is determined that all of the captured images have been processed in step S407, the noise reduction processing portion 413 makes the process proceed to step S409.

In step S409, the tone reproduction processing portion 415 performs a tone reproduction process on a single captured image (fundus image) generated. In step S410, the super-resolution processing portion 416 performs a super-resolution process on the image having undergone the tone reproduction process so as to obtain a fundus image with a higher resolution, and finishes the fundus image generation process.

By performing the process in this way, the fundus image processing apparatus 400 can suppress an increase in a load on a subject and obtain a captured image of the subject with higher image quality.

[Flow of Tone Reproduction Process]

Next, with reference to a flowchart of FIG. 23, a description will be made of an example of the flow of the tone reproduction process executed in step S409 of FIG. 22.

When the tone reproduction process starts in step S431, the image buffer 451 of the tone reproduction processing portion 415 stores a single captured image (fundus image) which is superimposed.

In step S432, the parameter setting section 452 sets a parameter on the basis of biological information. In step S433, the tone curve calculation section 453 calculates a tone curve by using a parameter of which a value is set through the process in step S432. In step S434, the mapping section 454 corrects a captured image (fundus image) by using the tone curve generated in step S433.

When the process in step S434 is completed, the mapping section 454 finishes the tone reproduction process, and returns the process to step S409 of FIG. 22 such that the process proceeds to step S410.

[Flow of Parameter Setting Process]

Next, with reference to a flowchart of FIG. 24, a description will be made of an example of the flow of the parameter setting process executed in step S432 of FIG. 23.

When the parameter setting process starts, the adjustment target parameter selection component 461 selects a parameter to be adjusted in step S451. In step S452, the parameter storage component 463 acquires an initial value of each parameter from the parameter initial value storage component 462 so as to be stored.

In step S453, the brightness-value-before-correction calculation component 464 calculates a brightness value of the captured image (fundus image) generated through the process in step S406 of FIG. 22. In step S454, the brightness value storage component 465 stores the brightness value calculated through the process in step S453. In step S455, the part recognition component 466 recognizes each part as a living body included in the captured image (fundus image) generated through the process in step S406 of FIG. 22.

In step S456, the parameter adjustment component 467 adjusts a value of the adjustment target parameter. In step S457, the tone curve calculation component 468 calculates a tone curve by using various parameters including the adjustment target parameter which has been adjusted. In step S458, the mapping component 469 corrects the captured image (fundus image) generated through the process in step S406 of FIG. 22 by using the tone curve calculated through the process in step S457.

In step S459, the part checking component 470 performs checking for each part as a living body recognized through the process in step S455 with respect to the captured image (fundus image) corrected through the process in step S458.

In step S460, the part checking component 470 determines whether or not all the checking results of the respective parts performed in step S459 are acceptable (that is, all conditions are satisfied). If it is determined that all the conditions are satisfied, the part checking component 470 makes the process proceed to step S461.

In step S461, the brightness-value-after-correction calculation component 471 calculates a brightness value of the captured image (fundus image) corrected in step S458. In step S462, the comparison component 472 compares the brightness values of the captured images before and after the present correction performed in step S458. In step S463, the comparison component 472 determines whether or not the brightness value of the captured image after the correction is greater.

If it is determined that the brightness value of the captured image after the correction is greater and the captured image becomes brighter through the present correction in step S458, the comparison component 472 makes the process proceed to step S464. The parameter storage component 463 stores a value of the adjustment target parameter in step S464 and after the present adjustment in step S456 (a value of the adjustment target parameter is updated).

In step S465, the brightness value storage component 465 stores the brightness value of the captured image after the present correction in step S458 (a brightness value is updated). When the process in step S465 is completed, the brightness value storage component 465 returns the process to step S456 and repeatedly performs the subsequent processes.

If it is determined that all the conditions are not satisfied in step S460, the part checking component 470 makes the process proceed to step S466. In addition, if it is determined that the brightness value of the captured image after the correction is equal to or less than the brightness value of the captured image before the correction, and the captured image does not become bright through the present correction in step S458 in step S463, the comparison component 472 makes the process proceed to step S466.

In step S466, the data output component 473 determines whether or not all the parameters to be adjusted have been processed, and, if it is determined that there is an unprocessed parameter, the process returns to step S451 such that the subsequent processes are repeatedly performed on the new unprocessed parameter. That is to say, the adjustment target parameter selection component 461 selects the unprocessed parameter as a new adjustment target parameter and executes the subsequent processes from step S452.

If it is determined that all the parameters to be adjusted have been processed in step S466, the data output component 473 makes the process proceed to step S467 and acquires and outputs the parameter stored in the parameter storage component 463. When the process in step S466 is completed, the data output component 473 finishes the parameter setting process and returns the process to step S432 of FIG. 23 so as to execute the subsequent processes from step S433.

[Flow of Super-Resolution Process]

Next, with reference to a flowchart of FIG. 25, a description will be made of an example of the flow of the super-resolution process executed in step S410 of FIG. 22.

When the super-resolution process starts, the image processing section 482 selects an unprocessed learning dictionary from the learning dictionaries stored in the learning dictionary storage section 481 in step S481. In step S482, the image processing section 482 generates an image with a high resolution by using a coefficient obtained through learning.

In step S483, the part recognition section 483 recognizes a part as a living body included in the image. In step S484, the part image evaluation section 485 evaluates the image for each part. In step S485, the part image evaluation section 485 stores the image and the evaluation result.

In step S486, the part image evaluation section 485 determines whether or not all the learning dictionaries have been processed. If it is determined that there is an unprocessed learning dictionary, the part image evaluation section 485 returns the process to step S481 such that the subsequent processes are performed on a new learning dictionary. In other words, the image processing section 482 selects a new unprocessed learning dictionary and executes the subsequent processes from step S482.

If it is determined that all the learning dictionaries have been processed in step S486, the part image evaluation section 485 makes the process proceed to step S487.

In step S487, the image selection section 486 selects a super-resolution result image which is evaluated most highly in the evaluation performed in step S484 from the super-resolution result image group generated using the respective learning dictionaries as above. When the super-resolution result image is selected, the image selection section 486 finishes the super-resolution process, returns the process to step S410 of FIG. 22, and finishes the fundus image generation process.

As described above, by performing the respective processes, the fundus image processing apparatus 400 can suppress an increase in a load on a subject and obtain a captured image of the subject with higher image quality.

[Another Configuration Example of Parameter Setting Section]

In addition, although, in the above description, a description has been made that the entire captured image (fundus image) is corrected in the parameter setting section 452, the present technology is not limited thereto, and an image of each part as a living body may be corrected separately. In this way, a process for a portion (for example, the fringe portion or the like of a captured image) which is not necessary to check each part and is not recognized as a part of the fundus included in the captured image can be omitted, and thus it is possible to reduce a load regarding parameter setting.

FIG. 26 is a block diagram illustrating a main configuration example of the parameter setting section in this case. In a case of the example illustrated in FIG. 26, the parameter setting section 452 includes a brightness-value-before-correction calculation component 564 instead of the brightness-value-before-correction calculation component 464 in the example illustrated in FIG. 20, and includes a brightness value storage component 465 instead of the brightness value storage component 465. In addition, the parameter setting section 452 illustrated in FIG. 26 includes a part recognition component 566 instead of the part recognition component 466 illustrated in FIG. 20, and includes a mapping component 569 instead of the mapping component 469.

Further, the parameter setting section 452 illustrated in FIG. 26 includes a part checking component 570 instead of the part checking component 470 in the example illustrated in FIG. 20, and includes a brightness-value-after-correction calculation component 571 instead of the brightness-value-after-correction calculation component 471. Furthermore, the parameter setting section 452 illustrated in FIG. 26 includes a comparison component 572 instead of the comparison component 472 in the example illustrated in FIG. 20.

The part recognition component 566 recognizes parts as living bodies (fundus) included in the fundus image (a single fundus image generated by superimposing a plurality of fundus images) supplied from the noise reduction processing portion 413 in the same manner as the part recognition component 466. The part recognition component 566 extracts an image of each specified part from the fundus image, and supplies the extracted image of each part to the brightness-value-before-correction calculation component 564 and the mapping component 569.

The brightness-value-before-correction calculation component 564 calculates a brightness value of the supplied image of each part in the same method as in the case of the brightness-value-before-correction calculation component 464. The brightness-value-before-correction calculation component 564 supplies the calculated brightness value of each part to the brightness value storage component 565 so as to be stored.

The brightness value storage component 565 includes any recording medium such as, for example, a hard disk, a flash memory, or a RAM, and stores the brightness value of the image of each part supplied from the brightness-value-before-correction calculation component 564 or the comparison component 572 in the same manner as in the case of the brightness value storage component 465.

The mapping component 569 performs grayscale correction on a luminance value of the image of each part supplied from the part recognition component 566 by using the calculated tone curve supplied from the tone curve calculation component 468. This correction method is the same as in the case of the mapping component 469. The mapping component 569 supplies the corrected image of each part and the adjustment target parameter supplied from the tone curve calculation component 468, to the part checking component 570.

The part checking component 570 checks the corrected image of each part supplied from the mapping component 569 in a method according to a feature of the image of the part such that appropriate grayscale correction is performed on any part in consideration of a difference between the features of the images of the respective parts. A method of checking each part is the same as in the case of the part checking component 470.

The part checking component 570 supplies the determination result for each part to the brightness-value-after-correction calculation component 571 along with the corrected image and the adjustment target parameter supplied from the mapping component 469.

The brightness-value-after-correction calculation component 571 calculates a brightness value of the corrected image of each part in a case where all the checking results of the respective parts are acceptable in the part checking component 570. A method of calculating the brightness value is the same as in the case of the brightness-value-before-correction calculation component 564. When the brightness value is calculated, the brightness-value-after-correction calculation component 571 supplies the calculated brightness value the image of each part and the adjustment target parameter supplied from the part checking component 570 to the comparison component 572.

In addition, in a case where unacceptable results are included in the checking results of the respective parts by the part checking component 570, the brightness-value-after-correction calculation component 571 supplies the checking result to the comparison component 572 in the same manner as in the case of the brightness-value-after-correction calculation component 471.

When the brightness value of the corrected image of each part is acquired from the brightness-value-after-correction calculation component 571, the comparison component 572 acquires a brightness value of an image of each part held in the brightness value storage component 565 and compares them with each other.

In relation to the image of each part, in a case where the brightness value supplied from the brightness-value-after-correction calculation component 571 is greater than the brightness value supplied from the brightness value storage component 565, the comparison component 572 supplies the adjustment target parameter supplied from the brightness-value-after-correction calculation component 571 to the parameter storage component 463 so as to be stored (a value of the adjustment target parameter held in the parameter storage component 463 is updated). In addition, in this case, the comparison component 572 supplies the brightness value of the image of each part supplied from the brightness-value-after-correction calculation component 571 to the brightness value storage component 565 so as to be stored (the latest brightness value held by the brightness value storage component 565 is updated).

Conversely, in a case where a brighter image is unable to be obtained, that is, a brightness value supplied from the brightness-value-after-correction calculation component 571 is not greater than a brightness value supplied from the brightness value storage component 565 in relation to the image of each part, the comparison component 572 notifies the data output component 473 thereof (information of the parameter storage component 463 and the brightness value storage component 565 is not updated).

In addition, the comparison component 572 may use any method of comparing brightness values of images of each part before and after the present correction. For example, before and after the present correction, the comparison component 572 may compare brightness values of images of each part, or may calculate a statistical value such as a sum total or an average value of brightness values of images of the respective parts and compare sum totals thereof. In addition, the comparison component 572 may multiply a brightness value of the image of each part by a weight coefficient for each part, calculate a sum total of the respective multiplication results, and compare sum totals thereof.

[Flow of Parameter Setting Process]

Next, with reference to a flowchart of FIG. 27, a description will be made of an example of the flow of the parameter setting process executed by the parameter setting section 452 illustrated in FIG. 26.

In this case as well, the flow of the parameter setting process is basically the same as in the case described with reference to the flowchart of FIG. 24. However, in a case of the example in FIG. 27, the part recognition component 566 recognizes each part as a living body included in the captured image in step S553 and extracts an image of each part.

In addition, in step S554, the brightness-value-before-correction calculation component 564 calculates a brightness value of the extracted image of each part, and, the brightness value storage component 565 stores each calculated brightness value in step S555.

In addition, in step S558, the mapping component 569 corrects the image of each part by using the tone curve calculated in step S557.

In addition, in step S561, the brightness-value-after-correction calculation component 571 calculates a brightness value of the corrected image of each part obtained in step S558. In step S562, the comparison component 572 compares a brightness value of the image of each part before the present correction with a brightness value of the image of each part after the present correction.

By setting values of the respective parameters as described above, the parameter setting section 452 can set a value of each parameter to a value with which defects such as occurrence of noise or white can be suppressed and a brighter image can be obtained.

In addition, a tone curve used to correct the image of each part may be set independently for each part. In other words, the parameter setting section 452 may set a parameter for each part as a living body. In this case, the tone curve calculation section 453 of FIG. 18 calculates a tone curve for every image of each part. In addition, the mapping section 454 recognizes a part as a living body included in a captured image from the captured image supplied from the image buffer 451, and extracts an image of each part. Further, the mapping section 454 corrects the extracted image of each part by using the tone curve for the part calculated by the tone curve calculation section 453.

In this way, the tone reproduction processing portion 415 can perform a more appropriate tone reproduction process according to a feature of the image as a living body.

In addition, although, in the third embodiment, a description has been made that both the tone reproduction processing portion 415 and the super-resolution processing portion 416 respectively perform processes by using biological information of a subject (information regarding the fundus), the present technology is not limited thereto, and, for example, one of the tone reproduction processing portion 415 and the super-resolution processing portion 416 may perform a process by using the biological information of the subject and the other may perform a process without using the biological information of the subject. In addition, for example, either the tone reproduction processing portion 415 or the super-resolution processing portion 416 may be omitted.

4. Fourth Embodiment

Configuration of Fundus Image Processing Apparatus

Meanwhile, as described above, the imaging unit 101 irradiates the subject with light at the time of imaging. The irradiation light in this case is visible light, and thus a light amount of the irradiation light is reduced in consideration of influence on an examinee. As a result, a fundus image captured by applying visible light is a relatively dark image.

Therefore, in the present embodiment, the imaging unit images a subject by using irradiation light including infrared light in addition to visible light. The infrared light is invisible to the human eye, and thus the imaging unit irradiates the subject with a light amount sufficient to perform alignment so as to perform imaging. Thereby, it is possible to obtain a fundus image with brightness sufficient to perform alignment. In addition, the infrared light described in the present specification is a concept in a broad sense including not only infrared light of the waveform band of approximately 700 nm to 1000 nm, generally mentioned, but also near infrared light. For example, noninvasive light by which an examinee does not feel dazzled is one kind of infrared light described in the present specification.

FIG. 28 is a diagram illustrating an outline of the present embodiment. As illustrated in the frame 600 of FIG. 28, images 621 captured by applying infrared light at a light amount sufficient to perform alignment are aligned. In addition, like the images 621, an image captured by applying infrared light is hereinafter referred to as an infrared light image. In addition, as illustrated in the frame 601, images 622 captured by applying visible light at a low light amount are aligned using the alignment result (hereinafter, referred to as alignment information) of the infrared light images 621. In addition, like the images 622, an image captured by applying visible light at a low light amount is hereinafter referred to as a visible light image. Thereby, it is possible to obtain a captured image of a subject with a higher image quality.

Configuration Fundus Image Processing Apparatus

FIG. 29 is a block diagram illustrating a configuration example of the fundus image processing apparatus. The fundus image processing apparatus 700 illustrated in FIG. 29 has basically the same configuration as the fundus image processing apparatus 200 illustrated in FIG. 3 and performs the same process. However, the fundus image processing apparatus 700 includes an imaging unit 701 and an image processing unit 702 instead of the imaging unit 101 and the image processing unit 202 included in the fundus image processing apparatus 200. Therefore, hereinafter, only the imaging unit 701 and the image processing unit 702 will be described.

The imaging unit 701 applies light including infrared light in addition to visible light to a subject and repeatedly performs a plurality of imagings of the fundus using the visible light and the infrared light together. A configuration of the imaging unit 701 will be described with reference to FIG. 30.

[Imaging Unit]

FIG. 30 is a diagram illustrating a main configuration example of the imaging unit 701. As illustrated in FIG. 30, the imaging unit 701 includes a light source 731, mirrors 732-1 to 732-3, a lens 733, a visible light imaging unit 734, an infrared light imaging unit 735, an infrared light cutoff filter 736, and a visible light cutoff filter 737.

The light source 731 includes a source of illumination which emits light at a waveform band of visible light and a waveform band of infrared light. At this time, the visible light has a relatively low light amount, and the infrared light has a light amount sufficient to perform alignment. In other words, the infrared light has a light amount larger than the visible light.

The mirrors 732-1 to 732-3 reflect or transmit visible light and infrared light therethrough.

The lens 733 forms a subject image on light sensing surfaces of the visible light imaging unit 734 and the infrared light imaging unit 735.

In other words, the visible light and the infrared light from the light source 731 are respectively reflected by the mirrors 732-1 and 732-2 so as to change their light paths, pass through the lens 733, and are incident to the fundus of the eye 221 such that the fundus is illuminated.

Reflected light of the eye 221 from the fundus, that is, a fundus image is reflected by the mirror 732-3, and is incident to the visible light imaging unit 734 and the infrared light imaging unit 735.

However, the infrared light cutoff filter 736 installed in the visible light imaging unit 734 does not transmit the infrared light and transmits only the visible light. Therefore, a fundus image of the visible light of the reflected light beams of the eye 221 from the fundus, that is, fundus images, is transmitted through the infrared light cutoff filter 736 installed in the visible light imaging unit 734 and is formed on the light sensing surface of the visible light imaging unit 734. On the other hand, a fundus image of the infrared light of the reflected light beams of the eye 221 from the fundus, that is, fundus images, is not transmitted through the infrared light cutoff filter 736 of the visible light imaging unit 734 and thus is not formed on the light sensing surface of the visible light imaging unit 734. Therefore, the visible light imaging unit 734 captures only a fundus image of the visible light, and, as a result, outputs only a visible light image.

In addition, the visible light cutoff filter 737 installed in the infrared light imaging unit 735 does not transmit the visible light and transmits only the infrared light. Therefore, a fundus image of the infrared light of the reflected light beams of the eye 221 from the fundus, that is, fundus images, is transmitted through the visible light cutoff filter 737 installed in the infrared light imaging unit 735 and is formed on the light sensing surface of the infrared light imaging unit 735. On the other hand, a fundus image of the visible light of the reflected light beams of the eye 221 from the fundus, that is, fundus images, is not transmitted through the visible light cutoff filter 737 of the infrared light imaging unit 735 and thus is not formed on the light sensing surface of the infrared light imaging unit 735. Therefore, the infrared light imaging unit 735 captures only a fundus image of the infrared light, and, as a result, outputs only an infrared light image.

The imaging unit 701 applies light including visible light and infrared light and performs a plurality of imagings of the fundus using the visible light and the infrared light together. The imaging by the imaging unit 701 is preferably performed multiple times in as short a time as possible such that the respective fundus images obtained through the imagings can be as close to each other as possible. A plurality of visible light images with relatively low image quality and a plurality of infrared light images with image quality sufficient to perform alignment, obtained through the imaging by the imaging unit 701, are supplied to the image processing unit 702.

In addition, a configuration of the imaging unit 701 is not limited to the above-described example, and may be a configuration capable of obtaining a visible light image and an infrared light image of a subject. For example, both the visible light cutoff filter 736 and the infrared light cutoff filter 737 may be disposed in imaging elements respectively included in the visible light imaging unit 734 and the infrared light imaging unit 735, and each of the visible light imaging unit 734 and the infrared light imaging unit 735 may obtain a visible light image and an infrared light image.

The image processing unit 702 aligns a plurality of infrared light images with image quality sufficient to perform alignment, supplied from the imaging unit 701. In addition, the image processing unit 702 aligns a plurality of visible light images with relatively low image quality by using alignment information (described later in detail) in the infrared light images, and then superimposes the images, thereby generating a single fundus image with higher image quality.

As illustrated in FIG. 29, the image processing unit 702 includes an input image buffer 711, an infrared light image alignment processing portion 712, an initial image buffer 713, an alignment information buffer 714, a visible light image alignment processing portion 715, a super-resolution processing portion 716, and a super-resolution result image buffer 717.

The input image buffer 711 is provided in at least a part of a region of any recording medium such as, for example, a hard disk, a flash memory, or a RAM, and stores a plurality of visible light images with relatively low image quality and a plurality of infrared light images with image quality sufficient to perform alignment, supplied from the imaging unit 701, as input images. In addition, the input image buffer 711 appropriately supplies the infrared light image to the infrared light image alignment processing portion 712 and supplies the visible light image to the visible light image alignment processing portion 715, as necessary.

The infrared light image alignment processing portion 712 performs alignment so as to align subjects between the infrared light image supplied from the input image buffer 711 and an initial image of the infrared light image supplied from the initial image buffer 713 described later, by using biological information of the subject. The infrared light image alignment processing portion 712 supplies alignment information to the alignment information buffer 714 when the alignment converges. In addition, a detailed configuration of the infrared light image alignment processing portion 712 will be described later with reference to FIGS. 31 and 32.

As the biological information used for alignment, for example, a blood vessel, a nerve, the optic nerve head, or the like may be employed. Of course, any biological information may be used, and other pieces of biological information may be used.

The initial image buffer 713 is provided in at least a part of a region of any recording medium such as, for example, a hard disk, a flash memory, or a RAM, and stores an infrared light image which is first supplied from the input image buffer 711 via the infrared light image alignment processing portion 712, as an initial image. The initial image buffer 713 appropriately supplies the initial image to the infrared light image alignment processing portion 712 as necessary.

The alignment information buffer 714 is provided in at least a part of a region of any recording medium such as, for example, a hard disk, a flash memory, or a RAM, and stores alignment information supplied from the infrared light image alignment processing portion 712.

The visible light image alignment processing portion 715 aligns images by applying the alignment information read from the alignment information buffer 714 to the visible light image supplied from the input image buffer 711. The aligned visible light image is supplied to the super-resolution processing portion 716.

The super-resolution processing portion 716 has basically the same configuration as the super-resolution processing portion 213 of FIG. 3 and performs the same process. In other words, the super-resolution processing portion 716 acquires a super-resolution result image (that is, an image obtained as a result of the super-resolution process) generated in the past from the super-resolution result image buffer 717, and performs a super-resolution process and a high dynamic range process by superimposing the super-resolution result image on the visible light image aligned by the visible light image alignment processing portion 715, thereby generating a super-resolution result image. The super-resolution processing portion 716 stores or outputs the super-resolution result image which is generated through the repetition of the alignment and the super-resolution process and has a higher resolution and a wider dynamic range in the storage unit 103 or from the output unit 104, and supplies the super-resolution result image to the super-resolution result image buffer 717 so as to be stored.

The super-resolution result image buffer 717 has basically the same configuration as the super-resolution result image buffer 214 of FIG. 3 and performs the same process. In other words, the super-resolution result image buffer 717 stores the super-resolution result image generated by the super-resolution processing portion 716, and appropriately supplies the super-resolution result image to the super-resolution processing portion 716 as necessary. In addition, the super-resolution result image buffer 717 stores a visible light image which is first supplied from the visible light image alignment processing portion 715 via the super-resolution processing portion 716, as an initial image. The super-resolution result image buffer 717 appropriately supplies the initial image to the super-resolution processing portion 716 as necessary.

[Process Performed by Image Processing Unit]

FIG. 31 is a diagram illustrating a flow of the process performed by the image processing unit 702 with this configuration. As illustrated in FIG. 31, a plurality of infrared light images 621 and a plurality of visible light images 622 captured by the imaging unit 701 are stored in the input image buffer 711. The input image buffer 711 supplies the infrared light images 621 to the infrared light image alignment processing portion 712 one by one at a predetermined timing.

As illustrated in the frame 741 of FIG. 31, the infrared light image alignment processing portion 712 performs image alignment using information of the eye (that is, biological information) on the infrared light images 621 supplied from the input image buffer 711 and the initial image supplied from the initial image buffer 713. The infrared light image alignment processing portion 712 supplies alignment information in the infrared light images to the alignment information buffer 714 when the alignment converges. Alignment information for all the infrared light images stored in the input image buffer 711 is stored in the alignment information buffer 714 through the repetition of these processes.

In addition, as illustrated in the frame 742 of FIG. 31, the visible light image alignment processing portion 715 applies the alignment information for each infrared light image read from the alignment information buffer 714 to the visible light images 622 corresponding to the respective visible light images supplied from the input image buffer 711, thereby aligning the visible light images with each other. Thereafter, the aligned visible light images are supplied to the super-resolution processing portion 716, and undergo a super-resolution process through superimposition of the images.

[Configuration of Infrared Light Image Alignment Processing Portion]

Next, a detailed configuration of the infrared light image alignment processing portion 712 will be described with reference to FIGS. 32 and 33.

FIG. 32 is a block diagram illustrating a main configuration example of the infrared light image alignment processing portion 712 of FIG. 29. As illustrated in FIG. 32, the infrared light image alignment processing portion 712 includes an infrared light image blood vessel extraction section 751, an initial image blood vessel extraction section 752, an infrared light image intersection extraction section 753, an initial image intersection extraction section 754, an intersection alignment processing section 755, and a blood vessel alignment processing section 756.

The infrared light image blood vessel extraction section 751 extracts a blood vessel part from the infrared light image supplied from the input image buffer 711 so as to be supplied to the blood vessel alignment processing section 756.

Similarly, the initial image blood vessel extraction section 752 extracts a blood vessel part from the initial image supplied from the initial image buffer 713 so as to be supplied to the blood vessel alignment processing section 756.

The blood vessel alignment processing section 756 aligns the blood vessels with each other between the infrared light image and the initial image by using the blood vessel extraction result extracted from each image, and stores the alignment information in the alignment information buffer 714.

In addition, simple alignment may be performed using a position of an intersection of the blood vessels before the alignment using the blood vessel extraction result (a shape or a position of the entire blood vessel). In this case, the infrared light image blood vessel extraction section 751 supplies the blood vessel extraction result from the infrared light image to the infrared light image intersection extraction section 753.

The infrared light image intersection extraction section 753 extracts an intersection from the blood vessel extraction result supplied from the infrared light image blood vessel extraction section 751, and supplies the intersection extraction result to the intersection alignment processing section 755.

In addition, the initial image blood vessel extraction section 752 supplies the blood vessel extraction result from the initial image to the initial image intersection extraction section 754.

The initial image intersection extraction section 754 extracts an intersection from the blood vessel extraction result supplied from the initial image blood vessel extraction section 752, and supplies the intersection extraction result to the intersection alignment processing section 755.

The intersection alignment processing section 755 aligns the intersections with each other between the infrared light image and the initial image by using the intersection extraction result extracted from each image. In addition, the intersection alignment result is supplied to the blood vessel alignment processing section 756.

The blood vessel alignment processing section 756 sets the intersection alignment result supplied from the intersection alignment processing section 755 to an initial state and performs infrared light image alignment by the use of the blood vessel extraction result. In other words, the blood vessel alignment processing section 756 performs the alignment according to the intersection alignment result in the same manner as in the intersection alignment, and superimposes the respective blood vessel extraction results which are set to an initial state.

In this way, the blood vessel alignment processing section 756 can start alignment from a state of being simply aligned using the intersections, and thereby it is possible to perform alignment more easily at high speed.

In addition, the blood vessel alignment processing section 756 may perform alignment using other pieces of biological information. For example, first, the blood vessel alignment processing section 756 may superimpose the infrared light image on the initial image while performing alignment at a position of the optic nerve head, set the superimposed image as an initial value, and perform alignment using an intersection.

[Configuration of Blood Vessel Alignment Processing Section]

Next, alignment using a position or a shape of the entire blood vessel will be described with reference to FIG. 33.

FIG. 33 is a block diagram illustrating a main configuration example of the blood vessel alignment processing section 756. As illustrated in FIG. 33, the blood vessel alignment processing section 756 includes a superimposition processing component 771, a shift processing component 772, an extension processing component 773, a rotation processing component 774, an enlargement and reduction processing component 775, and a convergence determination component 776.

The superimposition processing component 771 superimposes the blood vessel extraction result (hereinafter, referred to as an infrared light image blood vessel extraction result) by the infrared light image blood vessel extraction section 751 on the blood vessel extraction result (hereinafter, referred to as an initial image blood vessel extraction result) by the initial image blood vessel extraction section 752. In a case of performing alignment using an intersection, the superimposition processing component 771 superimposes the infrared light image blood vessel extraction result on the initial image blood vessel extraction result while performing the same alignment as the intersection alignment by using the intersection alignment result supplied from the intersection alignment processing section 755. The superimposition processing component 771 supplies the superimposition result to the shift processing component 772.

In addition, the blood vessel alignment processing section 756 performs the alignment such that the infrared light image blood vessel extraction result is close to the initial image blood vessel extraction result.

The shift processing component 772 moves (shifts) the entire infrared light image blood vessel extraction result, detects a position where an absolute value difference between the infrared light image blood vessel extraction result and the initial image blood vessel extraction result is the minimum, and supplies the superimposition result to the extension processing component 773 in a state where the absolute value difference is the minimum.

The extension processing component 773 extends (deforms) the infrared light image blood vessel extraction result in any direction, searches for a shape in which an absolute value difference between the infrared light image blood vessel extraction result and the initial image blood vessel extraction result is the minimum, and supplies the superimposition result to the rotation processing component 774 in a state where the absolute value difference is the minimum.

The rotation processing component 774 rotates the infrared light image blood vessel extraction result from side to side, searches for a direction in which an absolute value difference between the infrared light image blood vessel extraction result and the initial image blood vessel extraction result is the minimum, and supplies the superimposition result to the enlargement and reduction processing component 775 in a state where the absolute value difference is the minimum.

The enlargement and reduction processing component 775 enlarges or reduces the infrared light image blood vessel extraction result, searches for a size where an absolute value difference between the infrared light image blood vessel extraction result and the initial image blood vessel extraction result is the minimum, and supplies the superimposition result to the convergence determination component 776 in a state where the absolute value difference is the minimum.

The convergence determination component 776 determines whether or not the alignment converges based on the supplied superimposition results. For example, the convergence determination component 776 compares the alignment result obtained this time with the alignment result obtained the previous time by repeatedly performing the above-described respective processes multiple times, and, if the infrared light image blood vessel extraction result is closer to the initial image blood vessel extraction result than the previous time, it is determined that the alignment does not converge, and, if the infrared light image blood vessel extraction result is not closer to the initial image blood vessel extraction result than the previous time, it is determined that the alignment converges.

If it is determined that the alignment does not converge, the convergence determination component 776 returns the superimposition result to the shift processing component 772 such that alignment is performed again. In addition, if it is determined that the alignment converges, the convergence determination component 776 stores the superimposition result (for example, a superimposition result when an absolute value difference between the infrared light image blood vessel extraction result and the initial image blood vessel extraction result is the minimum) in the alignment information buffer 714 as alignment information.

In addition, the intersection alignment processing section 755 has basically the same configuration as the blood vessel alignment processing section 756, and basically performs the same process except for a difference between the entire blood vessel and an intersection thereof which are biological information used for alignment.

The alignment process is performed on all the infrared light images, and alignment information corresponding to each infrared light image is stored in the alignment information buffer 714. Then, the visible light image alignment processing portion 715 reads the visible light images from the input image buffer 711 one by one, and reads the alignment information of the infrared light image corresponding to the read visible light image from the alignment information buffer 714. In addition, the visible light image alignment processing portion 715 performs alignment by applying the alignment information to the visible light images.

The aligned visible light images are supplied to the super-resolution processing portion 716, and undergo a super-resolution process through superimposition of the images. With reference to all the visible light images, a fundus image which is generated through the repetition of the alignment and the super-resolution process and has a higher resolution and a wider dynamic range is stored in the storage unit 103 or is output from the output unit 104. In addition, here, the high resolution indicates an image from which blurring is removed and which is thus sharp, and, the resolution may not be high in practice.

[Flow of Fundus Image Generation Process]

Next, with reference to a flowchart of FIG. 34, a description will be made of an example of the flow of the fundus image generation process executed by the fundus image processing apparatus 700.

In step S601, the imaging unit 701 performs a plurality of imagings of the examinee's fundus (that is, a subject) using visible light and infrared light together. At this time, the visible light has a low light amount, and the infrared light has a light amount sufficient to perform alignment.

In step S602, the image processing unit 702 stores the captured images obtained through the process in step S601, that is, the visible light images and the infrared light images in the input image buffer 711.

In step S603, the infrared light image alignment processing portion 712 stores an initial infrared light image in the initial image buffer 713 as an initial image.

In step S604, the infrared light image alignment processing portion 712 selects and reads one of unprocessed infrared light images from the input image buffer 711.

In step S605, the infrared light image alignment processing portion 712 performs an alignment process. In addition, the alignment process is basically the same as the biological information alignment process described with reference to the flowcharts of FIGS. 13 and 14. However, there is a difference in that, in the biological information alignment process of FIG. 13, an input image and a previous super-resolution result image are used, whereas, in the alignment process in step S605, an infrared light image and an initial image are used. Therefore, description of the alignment process is repeated and thus will be omitted.

In step S606, the infrared light image alignment processing portion 712 stores the alignment information in the alignment information buffer 714.

In step S607, the infrared light image alignment processing portion 712 determines whether or not all the infrared light images have been processed, and if it is determined that there are unprocessed infrared light images, the process returns to step S604 so as to execute the subsequent processes.

If it is determined that all the infrared light images have been processed in step S607, the process proceeds to step S608.

In step S608, the visible light image alignment processing portion 715 stores an initial visible light image in the super-resolution result image buffer 717 as an initial image.

In step S609, the visible light image alignment processing portion 715 selects and reads one of unprocessed visible light images from the input image buffer 711.

In step S610, the visible light image alignment processing portion 715 reads the alignment information stored in the alignment information buffer 714. In other words, the visible light image alignment processing portion 715 reads the alignment information of the infrared light image corresponding to the visible light image read in step S609.

In step S611, the visible light image alignment processing portion 715 performs alignment on the visible light image by using the alignment information.

In step S612, the super-resolution processing portion 716 performs a super-resolution process. In addition, the super-resolution process is basically the same as the super-resolution process described with reference to the flowchart of FIG. 15. However, there is a difference in that, in the super-resolution process of FIG. 15, an aligned input image and a previous super-resolution result image are superimposed, whereas, in the super-resolution process in step S612, an aligned infrared light image and a previous super-resolution result image are superimposed. Therefore, description of the super-resolution process is repeated and thus will be omitted.

In step S613, the super-resolution processing portion 716 outputs the new super-resolution result image obtained through the super-resolution process to the storage unit 103 or the output unit 104 and stores the super-resolution result image in the super-resolution result image buffer 717.

In step S614, the super-resolution processing portion 716 determines whether or not all the visible light images have been processed, and, if it is determined that there are unprocessed visible light images, the process returns to step S609 so as to execute the subsequent processes.

If it is determined that all the visible light images have been processed in step S614, the fundus image generation process finishes.

As described above, since the visible light image is aligned using the alignment information in the infrared light image, it is possible to obtain a captured image of a subject with higher image quality.

5. Fifth Embodiment

Another Configuration of Fundus Image Processing Apparatus

A description will be made of another configuration example of the fundus image processing apparatus in a case where the visible light image is aligned using the alignment information in the infrared light image.

FIG. 35 is a block diagram illustrating another configuration example of the fundus image processing apparatus. The fundus image processing apparatus 800 illustrated in FIG. 35 generates a fundus image with higher image quality by using biological information included in a visible light image which is aligned using alignment information in an infrared light image for a tone reproduction process or a super-resolution process.

The fundus image processing apparatus 800 has basically the same configuration as the fundus image processing apparatus 700 of FIG. 29 and performs the same process. However, the fundus image processing apparatus 800 includes an image processing unit 802 instead of the image processing unit 702 included in the fundus image processing apparatus 700. Therefore, in the following, only the image processing unit 802 will be described.

The image processing unit 802 has basically the same configuration as the image processing unit 702 and performs the same process. However, the image processing unit 802 includes a noise reduction processing portion 811, a noise reduction result image buffer 812, a tone reproduction processing portion 415, and a super-resolution processing portion 416 instead of the super-resolution processing portion 716 and the super-resolution result image buffer 717 included in the image processing unit 702. Therefore, in the following, only the noise reduction processing portion 811, the noise reduction result image buffer 812, the tone reproduction processing portion 415, and the super-resolution processing portion 416 will be described.

The noise reduction processing portion 811 has basically the same configuration as the noise reduction processing portion 413 of FIG. 16 and performs the same process. However, the noise reduction processing portion 811 enlarges a dynamic range of a fundus image by superimposing a visible light image which is aligned by the visible light image alignment processing portion 715 on a previous superimposition result (that is, noise reduction result) image held in the noise reduction result image buffer 812, thereby reducing noise.

The noise reduction result image buffer 812 has basically the same configuration as the noise reduction result image buffer 414 of FIG. 16 and performs the same process. However, the noise reduction result image buffer 812 stores the noise reduction result image generated by the noise reduction processing portion 811, and appropriately supplies the noise reduction result image to the noise reduction processing portion 811 as necessary. In addition, the noise reduction result image buffer 812 stores an aligned visible light image which is first supplied from the visible light image alignment processing portion 715 via the noise reduction processing portion 811 as an initial image.

The tone reproduction processing portion 415 and the super-resolution processing portion 416 basically respectively have the same configuration as the tone reproduction processing portion 415 and the super-resolution processing portion 416 of FIG. 16 and perform the same process. Therefore, description thereof is repeated and thus will be omitted.

[Flow of Fundus Image Generation Process]

Next, with reference to a flowchart of FIG. 36, a description will be made of an example of the flow of the fundus image generation process executed by the fundus image processing apparatus 800.

The respective processes in steps S641 to S651 are the same as the respective processes in steps S601 to S611 of FIG. 34, and description thereof is repeated and thus will be omitted.

The respective processes in steps S652 to S656 are basically the same as the processes in steps S406 to S410 of FIG. 22. However, in step S652, the noise reduction processing portion 811 superimposes the visible light images aligned through the process in step S651, thereby reducing noise.

In step S653, the noise reduction processing portion 811 determines whether or not all the visible light images have been processed. If it is determined that there are unprocessed visible light images, the noise reduction processing portion 811 makes process proceed to step S654.

In step S654, the noise reduction result image buffer 812 stores the noise reduction process result image obtained through the process in step S652, that is, the superimposed visible light image. When the visible light image is stored, the noise reduction result image buffer 812 returns the process to step S649 and repeatedly performs the subsequent processes.

If the processes in steps S649 to S654 are repeatedly performed, and it is determined that all the visible light images have been processed in step S653, the noise reduction processing portion 811 makes the process proceed to step S655.

In step S655, the tone reproduction processing portion 415 performs the tone reproduction process on a single generated visible light image. In addition, details of the tone reproduction process are basically the same as those with reference to the flowcharts of FIGS. 23 and 24, and description thereof will be omitted.

In step S656, the super-resolution processing portion 416 performs a super-resolution process on the visible light image having undergone the tone reproduction process. In addition, details of the super-resolution process are basically the same as those with reference to the flowchart of FIG. 25, and description thereof will be omitted.

Thereby, the fundus image with a high resolution is obtained, and the fundus image generation process finishes.

As described above, since the visible light image is aligned using alignment information in the infrared light image, it is possible to obtain a captured image of a subject with higher image quality.

[Application to Fundus Image Processing Apparatuses with Other Configurations]

Meanwhile, the techniques of the fourth and fifth embodiments where a captured image of a subject with higher image quality is obtained using both the visible light image and the infrared light image obtained by the imaging unit may be applied to each of the fundus image processing apparatuses 100, 200 and 400 according to the above-described first to third embodiments.

The respective configurations of the fundus image processing apparatuses 100, 200 and 400 to which the techniques of the fourth and fifth embodiments are applied basically have the same configurations as the respective configurations illustrated in FIGS. 1, 3 and 16. However, the respective fundus image processing apparatuses 100, 200 and 400 to which the techniques of the fourth and fifth embodiments are applied use both images, the visible light image and the infrared light image, and thus processes different from the processes in the first to third embodiments are performed. Therefore, hereinafter, a description will be made of processes in a case where the techniques of the fourth and fifth embodiments are applied in order of the fundus image processing apparatuses 100, 200 and 400.

First, a description will be made of the fundus image processing apparatus 100 of FIG. 1 in a case of using both the visible light image and the infrared light image.

The imaging unit 101 of the fundus image processing apparatus 100 of FIG. 1 performs a plurality of imagings of the fundus using visible light and infrared light together. In other words, the imaging unit 101 has the same configuration as the imaging unit 701 of FIG. 29 and performs the same process.

In the image processing unit 102, only the infrared light image is used for a process by the motion vector detection section 121, and both the visible light image and the infrared light image are used for processes by the other constituent elements of the image processing unit 102.

That is to say, the input image buffer 111 stores the visible light image and the infrared light image supplied from the imaging unit 101 as input images.

The SR image buffer 113 holds SR images of the generated visible light image and the infrared light image, and supplies the SR images of the generated visible light image and the infrared light image to the super-resolution processing portion 112 or the calculation portion 114 at a predetermined timing.

The SR image of the infrared light image held in the SR image buffer 113 is supplied to the motion vector detection section 121 and the motion compensation section 122, and the LR image of the infrared light image held in the input image buffer 111 is supplied to the motion vector detection section 121 and the calculation section 124. On the other hand, the SR image of the visible light image held in the SR image buffer 113 is supplied only to the motion compensation section 122, and the LR image of the visible light image held in the input image buffer 111 is supplied only to the calculation section 12.

The motion vector detection section 121 detects a motion vector using the SR image of the infrared light image as a reference on the basis of the SR image and the LR image of the infrared light image which are input thereto, and supplies the detected motion vector of the infrared light image to the motion compensation section 122 and the backward motion compensation section 126.

The motion compensation section 122 performs motion compensation on the SR images of the visible light image and the infrared light image on the basis of the motion vector of the infrared light image supplied from the motion vector detection section 121, and supplies a visible light image and an infrared light image obtained through the motion compensation to the down-sampling filter 123.

The down-sampling filter 123 generates a visible light image and an infrared light image with the same resolution as that of the LR image by down-sampling the visible light image and the infrared light image supplied from the motion compensation section 122, and supplies the generated visible light image and infrared light image to the calculation section 124.

The calculation section 124 generates difference images respectively indicating differences between the LR images of the visible light image and the infrared light image, and the down-sampled visible light image and infrared light image, and supplies the respectively generated difference images of the visible light image and the infrared light image to the up-sampling filter 125.

The up-sampling filter 125 generates images with the same resolution as that of the SR images by up-sampling the respective difference images of the visible light image and the infrared light image supplied from the calculation section 124, and outputs the generated visible light image and infrared light image to the backward motion compensation section 126.

The backward motion compensation section 126 performs backward motion compensation on the visible light image and the infrared light image supplied from the up-sampling filter 125 on the basis of the motion vector of the infrared light image supplied from the motion vector detection section 121, and supplies a feedback value indicating the visible light image and the infrared light image obtained through the backward motion compensation to the calculation portion 114.

The calculation portion 114 adds the feedback value supplied from the backward motion compensation section 126 to the SR images of the visible light image and the infrared light image, generated in the past, supplied from the SR image buffer 113, thereby generating new SR images of the visible light image and the infrared light image. The calculation portion 114 supplies the generated new SR images of the visible light image and the infrared light image to the SR image buffer 113 so as to be stored, and thereby the SR images are used for a subsequent super-resolution process (that is, generation of new SR images). In addition, the calculation portion 114 supplies the generated SR image of the visible light image to the storage unit 103 so as to be stored, supplies the SR image to the output unit 104 so as to be displayed, or outputs the SR image to an external device.

The image processing unit 102 performs the super-resolution process on each of a plurality of fundus images (LR images) of the visible light image and the infrared light image held in the input image buffer 111 by using the super-resolution processing portion 112, and finally generates a single SR image with higher image quality.

[Flow of Fundus Image Generation Process]

With reference to a flowchart of FIG. 37, a description will be made of an example of the fundus image generation process using both the visible light image and the infrared light image, performed by the fundus image processing apparatus 100.

The imaging unit 101 performs a plurality of imagings of the examinee's fundus (that is, a subject) using visible light and infrared light together in step S681.

In step S682, the image processing unit 102 stores the visible light image and the infrared light image obtained through the process in step S101 in the input image buffer 111.

In step S683, the image processing unit 102 generates initial images which are initial SR images of the visible light image and the infrared light image using any method so as to be stored in the SR image buffer 113.

In step S684, the input image buffer 111 selects one of visible light images and one of infrared light images (that is, LR images) which are unprocessed and are held therein, so as to be supplied to the super-resolution processing portion 112.

In step S685, the motion vector detection section 121 detects a motion vector from the SR image and the LR image of the infrared light image.

In step S686, the motion compensation section 122 performs motion compensation on the SR images of the visible light image and the infrared light image by using the motion vector of the infrared light image.

In step S687, the down-sampling filter 123 down-samples the SR images of the visible light image and the infrared light image having undergone the motion compensation to the same resolution as that of the LR image.

In step S688, the calculation section 124 obtains difference images between the down-sampling results of the SR images of the visible light image and the infrared light image, and the input LR images of the visible light image and the infrared light image.

In step S689, the up-sampling filter 125 up-samples the respective difference images of the visible light image and the infrared light image.

In step S690, the backward motion compensation section 126 performs backward motion compensation on the up-sampling results of the respective difference images of the visible light image and the infrared light image by using the motion vector of the infrared light image detected through the process in step S685.

In step S691, the calculation portion 114 adds feedback values which are results of the up-sampling of the respective difference images of the visible light image and the infrared light image calculated through the process in step S690 to the SR images of the visible light image and the infrared light image, generated in the past, held in the SR image buffer 113, respectively.

In step S692, the image processing unit 102 stores or outputs the generated new SR image of the visible light image in the storage unit 103 or from the output unit 104, and stores the visible light image and the infrared light image in the SR image buffer 113.

In step S693, the input image buffer 111 determines whether or not all the visible light images and the infrared light images (LR images) have been processed, and, if it is determined that there are unprocessed visible light images and infrared light images (LR images), the input image buffer returns the process to step S684, selects new visible light image and infrared light image as process targets, and repeatedly performs the subsequent processes on the visible light image and the infrared light image.

In step S693, if it is determined that all of a plurality of visible light images and infrared light images obtained through a plurality of imagings by the imaging unit 101 have been processed, and thus a single fundus image of the visible light image with higher image quality has been obtained, the fundus image generation process finishes.

In this way, the fundus image processing apparatus 100 can obtain a fundus image with higher image quality without increasing a light amount of irradiation light of visible light applied to the fundus. That is to say, the fundus image processing apparatus 100 can suppress an increase in load on a subject and obtain a captured image of the subject with higher image quality.

Next, a description will be made of the fundus image processing apparatus 200 of FIG. 3 in a case of using both the visible light image and the infrared light image.

The imaging unit 101 of the fundus image processing apparatus 200 of FIG. 3 repeatedly performs a plurality of imagings of the fundus using visible light and infrared light together. In other words, the imaging unit 101 has the same configuration as the imaging unit 701 of FIG. 29 and performs the same process.

In the image processing unit 202, only the infrared light image is used for a process by the biological information alignment processing portion 212, and both the visible light image and the infrared light image are used for processes by the other constituent elements of the image processing unit 202.

That is to say, the input image buffer 111 stores the visible light image and the infrared light image supplied from the imaging unit 101 as input images.

The biological information alignment processing portion 212 performs image alignment on an infrared light image (that is, an input image) supplied from the input image buffer 111 and an infrared light image (that is, an image superimposed by the super-resolution processing portion 213) supplied from the super-resolution result image buffer 214 by using biological information of a subject. In addition, the biological information alignment processing portion 212 reflects the alignment result of the infrared light images on a visible light image supplied from the input image buffer 111.

The super-resolution processing portion 213 acquires a super-resolution process result image of the visible light image and the infrared light image (that is, an image obtained as a result of the super-resolution process) generated in the past from the super-resolution result image buffer 214, and superimposes the super-resolution result image on input images of the visible light image and the infrared light image aligned by the biological information alignment processing portion 212, thereby generating new super-resolution result images of the visible light image and the infrared light image. The super-resolution processing portion 213 stores or outputs the super-resolution result images of the visible light image in the storage unit 103 or from the output unit 104, and supplies the visible light image and the infrared light image to the super-resolution result image buffer 214 so as to be stored.

The super-resolution result image buffer 214 holds the super-resolution result images of the visible light image and the infrared light image generated by the super-resolution processing portion 213 and supplies the super-resolution result images to the biological information alignment processing portion 212 or the super-resolution processing portion 213 at a predetermined timing.

[Flow of Fundus Image Generation Process]

With reference to a flowchart of FIG. 38, a description will be made of an example of the flow of the fundus image generation process using both the visible light image and the infrared light image, performed by the fundus image processing apparatus 200.

The respective processes in steps S721 to S724 are performed in the same manner as the respective processes in steps S681 to S684 of FIG. 37. However, in step S723, initial images of the visible light image and the infrared light image are stored in the super-resolution result image buffer 214. In addition, in step S724, unprocessed visible light image and infrared light image are respectively selected singly as input images.

When process targets are set, the biological information alignment processing portion 212 performs a biological information alignment process on the infrared light image in step S725. In addition, details of the biological information alignment process are basically the same as those described with reference to the flowchart of FIG. 13, and description thereof will be omitted. However, in the flowchart of FIG. 13, only details of the blood vessel alignment process in step S227 will be described later with reference to FIG. 39.

In step S726, the super-resolution processing portion 213 performs a super-resolution process by using the alignment results of the visible light image and the infrared light image. In addition, details of the super-resolution process are basically the same as those described with reference to the flowchart of FIG. 15, and description thereof will be omitted.

In step S727, the super-resolution processing portion 213 outputs a new super-resolution result image of the visible light image obtained through the super-resolution process to the storage unit 103 or the output unit 104, and stores the visible light image and the infrared light image in the super-resolution result image buffer 214.

In step S728, the input image buffer 111 determines whether or not all the visible light images and the infrared light images have been processed, and, if there are unprocessed visible light images and infrared light images, the input image buffer returns the process to step S724 so as to execute the subsequent processes.

If it is determined that all the visible light images and the infrared light images have been processed in step S728, the fundus image generation process finishes.

[Flow of Blood Vessel Alignment Process]

Next, with reference to a flowchart of FIG. 39, a description will be made of an example of the flow of the blood vessel alignment process executed in step S227 in the biological information alignment process in step S725 of FIG. 38 (that is, the biological information alignment process of FIG. 13).

The respective processes in steps S741 to S748 are performed in the same manner as the respective processes in steps S241 to S248 of FIG. 14. However, the respective processes in steps S741 to S748 are performed on an infrared light image which is a process target.

If it is determined that the alignment converges in step S748, the biological information alignment processing portion 212 reads a visible light image corresponding to the infrared light image which is a process target from the input image buffer 111 in step S749.

In step S750, the biological information alignment processing portion 212 reflects the alignment result of the infrared light image which is a process target on the visible light image read in step S749. In other words, the visible light image is aligned.

In step S751, the biological information alignment processing portion 212 aligns the infrared light image on the basis of the alignment result of the infrared light image, and outputs the aligned visible light image and infrared light image and the blood vessel extraction result to the super-resolution processing portion 213.

Thereby, the blood vessel alignment process finishes.

In this way, the fundus image processing apparatus 200 can obtain a fundus image with higher image quality without increasing a light amount of irradiation light of visible light applied to the fundus. That is to say, the fundus image processing apparatus 200 can suppress an increase in load on a subject and obtain a captured image of the subject with higher image quality.

Next, a description will be made of the fundus image processing apparatus 400 of FIG. 16 in a case of using both the visible light image and the infrared light image.

The imaging unit 101 of the fundus image processing apparatus 400 of FIG. 16 repeatedly performs a plurality of imagings of the fundus using visible light and infrared light together. In other words, the imaging unit 101 has the same configuration as the imaging unit 701 of FIG. 29 and performs the same process.

In the image processing unit 402, only the infrared light image is used for a process by the biological information alignment processing portion 212, and both the visible light image and the infrared light image are used for processes by the other constituent elements of the image processing unit 402.

That is to say, the input image buffer 111 stores the visible light image and the infrared light image supplied from the imaging unit 101 as input images.

The biological information alignment processing portion 212 performs image alignment on an infrared light image (that is, an input image) supplied from the input image buffer 111 and an infrared light image (that is, an image superimposed by the noise reduction processing portion 413) supplied from the noise reduction result image buffer 414 by using biological information of a subject. In addition, the biological information alignment processing portion 212 reflects the alignment result of the infrared light images on a visible light image supplied from the input image buffer 111.

The noise reduction processing portion 413 enlarges a dynamic range of the visible light image and the infrared light image by respectively superimposing the visible light image and the infrared light image which are aligned by the biological information alignment processing portion 212 on the visible light image and the infrared light image of previous superimposition results (that is, noise reduction results) held in the noise reduction result image buffer 414, thereby reducing noise.

The noise reduction result image buffer 414 stores the noise reduction result images (that is, superimposition result images) of the visible light image and the infrared light image generated by the noise reduction processing portion 413, and supplies the noise reduction result images of the visible light image and the infrared light image to the biological information alignment processing portion 212 or the noise reduction processing portion 413 on the basis of a request of the biological information alignment processing portion 212 or the noise reduction processing portion 413, or at a predetermined timing.

In other words, the alignment of the infrared light image by the biological information alignment processing portion 212 or the superimposition by the noise reduction processing portion 413 is repeatedly performed. In this way, a plurality of visible light images and infrared light images obtained through imaging by the imaging unit 101 are all processed, and thereby a single visible light image is generated.

The tone reproduction processing portion 415 and the super-resolution processing portion 416 respectively have the same configuration as those of FIG. 16 and perform the same processes. In other words, a single generated visible light image of the tone reproduction processing portion 415 and the super-resolution processing portion 416 undergoes a tone reproduction process in the tone reproduction processing portion 415 and then undergoes a super-resolution process in the super-resolution processing portion 416.

[Flow of Fundus Image Generation Process]

With reference to a flowchart of FIG. 40, a description will be made of an example of the flow of the fundus image generation process using both the visible light image and the infrared light image, performed by the fundus image processing apparatus 400.

The respective processes in steps S771 to S774 are performed in the same manner as the respective processes in steps S721 to S724 of FIG. 38. However, in step S773, initial images of the visible light image and the infrared light image are stored in the noise reduction result image buffer 414.

When process targets are set, the biological information alignment processing portion 212 performs a biological information alignment process on the infrared light image in step S775. In addition, details of the biological information alignment process are basically the same as those described with reference to the flowchart of FIG. 13, and description thereof will be omitted. Further, details of the blood vessel alignment process in step S227 in the flowchart of FIG. 13 are basically the same as those described with reference to the flowchart of FIG. 39, and description thereof will be omitted.

In step S776, the noise reduction processing portion 413 superimposes the respective images of the visible light image and the infrared light image aligned through the process in step S775, thereby reducing noise.

In step S777, the noise reduction processing portion 413 determines whether or not all the visible light images and the infrared light images have been processed. If it is determined that there are unprocessed visible light images and infrared light images in the input image buffer 111, the noise reduction processing portion 413 makes the process proceed to step S778.

In step S778, the noise reduction result image buffer 414 stores the noise reduction process result images of the visible light image and the infrared light image obtained through the process in step S776, that is, the superimposed visible light image and infrared light image. When the visible light image and infrared light image are stored, the noise reduction result image buffer 414 returns the process to step S774 and repeatedly performs the subsequent processes.

If the processes in steps S774 to S778 are repeatedly performed, and it is determined that all the visible light images and the infrared light images have been processed in step S777, the noise reduction processing portion 413 makes the process proceed to step S779.

In step S779, the tone reproduction processing portion 415 performs the tone reproduction process on a generated single visible light image. In addition, details of the tone reproduction process are basically the same as those with reference to the flowchart of FIG. 23, and description thereof will be omitted.

In step S780, the super-resolution processing portion 416 performs a super-resolution process on the image having undergone the tone reproduction process. In addition, details of the super-resolution process are basically the same as those with reference to the flowchart of FIG. 25, and description thereof will be omitted.

When the process in step S780 is completed, the fundus image generation process finishes.

In this way, the fundus image processing apparatus 400 can obtain a fundus image with higher image quality without increasing a light amount of irradiation light of visible light applied to the fundus. That is to say, the fundus image processing apparatus 400 can suppress an increase in load on a subject and obtain a captured image of the subject with higher image quality.

6. Sixth Embodiment

The above-described fundus image processing apparatus is made to be small so as to be carried by an observer, and thereby, for example, a remote medical examination of an examinee's fundus by a doctor is possible. In this case, some processes of the processes by the fundus image processing apparatus are performed on a network, and thereby the fundus image processing apparatus can be made to be small.

FIG. 41 is a diagram illustrating a configuration example of the remote medical examination system. As illustrated in FIG. 41, the remote medical examination system 900 includes a small fundus camera 911, a doctor terminal device 912, a nurse terminal device 913, a patient terminal device 914, a network 915, an image processing device 916, and a database 917.

The small fundus camera 911 performs a plurality of imagings of the fundus of an examinee (that is, a patient), as a subject and transmits data of a plurality of fundus images obtained as a result thereof to the network 915. The small fundus camera 911 includes a CCD imaging device or a CMOS imaging device, a transmission unit which transmits captured fundus images to the network, and the like in the present embodiment. However, it is not necessary for the small fundus camera 911 to particularly have the configuration according to the present embodiment, and any configuration may be used as long as data of a plurality of captured fundus images can be transmitted to the network 915.

In addition, the small fundus camera 911 has a function of applying light to a subject during imaging in order to output a fundus image with higher image quality. In other words, the small fundus camera 911 may have the same configuration as the above-described imaging unit 101 or imaging unit 701, and perform the same process. The small fundus camera 911 has a size which can be carried by an observer, and is operated by a nurse or a patient himself/herself.

The doctor terminal device 912 acquires data of a fundus image and data of additional information as medical examination data from the database 917 via the network 915. From the database 917, data of a fundus image with high image quality generated by the image processing device 916 described later is acquired. In addition, the additional information acquired from the database 917 includes information assisting the medical examination by the doctor, for example, information indicating a target part in a fundus image, and information of similar cases. In addition, the additional information may include, for example, other pieces of information regarding a patient, that is, information such as the patient's physical constitution or clinical history, or may include any information.

The doctor terminal device 912 transmits an indication of an imaging portion, a medical examination result, an instruction for reimaging, and the like by the doctor to the nurse terminal device 913 or the patient terminal device 914 via the network 915 as necessary.

The nurse terminal device 913 receives an indication of an imaging portion, a medical examination result, an instruction for reimaging, or the like from the doctor terminal device 912 via the network 915. In addition, the nurse terminal device 913 acquires data of a fundus image, and data of addition information as necessary, from the database 917 via the network 915.

The patient terminal device 914 receives an indication of an imaging portion, a medical examination result, an instruction for reimaging, or the like from the doctor terminal device 912 via the network 915 as necessary. In addition, the patient terminal device 914 acquires data of a fundus image from the database 917 via the network 915. Further, the patient terminal device 914 may acquire health information or the like from the database 917 via the network 915.

The network 915 is a cloud network, and is, for example, the Internet in the present embodiment.

The image processing device 916 may have the same configuration as any one of the image processing units 102, 202, 402, 702 and 802 respectively included in the above-described fundus image processing apparatuses 100, 200, 400, 700 and 800, and perform the same process. In other words, the image processing device 916 generates a fundus image with higher image quality from a plurality of captured images acquired from the small fundus camera 911 via the network 915. The data of the generated fundus image is stored in the database 917, or is supplied to the doctor terminal device 912, the nurse terminal device 913, or the patient terminal device, via the network 915.

The database 917 stores the data of the fundus image generated by the image processing device 916. In addition, the database 917 stores additional information or other pieces of information. The content of other pieces of information is not particularly limited, and may include, for example, health information or the like. In addition, the number of devices connected via the network 915 is not limited to the example illustrated in FIG. 41.

[Remote Medical Examination Process]

Next, with reference to a flowchart of FIG. 42, a description will be made of an example of the flow of the remote medical examination process executed by the remote medical examination system 900.

In step S881, the small fundus camera 911 performs a plurality of imagings of the fundus in response to an operation of the nurse or the patient. In other words, the small fundus camera 911 performs a plurality of imagings of the fundus using irradiation light of visible light with a low light amount, or irradiation light including visible light at a low light amount and infrared light with a light amount sufficient to perform alignment.

In step S882, the small fundus camera 911 transmits data of the captured images of the fundus obtained in step S881 to the network 915.

In step S883, the image processing device 916 performs a fundus image generation process of generating a fundus image with higher image quality from the captured images of the fundus acquired via the network 915. In addition, the fundus image generation process in step S883 is basically the same as the fundus image generation process described with reference to the flowchart of FIG. 2, 12, 22, 34 or 36. However, the imaging process of the fundus which is first performed in the fundus image generation process of FIG. 2, 12, 22, 34 or 36 is performed by the small fundus camera 911 in step S881, and thus the subsequent processes from the second process in each fundus image generation process are performed.

In step S884, the image processing device 916 stores data of the generated fundus image in the database 917 via the network 915.

In step S885, the doctor terminal device 912 acquires the data of the fundus image and data of additional information as data for medical examination from the database 917 via the network 915. Thereafter, the doctor terminal device 912 transmits a medical examination result to the nurse terminal device 913 or the patient terminal device 914 via the network 915 as necessary.

In step S886, the doctor terminal device 912 determines whether or not reimaging is instructed. In a case where reimaging is instructed, the process returns to step S881 and the subsequent processes are repeatedly performed.

In a case where reimaging is not instructed in step S886, the remote medical examination process finishes.

According to the remote medical examination system 900, a doctor in a remote location can perform medical examination by using captured images of the fundus which is obtained by a nurse or a patient imaging the fundus with the small fundus camera 911. In this case, since a captured image of a subject with high image quality can be generated by the image processing device 916 on the network 915 from the captured images obtained by the small fundus camera 911, the doctor can perform remote medical examination while viewing the captured image of a subject with high image quality.

7. Seventh Embodiment

Personal Computer

The above-described series of processes may be performed by hardware or software. In this case, for example, a personal computer as illustrated in FIG. 43 may be configured.

In FIG. 43, a CPU (Central Processing Unit) 1001 of the personal computer 1000 performs various processes according to a program stored in a ROM 1002 or a program loaded to a RAM 1003 from a storage unit 1013. The RAM 1003 appropriately stores data or the like which is necessary for the CPU 1001 to execute various processes.

The CPU 1001, the ROM 1002, and the RAM 1003 are connected to each other via a bus 1004. The bus 1004 is also connected to an input and output interface 1010.

The input and output interface 1010 is connected to an input unit 1011 including a keyboard, a mouse, and the like, an output unit 1012 including a display such as a CRT (Cathode Ray Tube) display or an LCD (Liquid Crystal Display), a speaker, and the like, the storage unit 1013 including a hard disk or the like, and a communication unit 1014 including a modem or the like. The communication unit 1014 performs a communication process via a network including the Internet.

The input and output interface 1010 is connected to a drive 1015 as necessary, a removable medium 1021 such as a magnetic disk, an optical disc, a magneto-optical disc, or a semiconductor memory is appropriately installed therein, and a computer program read therefrom is installed in the storage unit 1013 as necessary.

In a case where the above-described series of processes is executed using software, a program constituting the software is installed from a network or a recording medium.

The recording medium includes, for example, as illustrated in FIG. 43, not only the removable medium 1021 on which a program is recorded, such as a magnetic disk (including a flexible disc), an optical disc (including a CD-ROM (Compact Disc-Read Only Memory) and a DVD (Digital Versatile Disc)), a magneto-optical disc (including an MD (Mini Disc)), or a semiconductor memory, which is distributed so as to deliver a program to a user separately from a device body, but also the ROM 1002 which is sent to a user in a state of being incorporated in a device body in advance and records a program therein, or a hard disk included in the storage unit 1013.

The program executed by the computer may be a program where processes are performed in a time series according to the order described in the present specification, or may be a program executed in parallel or a program where processes are performed at a necessary timing such as when accessed.

Further, in the present specification, the steps for describing programs recorded on a recording medium include not only processes performed in a time series according to the described order, but also processes performed in parallel or separately even if not necessarily performed in the time series. Each step may be processed by different devices. In addition, a single step may be distributed over different processes.

In addition, in the present specification, the system refers to the entire apparatus including a plurality of devices.

Further, in the above description, a configuration described as a single device (or a processing unit) may be divided into and formed by a plurality of devices (or processing units). Conversely, in the above description, configurations described as a plurality of devices (or processing units) may be integrally formed by a single device (or a processing unit). In addition, configurations other than those described above may be added to the configuration of each device (or each processing unit). Further, a part of the configuration of one device (or a processing unit) may be included in the configuration of another device (or another processing unit) as long as the configuration and operation of the overall system are substantially the same. In addition, embodiments of the present technology are not limited to the above-described embodiments but may have various modifications without departing from the scope of the present technology.

In addition, the present technology may have the following configurations.

(1)

An image processing apparatus including an alignment unit that performs alignment so as to adjust positions of a subject in a plurality of captured images obtained by an imaging unit which images the subject, by using biological information of the subject; and a superimposition unit that superimposes the captured images aligned by the alignment unit so as to generate an image of the subject having a dynamic range wider than that of the captured image.

(2)

The image processing apparatus set forth in (1), wherein the superimposition unit includes a detection portion that detects a motion vector between the captured image and the image of the subject generated through the superimposition; a motion compensation portion that performs motion compensation on the image of the subject by using the motion vector detected by the detection portion; a subtraction portion that subtracts the captured image from the image of the subject having undergone the motion compensation by the motion compensation portion; a backward motion compensation portion that performs motion compensation on a difference value between the image of the subject by the subtraction portion and the captured image in a reverse direction to the motion compensation by the motion compensation portion, by using the motion vector detected by the detection portion; and an adding portion that adds the difference value having undergone the motion compensation by the backward motion compensation portion to the image of the subject.

(3)

The image processing apparatus set forth in (1) or (2), wherein the superimposition unit further includes a down-sampling portion that down-samples the image of the subject having undergone the motion compensation by the motion compensation portion so as to reduce a resolution of the subject to the resolution of the captured image; and an up-sampling portion that up-samples the difference value between the image of the subject by the subtraction portion and the captured image so as to increase the resolution of the difference value to the resolution of the image of the subject, wherein the subtraction portion subtracts the captured image from the image of the subject down-sampled by the down-sampling portion, and wherein the backward motion compensation portion performs motion compensation on the difference value up-sampled by the up-sampling portion in a reverse direction to the motion compensation by the motion compensation portion, by using the motion vector detected by the detection portion.

(4)

The image processing apparatus set forth in (1), (2) or (3), wherein the alignment unit performs alignment so as to adjust positions of the subject in the captured images obtained by the imaging unit to a position of the subject in the image of the subject generated the previous time, and wherein the superimposition unit superimposes the captured images aligned by the alignment unit on the image of the subject generated the previous time one by one so as to generate the image of the subject which is obtained by superimposing the plurality of captured images on each other and has a dynamic range wider than that of the captured image.

(5)

The image processing apparatus set forth in any one of (1) to (4), wherein the subject is a fundus, and wherein the alignment unit uses a blood vessel as the biological information.

(6)

The image processing apparatus set forth in any one of (1) to (5), wherein the alignment unit further uses an intersection of the blood vessel as the biological information.

(7)

The image processing apparatus set forth in any one of (1) to (6), further including an estimation unit that estimates a point spread function of the captured images aligned by the alignment unit; and a removal unit that removes blurring from the captured images by using the point spread function estimated by the estimation unit, wherein the superimposition unit superimposes the captured images which have been aligned by the alignment unit and from which the blurring has been removed by the removal unit on the image of the subject generated the previous time one by one so as to generate the image of the subject which is obtained by superimposing the plurality of captured images on each other and has a dynamic range wider than that of the captured image.

(8)

The image processing apparatus set forth in any one of (1) to (7), wherein the imaging unit performs a plurality of imagings of the subject while irradiating the subject with irradiation light which is relatively dark.

(9)

An image processing method of an image processing apparatus, including causing an alignment unit to perform alignment so as to adjust positions of a subject in a plurality of captured images obtained by an imaging unit which images the subject, by using biological information of the subject; and causing a superimposition unit to superimpose the captured images aligned so as to generate an image of the subject having a dynamic range wider than that of the captured image.

(10)

An image processing apparatus including a superimposition unit that superimposes a plurality of captured images on each other obtained by an imaging unit which images a subject; and a grayscale correction unit that performs grayscale correction on a captured image which is generated by the superimposition unit superimposing the plurality of captured images according to biological information of the subject.

(11)

The image processing apparatus set forth in any one (10), wherein the grayscale correction unit includes a parameter setting portion that sets a value of a parameter for calculating a tone curve used for the grayscale correction of the captured image, according to the biological information of the subject.

(12)

The image processing apparatus set forth in any one of (10) or (11), wherein the parameter setting portion includes an adjustment section that adjusts a value of a parameter for calculating the tone curve used for the grayscale correction of the captured image in a predetermined method; a correction section that corrects the captured image by using the parameter where the value has been adjusted by the adjustment section; a part checking section that checks a corrected captured image which is the captured image corrected by the correction section, for each part as a living body included in the captured image, in a method according to a feature of an image of each part; a comparison section that compares brightness of an uncorrected captured image which is the captured image before being corrected by the correction section with brightness of the corrected captured image when the corrected captured image passes checking performed by the part checking section; and an output section that outputs the value of the parameter as a set value when the adjustment by the adjustment section, the correction by the correction section, the checking by the part checking section, and the comparison by the comparison section are repeatedly performed, and it is determined by the comparison section that the corrected captured image is not brighter than the uncorrected captured image.

(13)

The image processing apparatus set forth in (10), (11) or (12), wherein the parameter setting portion further includes a part recognition section that analyzes the captured image and recognizes a part as a living body included in the captured image, and wherein the part checking section checks each part recognized by the part recognition section.

(14)

The image processing apparatus set forth in any one of (10) to (13), wherein the parameter setting portion further includes a brightness value calculation section that calculates a brightness value indicating brightness of the captured image, and wherein the comparison section compares a brightness value of the uncorrected captured image with a brightness value of the corrected captured image, calculated by the brightness value calculation section.

(15)

The image processing apparatus set forth in any one of (10) to (14), wherein the parameter setting portion further includes a parameter selection section that selects an adjustment target parameter to be adjusted by the adjustment section from a plurality of parameters.

(16)

The image processing apparatus set forth in any one of (10) to (15), wherein the parameter setting portion further includes a part recognition section that analyzes the captured image and recognizes a part as a living body included in the captured image, wherein the correction section corrects an image of each part recognized by the part recognition section, wherein the part checking section checks the image of each part corrected by the correction section, and wherein the comparison section compares brightness of the image of each part before and after corrected by the correction section.

(17)

The image processing apparatus set forth in any one of (10) to (16), further including a high resolution unit that increases the resolution of the captured image having undergone the grayscale correction by the grayscale correction unit.

(18)

The image processing apparatus set forth in any one of (10) to (17), wherein the high resolution unit increases the resolution of the captured image having undergone the grayscale correction by the grayscale correction unit, according to the biological information of the subject.

(19)
An image processing method of an image processing apparatus, including causing a superimposition unit to superimpose a plurality of captured images on each other obtained by an imaging unit which images a subject; and causing a grayscale correction unit to perform grayscale correction on a captured image which is generated by superimposing the plurality of captured images, according to biological information of the subject.

(20)
An image processing apparatus including a superimposition unit that superimposes a plurality of captured images on each other obtained by an imaging unit which images a subject; and a high resolution unit that increases the resolution of a captured image which is generated by the superimposition unit superimposing the plurality of captured images, according to biological information of the subject.

(21)
The image processing apparatus set forth in (20), wherein the high resolution unit includes a super-resolution processing portion that performs a super-resolution process of improving the resolution of the captured image through learning on the captured image according to each of a plurality of kinds of learning dictionaries, so as to generate a plurality of super-resolution result images which are captured images with a high resolution; a part image evaluation portion that evaluates each super-resolution result image which is generated through the super-resolution process by the super-resolution processing portion by using each learning dictionary, for each part as a living body included in the super-resolution result image, in a method according to a feature of an image of each part; and an image selection portion that selects the optimal super-resolution result image from the plurality of super-resolution result images on the basis of the evaluation by the part image evaluation portion.

(22)
The image processing apparatus set forth in (20) or (21), wherein the high resolution unit further includes a part recognition portion that analyzes the super-resolution result image and recognizes a part as a living body included in the super-resolution result image, and wherein the part image evaluation portion evaluates each super-resolution result image for each part recognized by the part recognition portion, in a method according to a feature of an image of each part.

(23)
The image processing apparatus set forth in (20), (21) or (22), further comprising a grayscale correction unit that performs grayscale correction on a captured image which is generated by the superimposition unit superimposing the plurality of captured images,
wherein the high resolution unit increases the resolution of the captured image having undergone the grayscale correction by the grayscale correction unit, according to the biological information of the subject.

(24)
The image processing apparatus set forth in any one of (20) to (24), wherein the grayscale correction unit performs grayscale correction on a captured image which is generated by the superimposition unit superimposing the plurality of captured images, according to the biological information of the subject.

(25)
An image processing method of an image processing apparatus, including causing a superimposition unit to superimpose a plurality of captured images on each other obtained by an imaging unit which images a subject; and causing a high resolution unit to increase the resolution of a captured image which is generated by superimposing the plurality of captured images, according to biological information of the subject.

(26)
An image processing apparatus including an infrared light image alignment unit that performs alignment so as to adjust positions of a subject in a plurality of infrared light images obtained by an imaging unit which images the subject, by using biological information of the subject; an alignment information storage unit that stores alignment information which is a result of the alignment by the infrared light image alignment unit; a visible light image alignment unit that performs alignment so as to adjust positions of the subject in a plurality of visible light images obtained by the imaging unit, by using the alignment information stored in the alignment information storage unit; and a superimposition unit that superimposes the visible light images aligned by the visible light alignment unit so as to generate an image of the subject having a dynamic range wider than that of the visible light image.

(27)
The image processing apparatus set forth in (26), wherein the imaging unit performs a plurality of imagings of the subject while irradiating the subject with irradiation light including visible light with a predetermined light amount and infrared light with a light amount larger than the predetermined light amount.

(28)
The image processing apparatus set forth (26) or (27), wherein the infrared light image alignment unit performs the alignment such that a position of the subject in an infrared light image obtained by the imaging unit is adjusted to a position of the subject in the infrared light image which is first obtained out of the plurality of infrared light images obtained by the imaging unit, and wherein the superimposition unit superimposes the visible light images aligned by the visible light image alignment unit on the image of the subject generated the previous time one by one, so as to generate the image of the subject which is obtained by superimposing the plurality of visible light images on each other and has a dynamic range wider than that of the visible light image.

(29)
The image processing apparatus set forth in (26), (27) or (28), wherein the subject is a fundus, and wherein the infrared light image alignment unit uses a blood vessel as the biological information.

(30)
The image processing apparatus set forth in any one of (26) to (29), wherein the infrared light image alignment unit further uses an intersection of the blood vessel as the biological information.

(31)
An image processing method of an image processing apparatus, including causing an infrared light image alignment unit to perform alignment so as to adjust positions of a subject in a plurality of infrared light images obtained by an imaging unit which images the subject, by using biological information of the subject; causing an alignment information storage unit to store alignment information which is a result of the alignment by the infrared light image alignment unit; causing a visible light image alignment unit to perform alignment so as to adjust positions of the subject in a plurality of visible light images obtained by the imaging unit, by using the alignment information stored in the alignment information storage unit; and causing a superimposition unit to superimpose the visible light images aligned by the visible light alignment unit so as to generate an image of the subject having a dynamic range wider than that of the visible light image.

(32)

An image processing apparatus including an infrared light image alignment unit that performs alignment so as to adjust positions of a subject in a plurality of infrared light images obtained by an imaging unit which images the subject, by using biological information of the subject; an alignment information storage unit that stores alignment information which is a result of the alignment by the infrared light image alignment unit; a visible light image alignment unit that performs alignment so as to adjust positions of the subject in a plurality of visible light images obtained by the imaging unit, by using the alignment information stored in the alignment information storage unit; a superimposition unit that superimposes the plurality of visible light images aligned by the visible light alignment unit on each other; and a grayscale correction unit that performs grayscale correction on a visible light image generated by the superimposition unit superimposing the plurality of visible light images, according to biological information of the subject.

(33)

The image processing apparatus set forth in (32), wherein the imaging unit performs a plurality of imagings of the subject while irradiating the subject with irradiation light including visible light with a predetermined light amount and infrared light with a light amount larger than the predetermined light amount.

(34)

The image processing apparatus set forth in (32) or (33), further including a high resolution unit that increases the resolution of the visible light image having undergone the grayscale correction by the grayscale correction unit.

(35)

The image processing apparatus set forth in (32), (33) or (34), wherein the high resolution unit increases the resolution of the visible light image having undergone the grayscale correction by the grayscale correction unit, according to the biological information of the subject.

(36)

The image processing apparatus set forth in any one of (32) to (35), wherein the subject is a fundus, and wherein the infrared light image alignment unit uses a blood vessel as the biological information.

(37)

The image processing apparatus set forth in any one of (32) to (36), wherein the infrared light image alignment unit further uses an intersection of the blood vessel as the biological information.

(38)

An image processing method of an image processing apparatus, including causing an infrared light image alignment unit to perform alignment so as to adjust positions of a subject in a plurality of infrared light images obtained by an imaging unit which images the subject, by using biological information of the subject; causing an alignment information storage unit to store alignment information which is a result of the alignment by the infrared light image alignment unit; causing a visible light image alignment unit to perform alignment so as to adjust positions of the subject in a plurality of visible light images obtained by the imaging unit, by using the alignment information stored in the alignment information storage unit; causing a superimposition unit to superimpose the plurality of visible light images aligned by the visible light alignment unit on each other; and causing a grayscale correction unit to perform grayscale correction on a visible light image generated by the superimposition unit superimposing the plurality of visible light images, according to biological information of the subject.

(39)

A medical examination system including an imaging unit that images a subject; an imaging processing unit that acquires a plurality of captured images obtained by the imaging unit via a network and performs an image process on the plurality of captured images acquired; a storage unit that stores the captured images having undergone the image process by the imaging processing unit; and an output unit that outputs the captured images stored in the storage unit.

(40)

The image processing apparatus set forth in (39), wherein the image processing unit further includes an alignment portion that performs alignment so as to adjust positions of a subject in the plurality of captured images by using biological information of the subject; and a superimposition portion that superimposes the captured images aligned by the alignment portion so as to generate an image of the subject having a dynamic range wider than that of the captured image.

(41)

The image processing apparatus set forth in (39) or (40), wherein the image processing unit includes a superimposition portion that superimposes a plurality of captured images obtained by the imaging unit on each other; and a grayscale correction portion that performs grayscale correction on a captured image which is generated by the superimposition portion superimposing the plurality of captured images, according to biological information of the subject.

(42)

The image processing apparatus set forth in (39), (40) or (41), wherein the image processing unit further includes a high resolution portion that increases the resolution of the captured image having undergone the grayscale correction by the grayscale correction unit.

(43)

The image processing apparatus set forth in any one of (39) to (42) wherein the imaging unit performs a plurality of imagings of the subject while irradiating the subject with irradiation light including visible light with a predetermined light amount and infrared light with a light amount larger than the predetermined light amount, and wherein the image processing unit further includes an infrared light image alignment portion that performs alignment so as to adjust positions of a subject in a plurality of infrared light images obtained by the imaging unit, by using biological information of the subject; an alignment information storage portion that stores alignment information which is a result of the alignment by the infrared light image alignment portion; a visible light image alignment portion that performs alignment so as to adjust positions of the subject in a plurality of visible light images obtained by the imaging unit, by using the alignment information stored in the alignment information storage portion; and a superimposition portion that superimposes the visible light images aligned by the visible light alignment portion so as to generate an image of the subject having a dynamic range wider than that of the visible light image.

(44)

The image processing apparatus set forth in any one of (39) to (43), wherein the imaging unit performs a plurality of imagings of the subject while irradiating the subject with irradiation light including visible light with a predetermined light amount and infrared light with a light amount larger than the predetermined light amount, and wherein the image processing unit further includes an infrared light image alignment portion that performs alignment so as to adjust positions of a subject in a plurality of infrared light images obtained by the imaging unit, by using biological information of the subject; an alignment information storage portion that stores alignment information which is a result of the alignment by the infrared light image alignment portion; a visible light image alignment portion that performs alignment so as to adjust positions of the subject in a plurality of visible light images obtained by the imaging unit, by using the alignment information stored in the alignment information storage portion; a superimposition portion that superimposes the plurality of visible light images aligned by the visible light alignment portion on each other; and a grayscale correction portion that performs grayscale correction on a visible light image generated by the superimposition portion superimposing the plurality of visible light images, according to biological information of the subject.

(45)

The image processing apparatus set forth in any one of (39) to (44), wherein the subject is a fundus.

REFERENCE SIGNS LIST

100 FUNDUS IMAGE PROCESSING APPARATUS, 101 IMAGING UNIT, 102 IMAGE PROCESSING UNIT, 103 STORAGE UNIT, 104 OUTPUT UNIT, 111 INPUT IMAGE BUFFER, 112 SUPER-RESOLUTION PROCESSING PORTION, 113 SR IMAGE BUFFER, 114 CALCULATION PORTION, 121 MOTION VECTOR DETECTION SECTION, 122 MOTION COMPENSATION SECTION, 123 DOWN-SAMPLING FILTER, 124 CALCULATION SECTION, 125 UP-SAMPLING FILTER, 126 BACKWARD MOTION COMPENSATION SECTION, 200 FUNDUS IMAGE PROCESSING APPARATUS, 202 IMAGE PROCESSING UNIT, 212 BIOLOGICAL INFORMATION ALIGNMENT PROCESSING PORTION, 213 SUPER-RESOLUTION PROCESSING PORTION, 214 SUPER-RESOLUTION RESULT IMAGE BUFFER, 241 INPUT IMAGE BLOOD VESSEL EXTRACTION SECTION, 242 SUPER-RESOLUTION RESULT IMAGE BLOOD VESSEL EXTRACTION SECTION, 243 INPUT IMAGE INTERSECTION EXTRACTION SECTION, 244 SUPER-RESOLUTION RESULT IMAGE INTERSECTION EXTRACTION SECTION, 245 INTERSECTION ALIGNMENT PROCESSING SECTION, 246 BLOOD VESSEL ALIGNMENT PROCESSING SECTION, 271 SUPERIMPOSITION PROCESSING COMPONENT, 272 SHIFT PROCESSING COMPONENT, 273 EXTENSION PROCESSING COMPONENT, 274 ROTATION PROCESSING COMPONENT, 275 ENLARGEMENT AND REDUCTION PROCESSING COMPONENT, 276 CONVERGENCE DETERMINATION COMPONENT, 301 PSF (POINT SPREAD FUNCTION) ESTIMATION SECTION, 302 BLURRING REMOVAL PROCESSING SECTION, 303 SUPERIMPOSITION PROCESSING PORTION, 400 FUNDUS IMAGE PROCESSING APPARATUS, 402 IMAGE PROCESSING UNIT, 413 NOISE REDUCTION PROCESSING PORTION, 414 NOISE REDUCTION RESULT IMAGE BUFFER, 415 TONE REPRODUCTION PROCESSING PORTION, 416 SUPER-RESOLUTION PROCESSING PORTION, 451 IMAGE BUFFER, 452 PARAMETER SETTING SECTION, 452 TONE CURVE CALCULATION SECTION, 454 MAPPING SECTION, 461 ADJUSTMENT TARGET PARAMETER SELECTION COMPONENT, 462 PARAMETER INITIAL VALUE STORAGE COMPONENT, 463 PARAMETER STORAGE COMPONENT, 464 BRIGHTNESS-VALUE-BEFORE-CORRECTION CALCULATION COMPONENT, 465 BRIGHTNESS VALUE STORAGE COMPONENT, 466 PART RECOGNITION COMPONENT, 467 PARAMETER ADJUSTMENT COMPONENT, 468 TONE CURVE CALCULATION COMPONENT, 469 MAPPING COMPONENT, 470 PART CHECKING COMPONENT, 471 BRIGHTNESS-VALUE-AFTER-CORRECTION CALCULATION COMPONENT, 472 COMPARISON COMPONENT, 473 DATA OUTPUT COMPONENT, 481 LEARNING DICTIONARY STORAGE SECTION, 482 IMAGE PROCESSING SECTION, 483 PART RECOGNITION SECTION, 484 PART EVALUATION CRITERION STORAGE SECTION, 485 PART IMAGE EVALUATION SECTION, 486 IMAGE SELECTION SECTION, 564 BRIGHTNESS-VALUE-BEFORE-CORRECTION CALCULATION COMPONENT, 565 BRIGHTNESS VALUE STORAGE COMPONENT, 566 PART RECOGNITION COMPONENT, 569 MAPPING COMPONENT, 570 PART CHECKING COMPONENT, 571 BRIGHTNESS-VALUE-AFTER-CORRECTION CALCULATION COMPONENT, 572 COMPARISON COMPONENT, 700 FUNDUS IMAGE PROCESSING APPARATUS, 702 IMAGE PROCESSING UNIT, 711 INPUT IMAGE BUFFER, 712 INFRARED LIGHT IMAGE ALIGNMENT PROCESSING PORTION, 713 INITIAL IMAGE BUFFER, 714 ALIGNMENT INFORMATION BUFFER, 715 VISIBLE LIGHT IMAGE ALIGNMENT PROCESSING PORTION, 716 SUPER-RESOLUTION PROCESSING PORTION, 717 SUPER-RESOLUTION RESULT IMAGE BUFFER, 800 FUNDUS IMAGE PROCESSING APPARATUS, 811 NOISE REDUCTION PROCESSING PORTION, 812 NOISE REDUCTION RESULT IMAGE BUFFER, 900 REMOTE MEDICAL EXAMINATION SYSTEM, 911 SMALL FUNDUS CAMERA, 912 DOCTOR TERMINAL DEVICE, 913 NURSE TERMINAL DEVICE, 914 PATIENT TERMINAL DEVICE, 915 NETWORK, 916 IMAGE PROCESSING DEVICE, 917 DATABASE

The invention claimed is:

1. A remote fundus diagnostic system, comprising:
an external information processing device;
a handheld portable fundus imaging apparatus that includes:
  a light source configured to emit light of an infrared wavelength band and a visible wavelength band,
    wherein a first amount of the light emitted in the infrared wavelength band is larger than a second amount of the light emitted in the visible wavelength band in an operation mode of the light source; and
  a camera including:
    a lens; and
    a CMOS type image sensor configured to:
      receive the light passed through the lens; and
      capture an infrared light image and a plurality of visible light images of a fundus of an eye;

a circuitry configured to control the light source and the camera; and a wireless communication circuit in the handheld portable fundus imaging apparatus, the wireless communication circuit is configured to transmit, to the external information processing device, the captured infrared light image and the plurality of visible light images of the fundus, and biological information of a subject, wherein the external information processing device includes:
 a communication circuit configured to receive the captured infrared light image and the plurality of visible light images of the fundus, and the biological information of the subject from the handheld portable fundus imaging apparatus; and
 a processing circuitry configured to:
  adjust positions of the fundus in the captured infrared light image and in the plurality of visible light images based on the biological information of the subject;
  generate at least one output image based on at least one of the captured infrared light image and a superimposition of the plurality of the visible light images, wherein a dynamic range of the at least one output image is wider than a dynamic range of the plurality of visible light images; and
  control a memory to store the generated at least one output image with the biological information,
  wherein a brightness of the at least one output image is higher than a brightness of each of the plurality of visible light images.

2. The remote fundus diagnostic system of claim 1, wherein the camera is further configured to sequentially capture the infrared light image and the plurality of visible light images.

3. The remote fundus diagnostic system of claim 1, wherein the wireless communication circuit is further configured to transmit, to the external information processing device, a plurality of images including the infrared light image and the plurality of visible light images.

4. The remote fundus diagnostic system of claim 1, wherein
the circuitry is further configured to control the camera to sequentially capture the infrared light image and the plurality of visible light images, multiple times, and
the camera is controlled based on the first amount of the light emitted in the infrared wavelength band that is lower than a threshold amount.

5. The remote fundus diagnostic system of claim 1, wherein the external information processing device is further configured to process the captured infrared light image and the plurality of visible light images based on a tone reproduction process associated with a tone curve.

6. The remote fundus diagnostic system of claim 1, wherein the external information processing device is further configured to generate at least one image from a plurality of images received from the handheld portable fundus imaging apparatus.

7. The remote fundus diagnostic system of claim 6, wherein a resolution of the at least one image is higher than a resolution of the plurality of images.

8. The remote fundus diagnostic system of claim 7, wherein the external information processing device is further configured to detect a plurality of positions of the subject between the plurality of images.

9. The remote fundus diagnostic system of claim 8, wherein the external information processing device is further configured to detect the plurality of positions of the subject between the plurality of images based on a position of blood vessels.

10. The remote fundus diagnostic system of claim 8, wherein the external information processing device is further configured to detect the plurality of positions of the subject between the plurality of images based on a position of intersection of blood vessels.

11. The remote fundus diagnostic system of claim 6, wherein the external information processing device is further configured to detect a motion vector from the infrared light image.

12. The remote fundus diagnostic system of claim 1, wherein the external information processing device is further configured to acquire additional information regarding the generated at least one output image from a database.

13. The remote fundus diagnostic system of claim 12, wherein the additional information is information indicating at least one of a target part, a patient, a physical constitution of the patient, or clinical history.

14. A remote fundus diagnostic method, comprising:
in a handheld portable fundus imaging apparatus:
 emitting, by a light source, light of an infrared wavelength band and a visible wavelength band,
 wherein a first amount of the light emitted in the infrared wavelength band is larger than a second amount of the light emitted in the visible wavelength band in an operation mode of the light source;
 receiving, by a CMOS type image sensor, the light passed through a lens;
 capturing, by the CMOS type image sensor, an infrared light image and a plurality of visible light images of a fundus of an eye;
 controlling the light source and a camera; and
 transmitting, to an external information processing device, the captured infrared light image and the plurality of visible light images of the fundus, and biological information of a subject, and
in the external information processing device:
 receiving the captured infrared light image and the plurality of visible light images of the fundus, and the biological information of the subject from the handheld portable fundus imaging apparatus;
 adjusting positions of the fundus in the captured infrared light image and in the plurality of visible light images based on the biological information of the subject;
 generating at least one output image based on at least one of the captured infrared light image and a superimposition of the plurality of the visible light images, wherein a dynamic range of the at least one output image is wider than a dynamic range of the plurality of visible light images; and
 controlling a memory to store the generated at least one output image with the biological information,
 wherein a brightness of the at least one output image is higher than a brightness of the plurality of visible light images.

* * * * *